(12) United States Patent
Henry

(10) Patent No.: US 10,442,841 B2
(45) Date of Patent: Oct. 15, 2019

(54) BREAD QUALITY PROTEIN AND METHODS OF USE

(71) Applicant: THE UNIVERSITY OF QUEENSLAND, St Lucia (AU)

(72) Inventor: Robert Henry, St Lucia (AU)

(73) Assignee: THE UNIVERSITY OF QUEENSLAND, Brisbane (AU)

( * ) Notice: Subject to any disclaimer, the term of this patent is extended or adjusted under 35 U.S.C. 154(b) by 0 days.

(21) Appl. No.: 15/539,350

(22) PCT Filed: Dec. 23, 2015

(86) PCT No.: PCT/AU2015/050835
§ 371 (c)(1),
(2) Date: Jun. 23, 2017

(87) PCT Pub. No.: WO2016/101034
PCT Pub. Date: Jun. 30, 2016

(65) Prior Publication Data
US 2017/0349636 A1    Dec. 7, 2017

(30) Foreign Application Priority Data
Dec. 23, 2014   (AU) ................................ 2014905219

(51) Int. Cl.
| | | |
|---|---|---|
| *C07K 14/415* | (2006.01) |
| *C12N 15/82* | (2006.01) |
| *A01H 1/04* | (2006.01) |
| *A01H 5/10* | (2018.01) |
| *C12Q 1/6895* | (2018.01) |
| *A01H 6/46* | (2018.01) |

(52) U.S. Cl.
CPC ............. *C07K 14/415* (2013.01); *A01H 1/04* (2013.01); *A01H 5/10* (2013.01); *A01H 6/4678* (2018.05); *C12N 15/8234* (2013.01); *C12N 15/8242* (2013.01); *C12Q 1/6895* (2013.01); *C12Q 2600/13* (2013.01)

(58) Field of Classification Search
None
See application file for complete search history.

(56) References Cited

U.S. PATENT DOCUMENTS

2012/0240286 A1*  9/2012  Henry ................. C07K 14/415
                                                                800/278

FOREIGN PATENT DOCUMENTS

WO    2008/040061    4/2008

OTHER PUBLICATIONS

Int'l Preliminary Report on Patentability for PCT/AU2015/050835, eight pages, dated Jun. 27, 2017.
International Search Report for PCT/AU2015/050835, six pages dated Mar. 1, 2016.
Written Opinion of the ISA for PCT/AU2015/050835, seven pages dated Mar. 1, 2016.
Oliver & Allen "The mixing requirement of the Australian hard wheat cultivar, Dollarbird" *Cereal Chemistry*, vol. 71, No. 1, pp. 51-54 (1994).
Furtado et al. "A novel highly differentially expressed gene in wheat endosperm associated with bread quality" *Scientific Reports*, vol. 5, No. 10446, fourteen pages. (May 2015).

* cited by examiner

*Primary Examiner* — Eileen B O Hara
(74) *Attorney, Agent, or Firm* — Nixon & Vanderhye P.C.

(57) ABSTRACT

An isolated protein that is highly abundant in the seed of wheat varieties with desirable breadmaking qualities is provided. Associated promoters and promoter active fragments are also provided. Further provided are plants or plant parts with improved or enhanced breadmaking properties, and methods of producing such plants, wherein the abundance of the isolated protein is increased or enhanced. Such plants and/or plant parts may be used in the production of plant products, for example bread and read products.

26 Claims, 29 Drawing Sheets
Specification includes a Sequence Listing.

```
>SEQ ID NO:12      (wbm CDS sequence)
ATGTTCTTCTCCACAAAGATGTGTGTTGCTACCATCATGGTGCTAGCCCTGACGCTCTCG
CCTCATGGCACCGTTGACGCCGGCCACCTCTCTTCAAACTGGGGCTCTTGTCCAGATGGA
CAGTCAGTGCAATGCATTGGGAGACCGCCATTCTGCAAGTGTGTACCAAACCTTCAGTTT
GTGGATCGCCAGCGTACTGTGTACAACATGGGAGCTGCCCGTGCATAG >SEQ ID NO:1       (wbm amino acid sequence)
MFFSTKMCVATIMVLALTLSPHGTVDAGHLSSNWGSCPDGQSVQCIGRPPFCKCVPNLQFVDRQRTVYN
MGAARA >SEQ ID NO:23      (wbm gene sequence)
GAGAACAAGGGACTACACAGACATAAAGAGATCCATAACTTAACCTGAAG
AGTGTGACGAGATAGGCAGCCATGTTCTTCTCCACAAAGATGTGTGTTGC
TACCATCATGGTGCTAGCCCTGACGCTCTCGCCTCATGGCACCGTTGACG
CCGGCCACCTCTCTTCAAACTGGGGCTCTTGTCCAGATGGACAGTCAGTG
CAATGCATTGGGAGACCGCCATTCTGCAAGTGTGTACCAAACCTTCAGTT
TGTGGATCGCCAGCGTACTGTGTACAACATGGGAGCTGCCCGTGCATAGT
AACTAGAGTTTCTAGTAATATACTATAGCAATAAGAGTCATGCAGCATCC
CTGCATGCATCGCCAGAAAACTTCTGTACAACGGAAAGCGTGTCAACTGA
ACTTGATATATGTATGCACCATTGCATGCATGTTGTTCCGTGTAGTACCA
GAAAATAAAATAAGGGCTGCTACTATGTATGCAGGCCATTTGCTTTTAGC
AAAAAAAAAAAAAAAAAAAAAAAAAAAAA Translation of SEQ ID NO:12 to SEQ ID NO:1

DNA:    atgttcttctccacaaagatgtgtgttgctaccatcatggtgctagccctgacgctctcg
+1fr:   MetPhePheSerThrLysMetCysValAlaThrIleMetValLeuAlaLeuThrLeuSer DNA:    cctcatggcaccgttgacgccggccacctctcttcaaactggggctcttgtccagatgga
+1fr:   ProHisGlyThrValAspAlaGlyHisLeuSerSerAsnTrpGlySerCysProAspGly DNA:    cagtcagtgcaatgcattgggagaccgccattctgcaagtgtgtaccaaaccttcagttt
+1fr:   GlnSerValGlnCysIleGlyArgProProPheCysLysCysValProAsnLeuGlnPhe DNA:    gtggatcgccagcgtactgtgtacaacatgggagctgcccgtgcatag
+1fr:   ValAspArgGlnArgThrValTyrAsnMetGlyAlaAlaArgAlaAm*
```

A
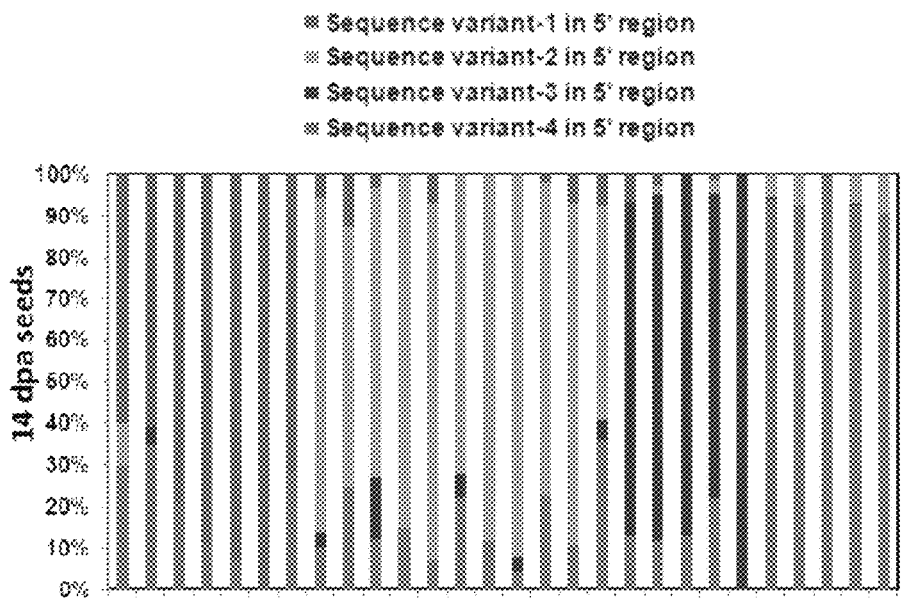
C
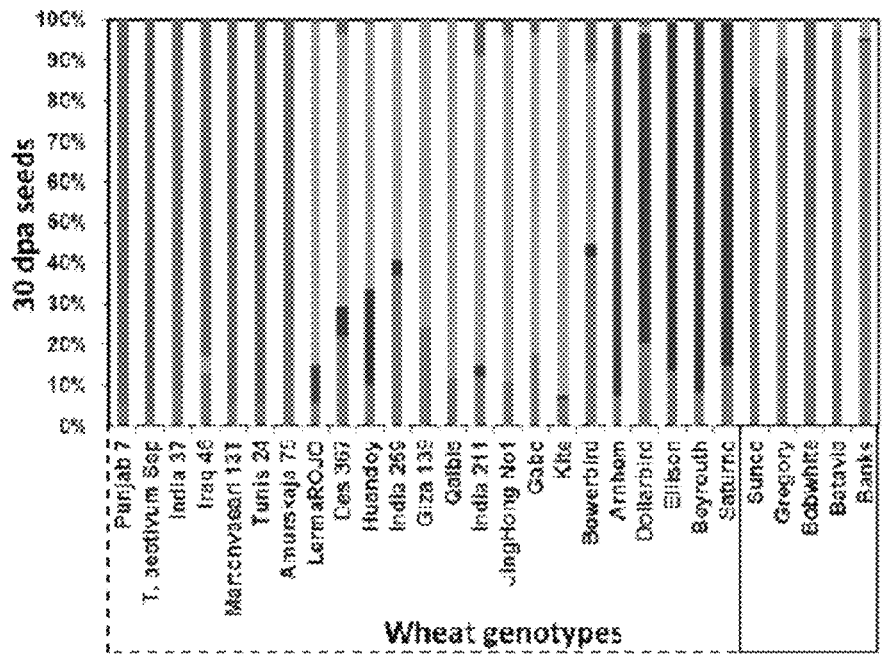
Figure 6.

B
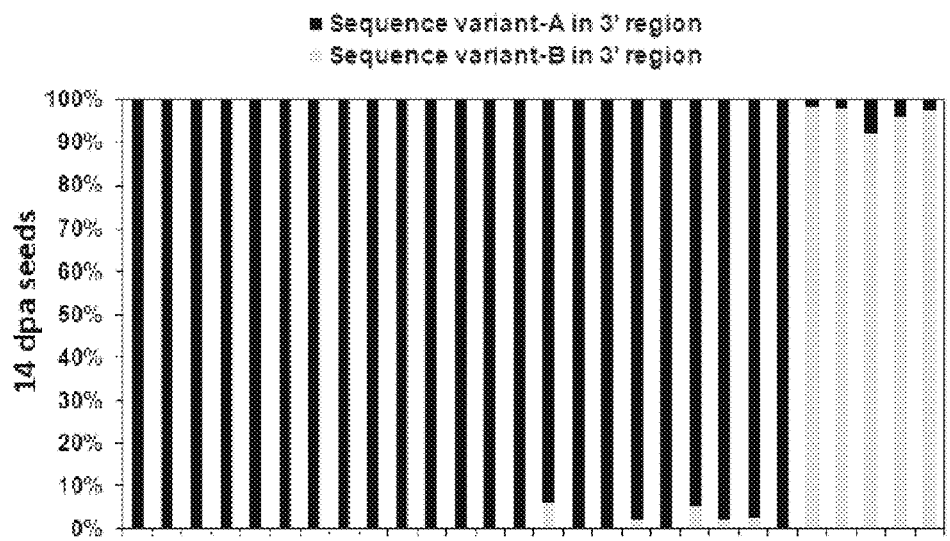
D
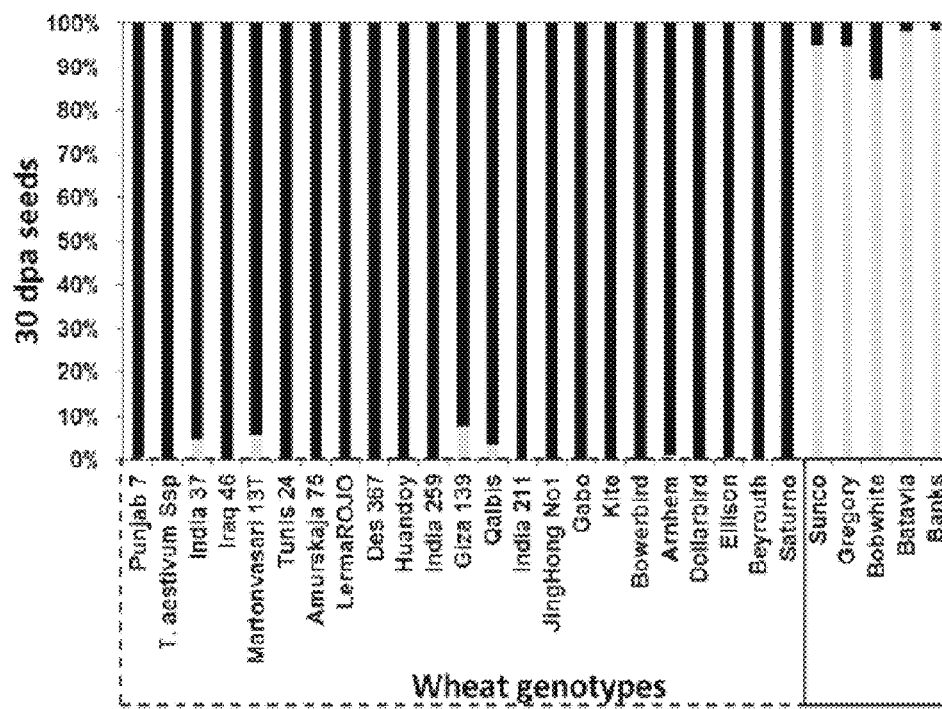
Figure 6 cont.

```
CAACATACGGCAACTCATTTGTAATTTACTGAACAGTTAGTCAGCTACCATGGTGTATAAGACCTGCTATACCATATTGTTGTCGTATATTCTTAT
ATAAGCCTTTTCTCATACCATCTCATGTATATGAAATCTGTCATGCACGCAAACACGCAACCACTGAGGGTACGCCACGTTGAACTAGCAGGCTCT
TGTTTCTCAATGCAAGCAAGCTCCGTTGGCTGTTAGGATTAGATCCTAACCACCTTAGGTGGGAGAGAAGGCGCCGCCGCTGTGGCATTTGTCGTG
GTCTTCTAGATTACCTGCTCGGTCACCTTAGGGGTACCTCTAGGTATTTGTTTTTACTTTTTGAGACAAACTCATATAAAGCTTTTAATTTATTCC
ACCGTCACAAGATTTACAGGGTTGAAAACAAGATCTCCGGGCTGTCCTAAACCAAGCATGGCGGTCAGTACCCAGCGTTAAAGTGTGCTTTGCAAA
GAAGCACAATGTTTGTTCCAAGGATGCGAACATGGCACCAGCCGTCTGTCTCCGCCCATTCTGCATCCTCCTGCTCTACTTACTTTACACTTACA
GTACAAGCAGGTATGTCACCTTATTTATTGAAAATTTGACCTCATATCACTCTCAATTACAGGGGCTGGCGAATAATAAAACAAACTAAAGGAAGG
ATATGGATTATGGGAAGCCATGTGTAAGATCAATGGAGTGGAGGGCTAAACAAGGAAAGTACACTTCGGATTTCGAATCACTCCCAGCTAATTCTG
TTTTCTCGGGGAAGCAACCTGTTCTAGATTTGGAATCACTCCCAACCAATCTTCTTATTGGGGAAACAATTTGTGCCAGATTTGGAATCACTCCCA
ACTAATTCTGTTTTCCAGGGGAAACAATTAATCCACGCCACCTAAACATGAGTAAAGTACGAAGTACACGTACTCAAGTCTATCTCGCTATATCGG
TGGGTGTTTTGTGCGTTAGTACCATGTAAAAAATAAATAGATGACAAACTGCATTGCTCGTTAACTTGCACGCTAGCACTAAGTACACCTACAGAG
ATAGATGTAGAGCCCTCCATATGTGGTGCCTTTTACGCTTAATGACAATGAAATGCGCGCCAGCTGCATTGCTTTTTCACTTGTGTGCTGCAAATA
TGTACACGCGAACGGATGTAGAGTATTCCATATATAGGTGGTGGTTTGTACGTCAATACTTGTCTCATATCCGCAAAAGCATAGCTTTTCCACTT
TGTTGCGGGCACCAAATAGACAAATCGGACTATAAATTGATACGCCCAAGGCAAAGCCCATAGATCAAGGGACTACACAGACATAAAGAGATCCAT
AACTTAACCTGAAGAGTGTGACGAGATAGGCAGCC
```

Figure 10

>SEQ ID NO:2  (GWSeqVar1 Ki-K3A)
CTGTGTGCGTAGGAAAATAAGTGGCCTTGCTGCACTGGGCCTCAACGCCC
GGGCCAGGTACGAAATCTGGACAACCCGTTTTTTTTCTTGCACACGAAAT
CACAAATTTAGTACCACCTCGGATAAAAGAAAAATCTTTTCATTGGTGAA
TGGATGAAAAAAGCGGAGAAACGCACCTTGCTTTATTAGTACTCCCTCCG
TTTCTTTATAGTCTGCATATAACATTTGGTCAAAGTCAAAGTTTGTAAAG
TTTGACCAACTTTGTAGAAAAAAATATCAACATCTACAATAATAAAGCTA
TATGGTTTGAAAATTAATTTCATGATGCATCTAAAATATTGATTTCATT
TTGTGAATCTTGATATTTTTTCTATAAACCTAGTCAAAGTTAACAAAGT
TTGACTTTGCCCAAACCTTATATGCAAACTAAAAGAAACGGAGGGAGTA
GGTATAGAATTATATTAGAACGGTTGACCGCAAATACTTGCGCTGCGAGA
CCCGTCCATACCTGCTGAAAAGAATGAAGATGTGGAGGAATTTAGATCAT
CAATCCGATTGAAGGTAAGGTAGAAAGCATGGACCCCACAGCTCAATCTG
CTAACCGTCTAGGCTACAAGCTAGTGTAACTCTGCATATCCCTGTTAGCC
ATGTAACTTCAAGGGGCCAATGATCGAAGTAAGATCAATGGTCTTCCTTA
CCTGCCATTAACGCATAACAGAACAAACTGTCTGTCAACAGGACTGATAT
TTGGTTTTTGTCCGCTCAACAACTTTACATGTAGACATTAATCATCTACT
AGCTCACTCAGAATTAGAACGATTGAGATTTTGCTGAGAAGGTGAGACTA
GACGGGCTTCTAAGCAGGTAGGATTCACAAGCTCAAACCGCTGAGCTAAA
ACTATGCATTTGGAAACACTCCCACCTAATTTTGTTTTTTCGGGGAAACA
ATCTACGCCAGATTTGGAGGTACTCCCAACTAATTTTGTTTCCTTAGGAA
ACAATCTACGCCGAGCAGACAAGAAGGGAGGGATCCCGATAACTTACGGT
AATGATAACTTCCGAACGTTCGGGAGTTAAGCAYGGCAACCCGAACGGGT
TTAGATGGCAAGTTTAGTTTGCGTGAGATTAGGGAAACATGGCAATTTTC
TGCAAAAAAGAAAAGGATAAAGTTGCCATCCCCTATGAACTAAAGTTG
CCATATAAAAACGTTCGGGACGAAACGCTCAAAATCCCAACGTTCGGGAG
TTATTGGATTCCATAACTTAAGAGTTAAGTACAAAGTACACGTRCACACA
TTTATCTTGCTATATCGGTGGTGTTTATGCGTTGGTGCCGATTAAATAC
ATGACAAACTACGTTGCTCGTTAACTTGCACGCTAGCACTAAGTACACCT
ACACAGATAGATCTAGAGCTCTCCGTATGTGGTGCTTTTACACTTAACG
GTAATCAAATGCTTGCCGGCTGCATTGCTTTTTCGCTTGTACTCTACAAC
TACATACACGTATACAGACCTACAGTGCTGCATAGGTGGTGGTTTGTACG
TCAAGACTGATCTAATATCTGCCAAACGCATAGCTTTTCCACTTATGCCG
GCATCCATCCATCATCGACGCATATCCATATACATACGGAGTATAAATTA
ACACGGCCCGAGGTGAGCGCACACCACAGCGGACAACACAGACATAAAGT
GATCCATAAGATAACCTGAAGAGGGTGACGGGCTAGGCAGCCATG

Figure 15

>SEQ ID NO:3 (GWSeqVar1 Ba-B3A)
CTGTGTGCGTRGGAAAATAAGTGGCCTTGCTGCACTGGGCCTCAACGCCC
GGGCCAGGTACGAAATCTGGACAACCCGTTTTTTTTCTTGCACACGAAA
TCACAAATTTAGTACCACCTCGGATAAAAGAAAAATCTTTTCATTGGTGA
ATGGATGAAAAAGCGGAGAAACGCACCTTGCTTTATYAGTACTCCCTCC
GTTTCTTTTTAGTCTGCATATAACATTTGGTCAAAGTCAAAGTTTGTAAA
GTTTGACCAACTTTGTAGAAAARAATATCAACATCTACAATAATAAAGCT
ATATGGTTTGAAAATTAATTTCATGATGCATCTAAAATATTGATTTCAT
TTTGTGAATCTTGATATTTTTTCTATAAACCTAGTCAAAGTTAACAAAG
TTTGACTTTGCCCAAACCTTATATGCAAACTAAAAGAAACGGAGGGAGT
AGGTATAGAATTATATTAGAACGGTTGACCGCAAATACTTGCGCTGCGAG
ACCCGTCCATACCTGCTGAAAAGAATGAAGATGTGGAGGAATTTAGATCA
TCAATCCGATTGAAGGTAAGGTAGAAAGCATGGACCCCACAGCTCAATCT
GCTAACCGTCTAGGCTACAAGCTAGTGTAACTCTGCATATCCCTGTTAGC
CATGTAACTTCAAGGGGCCAATGATCGAAGTAAGATCAATGGTCTTCCTT
ACCTGCCATTAACGCATAACAGAACAAACTGTCTGTCAACAGGACTGATA
TTTGGTTTTTGTCCGCTCAACAACTTTACATGTAGACATTAATCATCTAC
TAGCTCACTCAGAATTAGAACGATTGAGATTTTGCTGAGAAGGTGAGACT
AGACGGCTTCTAAGCAGGTAGGATTCACAAGCTCAAACCGCTGAGCTAAA
ACTATGCATTTGGAAACACTCCCACCTAATTTTGTTTTTTCGGGGAAACA
ATCTACGCCAGATTTGGAGGTACTCCCAACTAATTTTGTTTCCTTAGGAA
ACAATCTACGCCGAGCAGACAAGAAGGGAGGRATCCCGATAACTTACGGT
AATGATAACTTCCGAACGYTCGGGAGTTAAGCATGGCAACCCGAACGGGT
TTAGATGGCAAGTTTAGTTTGCGTGAGATTAGGGAAACATGGCAATTTTC
TGCAAAAAAGAAAAGGATAAAGTTGCCATCCCCTATGAACTAAAGTTG
CCATATAAAACGTTCGGGACGRAACGCTCAAAATCCCAACGTTCGGGAG
TTATTGGATTCCATAACTTAAGAGTTAAGTACAAAGTACACGTACACACA
TTTATCTTGCTATATCGGTGGTGTTTTATGCGTTGGTGCCGATTAAATAC
ATGACAAACTACGTTGCTCGTTAACTTGCACGCTAGCACTAAGTACACCT
ACACAGATAGATCTAGAGCTCTCCGTATGTGGTGCTTTTTACACTTAACG
GTAATCAAATGCTTGCCGGCTGCATTGCTTTTTCGCTTGTACTCTRCAAC
TACATACACGTATACAGACCTACAGTGCTGCATAGGTGGTGGTTTGTACG
TCAAGACTGATCTAATATCTGCCAAACGCATAGCTTTTCCACTTGTGCCG
GCATCCATCCATCATCGACGCATATCCATATACATACGGAGTATAAATTA
ACACGGCCCGAGGTGAGCGCACACCACAGCGGACAACACAGACATAAAGT
GATCCATAAGATAACCTGAAGAGGGTGACGGGCTAGGCAGCCATG

Figure 15 cont.

```
>SEQ ID NO:4    (GWSeqVar5 Ki-K1B)
CGCACCGACTGTGGGTTTTCTCCCTCGCCAATGTCGACCGCGTCTACGCA
GAACATTGTTCCCTTCCCCCAGCTGCGGGATCAGGCCCGTCGTTCTATGC
TTGTGAAGAGAGCAACCTAAGCAAGCAGGCTTGTAGCTTAGGCTCCTGCT
AGTGTATATATAGTGGTTTTCTTTTTCTCTAATATCAACCATTTTATAT
TGTGTATGTGGTGCTTTTTACACTTAACGGTAATCAAATGCTTGCCGGCT
GCATTGCTTTTTCGCTTGTACTCTACAACTACATACACGTATACAGACCT
ACAGTGCTGCATAGGTGGTGGTTTGTACGTCAAGACTGATCTAATATCTG
CCAAACGCATAGCTTTTCCACTTGTGCCGGCATCCATCCATCATCGACGC
ATATCCATATACATACGGAGTATAAATTAACACGGCCCGAGGTGAGCGCA
CACCACAGCGGACAACACAGACATAAAGTGATCCATAAGATAACCTGAAG
AGGGTGACGGGCTAGGCAGCCATG

>SEQ ID NO:5    (GWSeqVar4 Ki-K4B)
CCTCAAGTGTATAGGATCTAAATTATATTAGATCAGTTGACCGCAAATAC
ATGCGTTGCGACACCCGTCCATACCTGCTGAAAAGAATGAAGATGTGGAG
GAATTTAGATCATCAATCCGGTTGAAGGTAGAAAGCGTCGACCCCACAGC
TCAATCTGCTAACCGTCTAGGCTACAAGCTAGTGTAACTCTCATATCCCT
GTTAACCATGTAACTTCAAGGGACCAATGATCGAAGTAAGATCAATGGTC
TTCCTTACCTGTCATTAACGCATACCAGAACAAACTGTCTGTCGACAGGA
CTGATATTTTGTTTTTGTCCGCTCAACAACTTTACATGTAGACACTAGAC
ACTAATCATCTACTAGCTCACTCAGAATTAGAACGATTGAGATTTTGCTG
AGAAGGTGGGACTAGACGGCTTCTAAGCAGGTAGGATTCACAAGCTCAAA
CCACTGAGCTAAAACTATGCATTTGGAAACACTCCCACCTAATTTTGTTT
TCTCAGGGAAACAATCTACGCCAGATTAATTTGGAAGCACTCCCAACTAA
TTTTGTTTTTAGGGAAGCAATCTACGCCATATGTGGTGCCTTTTACACTT
ACGGTAATCAAATGCATGGCAGGTGCATTGCTTTTCCTCTTGTACTCTAC
AACTACATACACGTATACAGATCTAGAGTGCTCCATAGGTGGTGGTTTGT
ACGTCAAGACTGATCTAATATCTGCCAAATGCATAGCTTTTCCACTTGTG
CCGGCATCCATCCATCGTCGACGCATATCCATATACATACGGGACTATAA
ATTAACACGGCCCGAGGTGAGCGCACACGACAACGGACTACAAAGACATA
GAGTGGTCCATAGGATAACCTGAAGAGGGTGGCGGGCTAGGCAGCAGCCA
TG
```

Figure 15 cont.

>SEQ ID NO:6    (GWSeqVar4 Ba-B2A)
AACATGGTTATTTATTTCTGTCAAATTGTCAAATTGTAATCTGAATAATA
TGATGCTACCAAAARGGTCCCACTTYAATAGAACCYGACAACTGGGACCC
ATCTGACTAGTGGACCCTTCTTTTGGAAAAAAAGAAAAACTAAATTCATT
TAGACAAAACRAAAAGGCCACAACCCAACAATAAAAGGCTGCAATATTG
GACTYGGCCCATGAACCCAACCAAAAATYGACAGACAGAAAAAAACACRA
ATAGGCTGAATTGTTRCGCTAGGCCCATGTAGAAAATCGAATTGGACCGG
GCTGAATCTTCTGCCACATCAGATTGCCACGCTAGAYGCCTACGTGGCCT
GGGGAGGTTGCTAGTGACCAAAACGCCATAGTAGACGTATTTTGGTCATA
AACATCTTCGACCATTCCAAAAGAAAGGTCGCTATAGTCAGTTTATGACG
GCCAGCTTTTGACCTTATGTTTTTTGTCATAAAAAGGTCACAAATGGAAA
TTTGTGACCATTCAGTGACCAATAATGGTGGTCATAAGTTGACATATTTC
TTGTAGTGAAAGTGGTCGCCCGCCTCCGTTGAGTGCACGACACTCTACTA
CTAAACTGAGTAAGTTCCTCTTTATTACTGTATGCACGCCTGTCCATKTG
TTAAAGAACAAATACGGATTTATGTCCTATGAATTGACCCATACATTGGT
CTCAATAGAAACAAGAAATTTATGGAGTACGGATGTGTATGTGTAACTAT
GAGTCTTATGGTGTGAAGCTATCTGGACTATGCACGATGATGGTGAGAGC
AGACGGCTAGGCTGTCGGCATATCTCTGCCATGTGGCGTCTCCTGGTCGT
GCAGCACTTGATGGCGGCGCCATCAGCCACCGTTAGGTGTCGAACTTTGT
CGACGGCCTGAGCCGTCGGCATAGCTATATGGACGCCGTCGGGAAAGCAT
CTATGCCGACGGGCTTTTTTATGCTGAGCKGCATYCCTCGCAGAGTGATG
RCGCCCCAAACGTATATTGTTGCGGAGCGGCCTTACACCGACGGGGTCAT
CGGCATTAGCCTGTCGKTCACAGGAATTCTGGCTATTCGACGCCTGGGCG
TCAGCATAGAGGTTATTATGGTAGTGATGAACCCTGCTGGGCGAAAGTTT
CATTCAGCCAATAGCATGGTCCTAACTAAAAGAAGGATTTGTTATCTAG
GGAGGATGGGATTGTTTTATTGGGATTTTAATCGGTTTGAAATTGATTCC
AATTTAGGCCTCAAGTGTATAGGATCTAAATTATATTAGATCRGTTGACC
GCAAATACATGCGTTGCGACACCCGTCCATACCTGCTGAAAAGAATGAAG
ATGTGGAGGAATTTAGATCATCAATCCGGTTGAAGGTAGAAAGCGTCGAC
CCCACAGCTCAATCTGCTAACCGTCTAGRCTACAAGCTAGTGTAACTCTC
ATATCCCTGTTAACCATGTAACTTCAAGGGACCAATGATCGAAGTAAGAT
CAATGGTCTTCCWTACCTGTCATTAACGCATACCAGAACAAACTGTCYGT
CGACAGGACTGATATTTGTTTTTGTCCGCTYAACAACTTTACATGTAGA
CACTARACACTAATCATCTACTAGCTCACTCAGAATTAGAACGATTGAGA
TTTTGCTGAGAAGGTGGGACTAGACGGCTTCTAAGCAGGTAGGATTCACA
AGCTCAAACCACTGAGCTAAAACTATGCATTTGGAAACACTCCCACCTAA
TTTTGTTTTCTCAGGGAAACAATCTACGCCAGATTAATTTGGAAGCACTC
CCAACTAATTTTGTTTTAGGGAAGCAATCTACGCCATATGTGGTGCCTT
TTACACTTACGGTAATCAAATGCATGGCAGGTGCATTGCTTTTCCTCTTG
TACTCTACAACTACATACACGTATACAGATCTAGAGTGCTCCATAGGTGG
TGGTTTGTACGTCAAGACTGATCTAATATCTGCCAAATGCATAGCTTTTC
CACTTGTGCCGGCATCCATCCATCGTCGACGCATATCCATATACATACGG
GACTATAAATTAACACGGCCCGAGGTGAGCGCACACGACAACGGACTACA
AAGACATAGAGTGGTCCATAGGATAACCTGAAGAGGGTGGCGGGCTAGGC
AGCAGCCATG

Figure 15 cont.

>SEQ ID NO:7    (GWSeqVar6 Ba-B1A)
GGGGCAGGGGAGAGGGGGGAGGCGCAGCCTTGCCTCTTCCTCCAAGGAAG
GGGTGCGGCTAAGAGGGGGGAGGAGTCCATCCTCCCCAAGGCACCTCGGA
GGTGCCTTCCCCTTTTAGGACTCTTCCCTCTAGGGTTCCCTAGGCGCATG
GGCCTCTTGGGGCTGGTGCCCTTGGCCCATGTAGGCCAAGGCGCACCCCC
TACAGCCCATGTGGCCCCCGGGGCAGGTGGCCCCACCCGGTGGGCCCCC
GGGACCCTTCCGGTGGTCCCGGTACAATACCGATGACCCCGAAACTTGTC
CCGATGGCCGAAACAGGACTTCCTATATATAAATCTTTACCTCCGGACCA
TTCCGGAACTCCTCGTGACTATAAATTGATACGCCCAAGGCAAAGCCCAT
AGAACAAGGGACTACACAGACATAAAGAGATCCATAACTTAACCTGAAGA
GTGTGACGAGATAGGCAGCCATG

>SEQ ID NO:8    (GWSeqVar2 Ki-K2A)
AATCACATGCAAAATTTAAGATAAGACTACCTTATCGACCATTGTACATG
CCCTAACTTATAGTTAAGTACGAAGTACACGTACACAAGTTTGTCTTGCT
ATATCGGTTGTGTTTTGTGCGTTAGTGCTGATTAAATACATGACAAACTG
CATTGCTTGTTAACTTGCACGCTAGCACTAAGTATACCTACGCATATAGA
TCTAGAGTGCTCCATACGCTGGTGCCTTTCACACTTAATGACAATCAAAT
GCATGACAGTTGCCCTGCATTTTGCCTTGTGCGCTAGCACTACGCACACG
TTGAAGGATCTAGAGTGCTTCATAGGCGATGGTTTGCACGTTACCCTAAT
GAGATATCTATCAAACCATTCCCTTCTCATTTGTGTTGGTCTCCATCTGT
CATCGGCACCAAGCAAACCTACGGAACTATAAATTAACAGTTTTGCTAGA
ACTCATCTAGCTGAGTTTTAGTTATGTCTCATTCACTTTTATAGCCATTG
GATATGATGCTATAAGATGCGTGTGCTGATGTGGGTTGATACTTCTTT
TCTATCTGTTTTGTCTTCCAGATGAATGAGACTAAATTATATCTCATCTA
AATGAGTTCTAGGTACTCCCATAAATTAACACGGCCTGAGGTGAGTCCAC
ACCACAACAAACTACACAGGCAAAGTGATATCCATAAATTGACCTGAAGG
GCGACCTGCAAGCCCGCCATG

Figure 15 cont.

```
>SEQ ID NO:9    (GWSeqVar2 Ba-B4A)
CCTACCCTAGTTGAGAAGTTTTTTTGATCCATTGAAAGCTGAGACGTGTC
TACTGACCCATAAGGCCCAGCCGGACGACAGGTTTTTTGTTTACAAAAG
AAAAACTGAAACAACTTACGGGAGGGCATAAAAAACGGGAGGAGCTCGAT
CGCCACGTATCGGCTGGAACGTTGTGAGTTCGATTCCTCTTGCAAGTATA
TTTTTTCTTCCTAGTATTGTACTGGAGCTGGGCCGAGCTGGCCAATGGAT
AGCCTGCAGGCCCAAGTACCTCCTCGCTCGCATTGCACTGCTGGGCCAAG
CTGGCCAACAGACAGCCTGACGAACATGCTATTAGTACCACCTCGTTTAT
ATTACGGTTTTATCCATACAAATTGTAAAGCGTATTATGACATTAGAAG
AAAGCGTATTGTGACGGTGAACCCGACAAAGTCAATCCGTGCTTTATTAT
TATTATTATTATTATAGGGAGGGATATGTCTCACCATGTTTTTAGGA
ATAGCTAGTTATTGAAGATAAGGCTAAGAGATGATCCATTGTATACACTT
TTTTTGTCATCTTTAAATCACATGCAAAATTTAAGATAAGACTACCTTA
TCGACCATTGTACATGCCCTAACTTATAGTTAAGTACGAAGTACACGTAC
ACAAGTTYGTCTTGCTATATCGGTTGTGTTTTGTGCGTTAGTGCTGATTA
AATACATGACAAACTGCATTGCTTGTTAACTTGCACGCTAGCACTAAGTA
TACCTACGCATRTAGATCTAGAGTGCTCCATACGCTGGTGCCTTTCACAC
TTAATGACAATCAAATGCATGACAGTTGCCCTGCATTTTGCCTTGTGCGC
TAGCACTACGCACACGTTGAAGGATCTAGAGTGCTTCATAGGCGATGGTT
TGCACGTTACCCTAATGAGATATCTATCAAACCATTCCCTTCTCATTTGT
GTTGGTCTCCATCTGTCATCGGCACCARGCAAACCTACGGAACTATAAAT
TAACAGTTTTGCTAGAACTCATCTAGCTGAGTTTTAGTTATGTCTCATTC
ACTTTTATAACCATTGGATATGATGCTATAAGATGCGTGTGTGCTGATGT
GGGTTGATACTTCTCTTCTATCTGTTTTGTCTTCCAGATGAATGAGACTA
AATTATATCTCATCTAAATGAGTTCTAGGTACTCCCATAAATTAACACGG
CCTGAGGTGAGTCCACACCACAACAAACTACACAGGCAAAGTGATATCCA
TAAATTGACCTGAAGGGCGACCTGTAAGCCCGCCATG

>SEQ ID NO:11   (tag-A)
CATGTTGTTCCGTGTAGTACC

>SEQ ID NO:19   (NW1)
AGGTGGCCGGCGTCAACGGTGCCATGA

>SEQ ID NO:20   (NW2)
GGCTAGCACCATGATGGTAGCAACAC

>SEQ ID NO:21   (NWPFor)
CCGTCACAAGATTTACAGGGTTG

>SEQ ID NO:22   (NWPRev)
TTATGGATCTCTTTATGTCTGTGT
```

Figure 15 cont.

```
CLUSTAL

GWseqVar3_Ba-B2B/1-1018   --------------------------------------------------------------------
GWseqVar1_Ki-K3A/1-1745   ---------------------CTGTGTGCGTAGGAAAAT------------------------------
GWseqVar1_Ba-B3A/1-1745   ---------------------CTGTGTGCGTRGGAAAAT------------------------------
GWseqVar5_Ki-K1B/1-524    --------------------------------------------------------------------
GWseqVar4_Ki-K4B/1-902    --------------------------------------------------------------------
GWseqVar4_Ba-B2A/1-2160   AACATGGTTATTTATTTCTGTCAAATTGTCAAATTGTAATCTGAATAATATGATGCTACC
GWseqVar6_Ba-B1A/1-473    --------------------------------------------------------------------
GWseqVar2_Ki-K2A/1-721    --------------------------------------------------------------------
GWseqVar2_Ba-B4A/1-1287   --------------------------------------------------------------------

GWseqVar3_Ba-B2B/1-1018   -TAARGCTTTTAATTTATTCCACCGTCACAAGATTTACAGGGTTGAAAACAAGATCTCCG
GWseqVar1_Ki-K3A/1-1745   -AAGTGGCCTTGCTGCACTGGGCCTCAACGCCCGGGCCAGGTACGAAATCTGGACAACCC
GWseqVar1_Ba-B3A/1-1745   -AAGTGGCCTTGCTGCACTGGGCCTCAACGCCCGGGCCAGGTACGAAATCTGGACAACCC
GWseqVar5_Ki-K1B/1-524    ----------------------------------------CGCACCGACTGTGG--------
GWseqVar4_Ki-K4B/1-902    --------------------------------------------------------------------
GWseqVar4_Ba-B2A/1-2160   AAAARGGTCCCACTTYAATAGAACCYGACAACTGGGACCCATCTGA---CTAGTGGACCC
GWseqVar6_Ba-B1A/1-473    -------------------------------GGGGCAGG---------------------
GWseqVar2_Ki-K2A/1-721    --------------------------------------------------------------------
GWseqVar2_Ba-B4A/1-1287   --------CCTACCCTAGTTGAGAAGTTTTTTTGATCCA----TTGAAAGCTG----AGAC GWseqVar3_Ba-B2B/1-1018   GGCTGTCCT------AAACCAAGCATGGCGGTCAGTAC-------------CCAGCGT
GWseqVar1_Ki-K3A/1-1745   GTTTTTTTT-CTTGCACACGAAATCACAAATTAGTA------------------CCA----
GWseqVar1_Ba-B3A/1-1745   GTTTTTTTTTCTTGCACACGAAATCACAAATTAGTA------------------CCA----
GWseqVar5_Ki-K1B/1-524    GTTTT-------------------------------------------------------------
GWseqVar4_Ki-K4B/1-902    --------------------------------------------------------------------
GWseqVar4_Ba-B2A/1-2160   ---TTCTTTTGGAAAAAAAGAAAAACTAAATTCATTTAGACAAAACRAAAAGGCCA----
GWseqVar6_Ba-B1A/1-473    --------------------------------------------------------------------
GWseqVar2_Ki-K2A/1-721    --------------------------------------------------------------------
GWseqVar2_Ba-B4A/1-1287   GTGTCT-----------ACTGACCCATAA-------------------GGCCCA----

GWseqVar3_Ba-B2B/1-1018   TAAAGTGTGCTTTGCAAAGAAGCACA--------ATGTTTTGTTCCAAGGATGC--------
GWseqVar1_Ki-K3A/1-1745   ---------CCTCGGATAAAAGAAAA--------ATCTTTTCATTGGTGAATGGAT-----
GWseqVar1_Ba-B3A/1-1745   ---------CCTCGGATAAAAGAAAA--------ATCTTTTCATTGGTGAATGGAT-----
GWseqVar5_Ki-K1B/1-524    --------------------------------------------------------------------
GWseqVar4_Ki-K4B/1-902    --------------------------------------------------------------------
GWseqVar4_Ba-B2A/1-2160   ---------CAACCCAACAATAAAAAGGCTGCAATATTGGACTGGCCCATGAACCCAAC
GWseqVar6_Ba-B1A/1-473    -------------------------------------GGAGAGGGG--------------
GWseqVar2_Ki-K2A/1-721    --------------------------------------------------------------------
GWseqVar2_Ba-B4A/1-1287   ----------GCCGGACGACAG-----------GTTTTTTGTTTACAAAA---------

GWseqVar3_Ba-B2B/1-1018   ----------------GAACATGGC---------------------------------
GWseqVar1_Ki-K3A/1-1745   ----------------GAAAAAAGC---------------------------------GGA
GWseqVar1_Ba-B3A/1-1745   ----------------GAAAAAAGC---------------------------------GGA
GWseqVar5_Ki-K1B/1-524    --------------------------------------------------------------------
GWseqVar4_Ki-K4B/1-902    --------------------------------------------------------------------
GWseqVar4_Ba-B2A/1-2160   CAAAAATYGACAGACAGAAAAAAACACRAATAGGCTGAATTGTTRCGCTAGGCCCATGTA
GWseqVar6_Ba-B1A/1-473    ---------------GGAGGC--------------------------------GCA
GWseqVar2_Ki-K2A/1-721    --------------------------------------------------------------------
GWseqVar2_Ba-B4A/1-1287   ---------------AGAAAAA------------------------------------

GWseqVar3_Ba-B2B/1-1018   ---------------ACCAGCCGT---------------------------------
GWseqVar1_Ki-K3A/1-1745   GAAACGC--------ACCTTGCTTTAT------------------------------
GWseqVar1_Ba-B3A/1-1745   GAAACGC--------ACCTTGCTTTAT------------------------------
GWseqVar5_Ki-K1B/1-524    --------------------------------------------------------------------
GWseqVar4_Ki-K4B/1-902    --------------------------------------------------------------------
GWseqVar4_Ba-B2A/1-2160   GAAAATCGAATTGGACCGGGCTGAATCTTCTGCCACATCAGATTGCCACGCTAGAYGCCT
GWseqVar6_Ba-B1A/1-473    G--------------CCTTGCCT----------------------------------
GWseqVar2_Ki-K2A/1-721    --------------------------------------------------------------------
GWseqVar2_Ba-B4A/1-1287   --------------------------------------------------------------------
```

Figure 16

```
GWseqVar3_Ba-B2B/1-1018    ------------------------------------------------------------
GWseqVar1_Ki-K3A/1-1745    ---------------------------------------TAGTA----------------
GWseqVar1_Ba-B3A/1-1745    ---------------------------------------YAGTA----------------
GWseqVar5_Ki-K1B/1-524     ------------------------------------------------------------
GWseqVar4_Ki-K4B/1-902     ------------------------------------------------------------
GWseqVar4_Ba-B2A/1-2160    ACGTGGCCTGGGGAGGTTGCTAGTGACCAAAACGCCATAGTAGACGTATTTTGGTCATAA
GWseqVar6_Ba-B1A/1-473     ------------------------------------------------------------
GWseqVar2_Ki-K2A/1-721     ------------------------------------------------------------
GWseqVar2_Ba-B4A/1-1287    ------------------------------------------------------------

GWseqVar3_Ba-B2B/1-1018    -----CTGTCTCCGCCC-------------------ATTCTG---CATCCTCC--------
GWseqVar1_Ki-K3A/1-1745    -----CTCCCTCCGTT------------TCTTTATAGTCTG---CATATAACA--------
GWseqVar1_Ba-B3A/1-1745    -----CTCCCTCCGTT------------TCTTTTTAGTCTG---CATATAACA--------
GWseqVar5_Ki-K1B/1-524     -----CTCCCTC-------------------------------------------------
GWseqVar4_Ki-K4B/1-902     ------------------------------------------------------------
GWseqVar4_Ba-B2A/1-2160    ACATCTTCGACCATTCCAAAAGAAAGGTCGCTATAGTCAG---TTTATGACGGCCAGCTT
GWseqVar6_Ba-B1A/1-473     -----CTTCCTCC------------------------------------------------
GWseqVar2_Ki-K2A/1-721     ------------------------------------------------------------
GWseqVar2_Ba-B4A/1-1287    ---------------------------------CTGAAACAACTTAC-------------

GWseqVar3_Ba-B2B/1-1018    ------------------TGCTCTA---------CTTACTTTACACTTACAGTACAAGCAGGT-
GWseqVar1_Ki-K3A/1-1745    ----------------TTTGGTCAAA-----GTCAAAGTTT----GTAAAGTTTGACCAACT-
GWseqVar1_Ba-B3A/1-1745    ----------------TTTGGTCAAA-----GTCAAAGTTT----GTAAAGTTTGACCAACT-
GWseqVar5_Ki-K1B/1-524     ----------------------GCCAAT-----GTC---------------------GACC-----
GWseqVar4_Ki-K4B/1-902     ------------------------------------------------------------
GWseqVar4_Ba-B2A/1-2160    TTGACCTTATGTTTTTTGTCATAAAAAGGTCACAAATG----GAAATTTGTGACCATTCA
GWseqVar6_Ba-B1A/1-473     ------------------------------------------------------------
GWseqVar2_Ki-K2A/1-721     ------------------------------------------------------------
GWseqVar2_Ba-B4A/1-1287    --------------GGGAGGGCATA--------------------AAAAACGGGAGGAGCT- GWseqVar3_Ba-B2B/1-1018    ------------------------------------------------------------
GWseqVar1_Ki-K3A/1-1745    ---------------------------------TTGTAGAAAAA----------------
GWseqVar1_Ba-B3A/1-1745    ---------------------------------TTGTAGAAAAR----------------
GWseqVar5_Ki-K1B/1-524     ------------------------------------------------------------
GWseqVar4_Ki-K4B/1-902     ------------------------------------------------------------
GWseqVar4_Ba-B2A/1-2160    GTGACCAATAATGGTGGTCATAAGTTGACATATTTCTTGTAGTGAAAGTGGTCGCCCGCC
GWseqVar6_Ba-B1A/1-473     ------------------------------------------------------------
GWseqVar2_Ki-K2A/1-721     ------------------------------------------------------------
GWseqVar2_Ba-B4A/1-1287    ------------------------------------------------------------

GWseqVar3_Ba-B2B/1-1018    ----------------ATGTCACCTTATTTATTGAAAA----------------------
GWseqVar1_Ki-K3A/1-1745    ----------------AATATCAACATCTACAATAATAAAGCT-----------------
GWseqVar1_Ba-B3A/1-1745    ----------------AATATCAACATCTACAATAATAAAGCT-----------------
GWseqVar5_Ki-K1B/1-524     ------------------------------------------------------------
GWseqVar4_Ki-K4B/1-902     ------------------------------------------------------------
GWseqVar4_Ba-B2A/1-2160    TCCGTTGAGTGCACGACACTCTACTACTAAACTGAGTAAGTTCCTCTTTATTACTGTATG
GWseqVar6_Ba-B1A/1-473     ------------------------------------------------------------
GWseqVar2_Ki-K2A/1-721     ------------------------------------------------------------
GWseqVar2_Ba-B4A/1-1287    --------------CGATCGCCACGTAT--------------------------------

GWseqVar3_Ba-B2B/1-1018    -------------------------------TTTGA------------------------
GWseqVar1_Ki-K3A/1-1745    --------------------------ATATGGTTTGAA--------AATT----------
GWseqVar1_Ba-B3A/1-1745    --------------------------ATATGGTTTGAA--------AATT----------
GWseqVar5_Ki-K1B/1-524     ------------------------------------------------------------
GWseqVar4_Ki-K4B/1-902     ------------------------------------------------------------
GWseqVar4_Ba-B2A/1-2160    CACGCCTGTCCATKTGTTAAAGAACAAATACGGATTTATGTCCTATGAATTGACCCATAC
GWseqVar6_Ba-B1A/1-473     ------------------------------------------------------------
GWseqVar2_Ki-K2A/1-721     ------------------------------------------------------------
GWseqVar2_Ba-B4A/1-1287    ------------------------------------------------------------
```

Figure 16 cont.

```
GWseqVar3_Ba-B2B/1-1018    ------------------------------------------------CCTC-----ATATCACT
GWseqVar1_Ki-K3A/1-1745    --------------------------AATTTCATGA----------TGCATCTAAAAATATTGAT
GWseqVar1_Ba-B3A/1-1745    --------------------------AATTTCATGA----------TGCATCTAAAAATATTGAT
GWseqVar5_Ki-K1B/1-524     ----------------------------------------------GCGTCTACGCA--------
GWseqVar4_Ki-K4B/1-902     ------------------------------------------------------------------
GWseqVar4_Ba-B2A/1-2160    ATTGGTCTCAATAGAAACAAGAAATTTATGGAGTACGGATGTGTATGTGTAACTATGAGT
GWseqVar6_Ba-B1A/1-473     ------------------------------------------------------------------
GWseqVar2_Ki-K2A/1-721     ------------------------------------------------------------------
GWseqVar2_Ba-B4A/1-1287    ------------------------------------------------CGGCTGGA---------

GWseqVar3_Ba-B2B/1-1018    CTCAATTACAGGGGCT-------------------------------------------------
GWseqVar1_Ki-K3A/1-1745    TTCATTTTGTGAATCT-----------------TGATATTT------------------------
GWseqVar1_Ba-B3A/1-1745    TTCATTTTGTGAATCT-----------------TGATATTT------------------------
GWseqVar5_Ki-K1B/1-524     ----------GAACAT------------------TG-----------------------------
GWseqVar4_Ki-K4B/1-902     ------------------------------------------------------------------
GWseqVar4_Ba-B2A/1-2160    CTTATGGTGTGAAGCTATCTGGACTATGCACGATGATGGTGAGAGCAGACGGCTAGGCTG
GWseqVar6_Ba-B1A/1-473     ------------------------------------------------------------------
GWseqVar2_Ki-K2A/1-721     ------------------------------------------------------------------
GWseqVar2_Ba-B4A/1-1287    ----ACGTTGTGA----------------------------------------------------

GWseqVar3_Ba-B2B/1-1018    ------------------------------------------------------------------
GWseqVar1_Ki-K3A/1-1745    ------------------------------------------------------------------
GWseqVar1_Ba-B3A/1-1745    ------------------------------------------------------------------
GWseqVar5_Ki-K1B/1-524     ------------------------------------------------------------------
GWseqVar4_Ki-K4B/1-902     ------------------------------------------------------------------
GWseqVar4_Ba-B2A/1-2160    TCGGCATATCTCTGCCATGTGGCGTCTCCTGGTCGTGCAGCACTTGATGGCGGCGCCATC
GWseqVar6_Ba-B1A/1-473     ------------------------------------------------------------------
GWseqVar2_Ki-K2A/1-721     ------------------------------------------------------------------
GWseqVar2_Ba-B4A/1-1287    ------------------------------------------------------------------

GWseqVar3_Ba-B2B/1-1018    ------------------------------------------------------------------
GWseqVar1_Ki-K3A/1-1745    ------------------------------------------------------------------
GWseqVar1_Ba-B3A/1-1745    ------------------------------------------------------------------
GWseqVar5_Ki-K1B/1-524     ------------------------------------------------------------------
GWseqVar4_Ki-K4B/1-902     ------------------------------------------------------------------
GWseqVar4_Ba-B2A/1-2160    AGCCACCGTTAGGTGTCGAACTTTGTCGACGGCCTGAGCCGTCGGCATAGCTATATGGAC
GWseqVar6_Ba-B1A/1-473     ------------------------------------------------------------------
GWseqVar2_Ki-K2A/1-721     ------------------------------------------------------------------
GWseqVar2_Ba-B4A/1-1287    ------------------------------------------------------------------

GWseqVar3_Ba-B2B/1-1018    ------------------------------------------------------------------
GWseqVar1_Ki-K3A/1-1745    --------------------------------TTTTCTAT-------------------------
GWseqVar1_Ba-B3A/1-1745    --------------------------------TTTTCTAT-------------------------
GWseqVar5_Ki-K1B/1-524     ------------------------------------------------------------------
GWseqVar4_Ki-K4B/1-902     ------------------------------------------------------------------
GWseqVar4_Ba-B2A/1-2160    GCCGTCGGGAAAGCATCTATGCCGACGGGCTTTTTATGCTGAGCKGCATYCCTCGCAGA
GWseqVar6_Ba-B1A/1-473     ------------------------------------------------------------------
GWseqVar2_Ki-K2A/1-721     ------------------------------------------------------------------
GWseqVar2_Ba-B4A/1-1287    ------------------------------------------------------------------

GWseqVar3_Ba-B2B/1-1018    ------------------------------------------------------------------
GWseqVar1_Ki-K3A/1-1745    -------------AAACCTA------------------------------GTCAAAG--
GWseqVar1_Ba-B3A/1-1745    -------------AAACCTA------------------------------GTCAAAG--
GWseqVar5_Ki-K1B/1-524     ------------------------------------------------------------------
GWseqVar4_Ki-K4B/1-902     ------------------------------------------------------------------
GWseqVar4_Ba-B2A/1-2160    GTGATGRCGCCCCAAACGTATATTGTTGCGGAGCGGCCTTACACCGACGGGGTCATCGGC
GWseqVar6_Ba-B1A/1-473     ------------------------------------------------------------------
GWseqVar2_Ki-K2A/1-721     ------------------------------------------------------------------
GWseqVar2_Ba-B4A/1-1287    ------------------------------------------------------------------
```

Figure 16 cont.

```
GWseqVar3_Ba-B2B/1-1018    ------------------------------------------------------------
GWseqVar1_Ki-K3A/1-1745    -TTAAC------------------------------------------------------
GWseqVar1_Ba-B3A/1-1745    -TTAAC------------------------------------------------------
GWseqVar5_Ki-K1B/1-524     ------------------------------------------------------------
GWseqVar4_Ki-K4B/1-902     ------------------------------------------------------------
GWseqVar4_Ba-B2A/1-2160    ATTAGCCTGTCGKTCACAGGAATTCTGGCTATTCGACGCCTGGGCGTCAGCATAGAGGTT
GWseqVar6_Ba-B1A/1-473     ------------------------------------------------------------
GWseqVar2_Ki-K2A/1-721     ------------------------------------------------------------
GWseqVar2_Ba-B4A/1-1287    ------------------------------------------------------------

GWseqVar3_Ba-B2B/1-1018    ---------------------------------------GGCGAATAATAAAA--CA
GWseqVar1_Ki-K3A/1-1745    -------------------------------AAAGTTTGACTTTGCCCAAACCTTATATGCA
GWseqVar1_Ba-B3A/1-1745    -------------------------------AAAGTTTGACTTTGCCCAAACCTTATATGCA
GWseqVar5_Ki-K1B/1-524     --------------------------------TTCCCTTCCCCCA---------------
GWseqVar4_Ki-K4B/1-902     ------------------------------------------------------------
GWseqVar4_Ba-B2A/1-2160    ATTATGGTAGTGATGAACCCTGCTGGGCGAAAGTTTCATTCAGCCAATAGCATG-GTCCT
GWseqVar6_Ba-B1A/1-473     ------------------------------------------------------------
GWseqVar2_Ki-K2A/1-721     ------------------------------------------------------------
GWseqVar2_Ba-B4A/1-1287    ---------------------------------------GTTCGATTCCT--------

GWseqVar3_Ba-B2B/1-1018    AACTAAA-----------------GGAAGGATATGG------------------------
GWseqVar1_Ki-K3A/1-1745    AACTAAAAAGAA---------ACGGAGGGAGTAGG------------------------
GWseqVar1_Ba-B3A/1-1745    AACTAAAAAGAA---------ACGGAGGGAGTAGG------------------------
GWseqVar5_Ki-K1B/1-524     ------------------------------------------------------------
GWseqVar4_Ki-K4B/1-902     ------------------------------------------------------------
GWseqVar4_Ba-B2A/1-2160    AACTAAAAAGAAGGATTTGTTATCTAGGGAGGATGGGATTGTTTTATTGGGATTTTAATC
GWseqVar6_Ba-B1A/1-473     ------AAGGAA------------------------------------------------
GWseqVar2_Ki-K2A/1-721     ------------------------------------------------------------
GWseqVar2_Ba-B4A/1-1287    --CTTGCAAG--------------------------------------------------

GWseqVar3_Ba-B2B/1-1018    -------------------------------------------ATTATGGGAAGCCA
GWseqVar1_Ki-K3A/1-1745    ---------------------------------TATAG------AATTATATTAGAACG
GWseqVar1_Ba-B3A/1-1745    ---------------------------------TATAG------AATTATATTAGAACG
GWseqVar5_Ki-K1B/1-524     ------------------------------------------------------------
GWseqVar4_Ki-K4B/1-902     -----------------------------CCTCAAGTGTATAGGATCTAAATTATATTAGATCA
GWseqVar4_Ba-B2A/1-2160    GGTTTGAAATTGATTCCAATTTAGGCCTCAAGTGTATAGGATCTAAATTATATTAGATCR
GWseqVar6_Ba-B1A/1-473     ------------------------------------------------------------
GWseqVar2_Ki-K2A/1-721     ------------------------------------------------------------
GWseqVar2_Ba-B4A/1-1287    ---------------------------------TATA-------TTTTTCTTCCTAGT GWseqVar3_Ba-B2B/1-1018    TGTGTAAG----ATCAATGGAGTG-GA-G-----GGCTAAAC---------AAGGAAAGTACAC
GWseqVar1_Ki-K3A/1-1745    GTTGACCGCAAATACTTGCGCTGCGA-GACCCGTCCATACCTGCTGAAAAGAATGAAGAT
GWseqVar1_Ba-B3A/1-1745    GTTGACCGCAAATACTTGCGCTGCGA-GACCCGTCCATACCTGCTGAAAAGAATGAAGAT
GWseqVar5_Ki-K1B/1-524     --------------------GCTGCGG-GATCAGGC------------------------
GWseqVar4_Ki-K4B/1-902     GTTGACCGCAAATACATGCGTTGCGA-CACCCGTCCATACCTGCTGAAAAGAATGAAGAT
GWseqVar4_Ba-B2A/1-2160    GTTGACCGCAAATACATGCGTTGCGA-CACCCGTCCATACCTGCTGAAAAGAATGAAGAT
GWseqVar6_Ba-B1A/1-473     -----------------GGGGTGCG----------------GCTAAGAGG---------
GWseqVar2_Ki-K2A/1-721     ------------------------------------------------------------
GWseqVar2_Ba-B4A/1-1287    ATTG--------TACTGGAGCTGGGCCGAGCTGGCCA-------ATGGATAGCCTGCA---

GWseqVar3_Ba-B2B/1-1018    TTCGG---ATTTCGA--ATCACTCC----------------------------CAG
GWseqVar1_Ki-K3A/1-1745    GTGGAGGAATTTAGATCATCAATCCGATTGAAGGTAAGGTAGAAAGCATGGACCCCACAG
GWseqVar1_Ba-B3A/1-1745    GTGGAGGAATTTAGATCATCAATCCGATTGAAGGTAAGGTAGAAAGCATGGACCCCACAG
GWseqVar5_Ki-K1B/1-524     ------------------------------------------------------------
GWseqVar4_Ki-K4B/1-902     GTGGAGGAATTTAGATCATCAATCCGGTTG-----AAGGTAGAAAGCGTCGACCCCACAG
GWseqVar4_Ba-B2A/1-2160    GTGGAGGAATTTAGATCATCAATCCGGTTG-----AAGGTAGAAAGCGTCGACCCCACAG
GWseqVar6_Ba-B1A/1-473     GGGGAGGAGT------------------------------CCATCCTCCCCAAGG
GWseqVar2_Ki-K2A/1-721     ------------------------------------------------------------
GWseqVar2_Ba-B4A/1-1287    ---GGCCCAAGTACCTCCTCGCTCGCATTGCACTGCTGGGCCAAGCTGGCCAACAGACAG
```

Figure 16 cont.

```
GWseqVar3_Ba-B2B/1-1018   CTAATTCTG-TTTTC--TCGGGGA-AGCAACCTGTTCTAGATTTGGA-ATCACTCCCAAC
GWseqVar1_Ki-K3A/1-1745   CTCAATCTG-CTAACCGTCTAGGC-TACAAGCTAGTGTAACTCTGCATATCCCTGTTAGC
GWseqVar1_Ba-B3A/1-1745   CTCAATCTG-CTAACCGTCTAGGC-TACAAGCTAGTGTAACTCTGCATATCCCTGTTAGC
GWseqVar5_Ki-K1B/1-524    ----------------CCGTC---------------------------------------
GWseqVar4_Ki-K4B/1-902    CTCAATCTG-CTAACCGTCTAGGC-TACAAGCTAGTGTAACTCT-CATATCCCTGTTAAC
GWseqVar4_Ba-B2A/1-2160   CTCAATCTG-CTAACCGTCTAGGC-TACAAGCTAGTGTAACTCT-CATATCCCTGTTAAC
GWseqVar6_Ba-B1A/1-473    C--------------ACCTCGGAGG-----------------------TGCCTTCCCCTTTTAGG
GWseqVar2_Ki-K2A/1-721    ------------------------------------------------------------
GWseqVar2_Ba-B4A/1-1287   C------CTGACGAACATGCTATTAGTACCACCTCGTTTA--------TATTACGGTTTTATC GWseqVar3_Ba-B2B/1-1018   CAATCTTCTTATTGGGGA-AACAATTTGTGCCAGAT---TTGGAATCACTCCCAACTAAT
GWseqVar1_Ki-K3A/1-1745   CATGTAACTTCAAGGGGCCAATGATCGAAGTAAGATCAATGGTCTTCCTTACCTGCCATT
GWseqVar1_Ba-B3A/1-1745   CATGTAACTTCAAGGGGCCAATGATCGAAGTAAGATCAATGGTCTTCCTTACCTGCCATT
GWseqVar5_Ki-K1B/1-524    ------------------------------GTTCTATGCT--------------------
GWseqVar4_Ki-K4B/1-902    CATGTAACTTCAAGGGACCAATGATCGAAGTAAGATCAATGGTCTTCCTTACCTGTCATT
GWseqVar4_Ba-B2A/1-2160   CATGTAACTTCAAGGGACCAATGATCGAAGTAAGATCAATGGTCTTCCWTACCTGTCATT
GWseqVar6_Ba-B1A/1-473    ACTCTTCCCTCTAGGG-----------------------------------TTCCCTA
GWseqVar2_Ki-K2A/1-721    ------------------------------------------------------------
GWseqVar2_Ba-B4A/1-1287   CATACAAAATTGTAAAAGCGTATTATGACATTAGAAGAAAGCGTATT------GTGACGGT GWseqVar3_Ba-B2B/1-1018   TCTGTTTTCCAGGGGAAACAATTAATCCACGCCACCTAAACA-TGAGTAAAGTACGAAGT
GWseqVar1_Ki-K3A/1-1745   AACGCATAACAGAACAAACTGTCTGTCAACAGGACTGATATT-TGGTTTTTGTCCGCTCA
GWseqVar1_Ba-B3A/1-1745   AACGCATAACAGAACAAACTGTCTGTCAACAGGACTGATATT-TGGTTTTTGTCCGCTCA
GWseqVar5_Ki-K1B/1-524    -----------------------TGTGAAGAG--------------------------A
GWseqVar4_Ki-K4B/1-902    AACGCATACCAGAACAAACTGTCTGTCGACAGGACTGATATT-TTGTTTTTGTCCGCTCA
GWseqVar4_Ba-B2A/1-2160   AACGCATACCAGAACAAACTGTCYGTCGACAGGACTGATATT-TTGTTTTTGTCCGCTYA
GWseqVar6_Ba-B1A/1-473    GGCGCAT------------------GGGCCTC----T-TGGGGCTGGTGCCCTTG
GWseqVar2_Ki-K2A/1-721    ------------------------------------------------------------
GWseqVar2_Ba-B4A/1-1287   GAACCCGACAAAGTCAATCCGTGCTTTATTATTATTATTATTATTATAGGGAGGGAT GWseqVar3_Ba-B2B/1-1018   ACACGTACTCAAGT--------------------CTATCTCGCT--------ATATCG
GWseqVar1_Ki-K3A/1-1745   ACAACTTTACATGTAGACATTA-------ATCATCTACTAGCTCACTCAGAATTAGAACG
GWseqVar1_Ba-B3A/1-1745   ACAACTTTACATGTAGACATTA-------ATCATCTACTAGCTCACTCAGAATTAGAACG
GWseqVar5_Ki-K1B/1-524    GCAAC-------------------------------------------------------
GWseqVar4_Ki-K4B/1-902    ACAACTTTACATGTAGACACTAGACACTAATCATCTACTAGCTCACTCAGAATTAGAACG
GWseqVar4_Ba-B2A/1-2160   ACAACTTTACATGTAGACACTARACACTAATCATCTACTAGCTCACTCAGAATTAGAACG
GWseqVar6_Ba-B1A/1-473    GC------CCATGTAGGC-----------------CAAGGCGCACCCC-----TACAGCC
GWseqVar2_Ki-K2A/1-721    ------------------------------------------------------------
GWseqVar2_Ba-B4A/1-1287   ATGTCTCACCATGTTTTTAGGAATAGCTAGTTATTGAAGATAAGGCTAAGAGAT-GATCC GWseqVar3_Ba-B2B/1-1018   GTGG------GTGTTTTG-TG--------------------CGTTAGT---------------
GWseqVar1_Ki-K3A/1-1745   ATTG-----AGATTTTGCTG-------------------AGAAGGTGAGACTAGACGGGC
GWseqVar1_Ba-B3A/1-1745   ATTG-----AGATTTTGCTG-------------------AGAAGGTGAGACTAGAC-GGC
GWseqVar5_Ki-K1B/1-524    ------------------------------------------------------------
GWseqVar4_Ki-K4B/1-902    ATTG-----AGATTTTGCTG-------------------AGAAGGTGGGACTAGAC-GGC
GWseqVar4_Ba-B2A/1-2160   ATTG-----AGATTTTGCTG-------------------AGAAGGTGGGACTAGAC-GGC
GWseqVar6_Ba-B1A/1-473    CATG-----TGGCCCCCCGG--------------------GGCAGGTG---------------
GWseqVar2_Ki-K2A/1-721    ---------------------------AATCACATGCAAAATTTAAGATAAGACTACC
GWseqVar2_Ba-B4A/1-1287   ATTGTATACACTTTTTTTTGTCATCTTTAAATCACATGCAAAATTTAAGATAAGACTACC GWseqVar3_Ba-B2B/1-1018   -----ACCATGTAA--------------AAAATAAATAGATGAC-AAACTGCATTG-----
GWseqVar1_Ki-K3A/1-1745   TTCTAAGCAGGTAGGATTC-ACAAGCTCAAACCGCTGAGCTAAA-ACTATGCATTTGGAA
GWseqVar1_Ba-B3A/1-1745   TTCTAAGCAGGTAGGATTC-ACAAGCTCAAACCGCTGAGCTAAA-ACTATGCATTTGGAA
GWseqVar5_Ki-K1B/1-524    --CTAAGCAAGCAGGCTT------------------------------------------
GWseqVar4_Ki-K4B/1-902    TTCTAAGCAGGTAGGATTC-ACAAGCTCAAACCACTGAGCTAAA-ACTATGCATTTGGAA
GWseqVar4_Ba-B2A/1-2160   TTCTAAGCAGGTAGGATTC-ACAAGCTCAAACCACTGAGCTAAA-ACTATGCATTTGGAA
GWseqVar6_Ba-B1A/1-473    ----------------------GCCCCACCCGTGGGC-----------------------
GWseqVar2_Ki-K2A/1-721    TT------ATCGACCATTGTACATGCCCTAACTTAT-AGTTAAGTACGAAGTACACGTAC
GWseqVar2_Ba-B4A/1-1287   TT------ATCGACCATTGTACATGCCCTAACTTAT-AGTTAAGTACGAAGTACACGTAC
```

Figure 16 cont.

```
GWseqVar3_Ba-B2B/1-1018    -------CTCGTTA---------ACTTGCACGCT-------------------------
GWseqVar1_Ki-K3A/1-1745    ACACTCCCACCTAA----------TTTTGTTTTTTCGGG--------GAAACAATCTACGCC
GWseqVar1_Ba-B3A/1-1745    ACACTCCCACCTAA----------TTTTGTTTTTTCGGG--------GAAACAATCTACGCC
GWseqVar5_Ki-K1B/1-524     ------------------------------------------------------------
GWseqVar4_Ki-K4B/1-902     ACACTCCCACCTAA----------TTTTGTTTTCTCAGG--------GAAACAATCTACGCC
GWseqVar4_Ba-B2A/1-2160    ACACTCCCACCTAA----------TTTTGTTTTCTCAGG--------GAAACAATCTACGCC
GWseqVar6_Ba-B1A/1-473     --------------------------CCCCGG--------GA------------------
GWseqVar2_Ki-K2A/1-721     ACAAGTTTGTCTTGCTATATCGGTTGTGTTTTGTGCGTTAGTGCTGATTAAATACATGAC
GWseqVar2_Ba-B4A/1-1287    ACAAGTTYGTCTTGCTATATCGGTTGTGTTTTGTGCGTTAGTGCTGATTAAATACATGAC GWseqVar3_Ba-B2B/1-1018    ---------------AGC---ACTAAGT---------AC---------------------
GWseqVar1_Ki-K3A/1-1745    AGATT-----TGGAGGT--ACTCCCA--------ACTAATTTTGTTTCCTTAGGAAACAATC
GWseqVar1_Ba-B3A/1-1745    AGATT-----TGGAGGT--ACTCCCA--------ACTAATTTTGTTTCCTTAGGAAACAATC
GWseqVar5_Ki-K1B/1-524     ------------------------------------------------------------
GWseqVar4_Ki-K4B/1-902     AGATTAATTTGGAAGC--ACTCCCA--------ACTAATTTTGTTT----------------
GWseqVar4_Ba-B2A/1-2160    AGATTAATTTGGAAGC--ACTCCCA--------ACTAATTTTGTTT----------------
GWseqVar6_Ba-B1A/1-473     -----------------C--CCTTCC----------------------------------
GWseqVar2_Ki-K2A/1-721     AAACTGCATTGCTTGTTAACTTGCACGCTAGCACTAAGTAT-------------------
GWseqVar2_Ba-B4A/1-1287    AAACTGCATTGCTTGTTAACTTGCACGCTAGCACTAAGTAT-------------------

GWseqVar3_Ba-B2B/1-1018    ------------------------------------ACCTACAGAGAT---------------
GWseqVar1_Ki-K3A/1-1745    TACGCCGAGCAGACAAGAAGGGAGGGATCCCGATAACTTACGGTAATGATAACTTCCGAA
GWseqVar1_Ba-B3A/1-1745    TACGCCGAGCAGACAAGAAGGGAGGRATCCCGATAACTTACGGTAATGATAACTTCCGAA
GWseqVar5_Ki-K1B/1-524     ------------------------------GTAGCTTAGGCTCCTGCTA-----------
GWseqVar4_Ki-K4B/1-902     ------------------------------------------------------------
GWseqVar4_Ba-B2A/1-2160    ------------------------------------------------------------
GWseqVar6_Ba-B1A/1-473     ------------------------------------------------------------
GWseqVar2_Ki-K2A/1-721     ------------------------------------ACCTACGCATAT---------------
GWseqVar2_Ba-B4A/1-1287    ------------------------------------ACCTACGCATRT---------------

GWseqVar3_Ba-B2B/1-1018    ---------------------------------AGATG--------TAGAGCCC-----
GWseqVar1_Ki-K3A/1-1745    CGTTCGGGAGTTAAGCAYGGCAACCCGAACGGGTTTAGATGGCAAGTTTAGTTTGCGTGA
GWseqVar1_Ba-B3A/1-1745    CGYTCGGGAGTTAAGCATGGCAACCCGAACGGGTTTAGATGGCAAGTTTAGTTTGCGTGA
GWseqVar5_Ki-K1B/1-524     --------------------------------GTGTATATATAG-------TGGTTTTC-----
GWseqVar4_Ki-K4B/1-902     ------------------------------------------------------------
GWseqVar4_Ba-B2A/1-2160    ------------------------------------------------------------
GWseqVar6_Ba-B1A/1-473     ------------------------------------------------------------
GWseqVar2_Ki-K2A/1-721     ---------------------------------AGAT--------CTAGAGTGC-----
GWseqVar2_Ba-B4A/1-1287    ---------------------------------AGAT--------CTAGAGTGC-----

GWseqVar3_Ba-B2B/1-1018    ------------------------------------------------------------
GWseqVar1_Ki-K3A/1-1745    GATTAGGGAAACATGGCAATTTTCTGCAAAAAAGAAAAAGGATAAAGTTGCCATCCCCT
GWseqVar1_Ba-B3A/1-1745    GATTAGGGAAACATGGCAATTTTCTGCAAAAAAGAAAAAGGATAAAGTTGCCATCCCCT
GWseqVar5_Ki-K1B/1-524     --------------------TTTTTCT---------------------------------
GWseqVar4_Ki-K4B/1-902     --TTAGGGAA--------------------------------------------------
GWseqVar4_Ba-B2A/1-2160    --TTAGGGAA--------------------------------------------------
GWseqVar6_Ba-B1A/1-473     ------------------------------------------------------------
GWseqVar2_Ki-K2A/1-721     ------------------------------------------------------------
GWseqVar2_Ba-B4A/1-1287    ------------------------------------------------------------

GWseqVar3_Ba-B2B/1-1018    ------------------------------------------------------------
GWseqVar1_Ki-K3A/1-1745    ATGAACTAAAGTTGCCATATAAAAACGTTCGGGACGAAACGCTCAAAATCCCAACGTTCG
GWseqVar1_Ba-B3A/1-1745    ATGAACTAAAGTTGCCATATAAAAACGTTCGGGACGRAACGCTCAAAATCCCAACGTTCG
GWseqVar5_Ki-K1B/1-524     -----------------------------------CTCAATAT-----------------
GWseqVar4_Ki-K4B/1-902     ------------------------------------------------------------
GWseqVar4_Ba-B2A/1-2160    ------------------------------------------------------------
GWseqVar6_Ba-B1A/1-473     ------------------------------------------------------------
GWseqVar2_Ki-K2A/1-721     ------------------------------------------------------------
GWseqVar2_Ba-B4A/1-1287    ------------------------------------------------------------
```

Figure 16 cont.

```
GWseqVar3_Ba-B2B/1-1018   ----------------------------------------------------------------
GWseqVar1_Ki-K3A/1-1745   GGAGTTATTGGATTCCATAACTTAAGAGTTAAGTACAAAGTACACGTTCACACATTTATC
GWseqVar1_Ba-B3A/1-1745   GGAGTTATTGGATTCCATAACTTAAGAGTTAAGTACAAAGTACACGTACACACATTTATC
GWseqVar5_Ki-K1B/1-524    -------------------------------------------------CAACCATTT---
GWseqVar4_Ki-K4B/1-902    ------------------------------------------------------------
GWseqVar4_Ba-B2A/1-2160   ------------------------------------------------------------
GWseqVar6_Ba-B1A/1-473    ------------------------------------------------------------
GWseqVar2_Ki-K2A/1-721    ------------------------------------------------------------
GWseqVar2_Ba-B4A/1-1287   ------------------------------------------------------------

GWseqVar3_Ba-B2B/1-1018   ------------------------------------------------------------
GWseqVar1_Ki-K3A/1-1745   TTGCTATATCGGTGGTGTTTTATGCGTTGGTGCCGATTAAATACATGACAAACTACGTTG
GWseqVar1_Ba-B3A/1-1745   TTGCTATATCGGTGGTGTTTTATGCGTTGGTGCCGATTAAATACATGACAAACTACGTTG
GWseqVar5_Ki-K1B/1-524    ----TATAT---------------------------------------------------
GWseqVar4_Ki-K4B/1-902    ---------------------------------------------GCAATCTACG-----
GWseqVar4_Ba-B2A/1-2160   ---------------------------------------------GCAATCTACG-----
GWseqVar6_Ba-B1A/1-473    ------------------------------------------------------------
GWseqVar2_Ki-K2A/1-721    ------------------------------------------------------------
GWseqVar2_Ba-B4A/1-1287   ------------------------------------------------------------

GWseqVar3_Ba-B2B/1-1018   -------------------------------------------------------TCCAT
GWseqVar1_Ki-K3A/1-1745   CTCGTTAACTTGCACGCTAGCACTAAGTACACCTACACAGATAGATCTAGAGCTCTCCGT
GWseqVar1_Ba-B3A/1-1745   CTCGTTAACTTGCACGCTAGCACTAAGTACACCTACACAGATAGATCTAGAGCTCTCCGT
GWseqVar5_Ki-K1B/1-524    -------------------------------------------------------TGTGT
GWseqVar4_Ki-K4B/1-902    --------------------------------------------------------CCAT
GWseqVar4_Ba-B2A/1-2160   --------------------------------------------------------CCAT
GWseqVar6_Ba-B1A/1-473    ------------------------------------------------------------
GWseqVar2_Ki-K2A/1-721    -------------------------------------------------------TCCAT
GWseqVar2_Ba-B4A/1-1287   -------------------------------------------------------TCCAT GWseqVar3_Ba-B2B/1-1018   ATG-TGGTGCCTTTTACGCTTAATGACAATGAAATGCGCGCCAGCTGCATTGCTTTTTCA
GWseqVar1_Ki-K3A/1-1745   ATG-TGGTGCTTTTTACACTTAACGGTAATCAAATGCTTGCCGGCTGCATTGCTTTTTCG
GWseqVar1_Ba-B3A/1-1745   ATG-TGGTGCTTTTTACACTTAACGGTAATCAAATGCTTGCCGGCTGCATTGCTTTTTCG
GWseqVar5_Ki-K1B/1-524    ATG-TGGTGCTTTTTACACTTAACGGTAATCAAATGCTTGCCGGCTGCATTGCTTTTTCG
GWseqVar4_Ki-K4B/1-902    ATG-TGGTGCCTTTTACACTT--ACGGTAATCAAATGCATGGCAGGTGCATTGCTTTTCCT
GWseqVar4_Ba-B2A/1-2160   ATG-TGGTGCCTTTTACACTT--ACGGTAATCAAATGCATGGCAGGTGCATTGCTTTTCCT
GWseqVar6_Ba-B1A/1-473    -GG-TGGTCCC-------------------------------------------------
GWseqVar2_Ki-K2A/1-721    ACGCTGGTGCCTTTCACACTTAATGACAATCAAATGCATGACAGTTGCCCTGCATTTTGC
GWseqVar2_Ba-B4A/1-1287   ACGCTGGTGCCTTTCACACTTAATGACAATCAAATGCATGACAGTTGCCCTGCATTTTGC GWseqVar3_Ba-B2B/1-1018   CTTGTGTGCTGCAAATATGTACACGCGAACGGATGTAGAGTATTCCATATATAGGTGGTG
GWseqVar1_Ki-K3A/1-1745   CTTGTACTCTACAACTACATACACGTATACAGACCTACAGTGCTGC----ATAGGTGGTG
GWseqVar1_Ba-B3A/1-1745   CTTGTACTCTACAACTACATACACGTATACAGACCTACAGTGCTGC----ATAGGTGGTG
GWseqVar5_Ki-K1B/1-524    CTTGTACTCTACAACTACATACACGTATACAGACCTACAGTGCTGC----ATAGGTGGTG
GWseqVar4_Ki-K4B/1-902    CTTGTACTCTACAACTACATACACGTATACAGATCTAGAGTGCTCC----ATAGGTGGTG
GWseqVar4_Ba-B2A/1-2160   CTTGTACTCTACAACTACATACACGTATACAGATCTAGAGTGCTCC----ATAGGTGGTG
GWseqVar6_Ba-B1A/1-473    ---GGTACAATAC-----------CGATGAC--CCCGAAACTTGTCC-------CGATGGCC
GWseqVar2_Ki-K2A/1-721    CTTGTGCGCTAGCACTACGCACACGTTGAAGGATCTAGAGTGCTTC----ATAGGCGATG
GWseqVar2_Ba-B4A/1-1287   CTTGTGCGCTAGCACTACGCACACGTTGAAGGATCTAGAGTGCTTC----ATAGGCGATG GWseqVar3_Ba-B2B/1-1018   GTTTGTACGTCAATACTTGTCTCATATCCGCCAAATGCATAGCTTTTCCACTTTGTTGCG
GWseqVar1_Ki-K3A/1-1745   GTTTGTACGTCAAGACTGATCTAATATCTGCCAAACGCATAGCTTTTCCACTT--ATGCC
GWseqVar1_Ba-B3A/1-1745   GTTTGTACGTCAAGACTGATCTAATATCTGCCAAACGCATAGCTTTTCCACTT--GTGCC
GWseqVar5_Ki-K1B/1-524    GTTTGTACGTCAAGACTGATCTAATATCTGCCAAACGCATAGCTTTTCCACTT--GTGCC
GWseqVar4_Ki-K4B/1-902    GTTTGTACGTCAAGACTGATCTAATATCTGCCAAATGCATAGCTTTTCCACTT--GTGCC
GWseqVar4_Ba-B2A/1-2160   GTTTGTACGTCAAGACTGATCTAATATCTGCCAAATGCATAGCTTTTCCACTT--GTGCC
GWseqVar6_Ba-B1A/1-473    G-------AAACAGGACT--TCCTATATAT---------AAATCTTTACC--------TCC
GWseqVar2_Ki-K2A/1-721    GTTTGCACGTT-ACCCTAATGAGATATCTATCAAAC-CATTCCCTTCTCATTT--GTGTT
GWseqVar2_Ba-B4A/1-1287   GTTTGCACGTT-ACCCTAATGAGATATCTATCAAAC-CATTCCCTTCTCATTT--GTGTT
```

Figure 16 cont.

```
GWseqVar3_Ba-B2B/1-1018   GGCACCAA----------------------------------------------------
GWseqVar1_Ki-K3A/1-1745   GGCATCCATCCATCATCGACGC--------------------------------------
GWseqVar1_Ba-B3A/1-1745   GGCATCCATCCATCATCGACGC--------------------------------------
GWseqVar5_Ki-K1B/1-524    GGCATCCATCCATCATCGACGC--------------------------------------
GWseqVar4_Ki-K4B/1-902    GGCATCCATCCATCGTCGACGC--------------------------------------
GWseqVar4_Ba-B2A/1-2160   GGCATCCATCCATCGTCGACGC--------------------------------------
GWseqVar6_Ba-B1A/1-473    GG--ACCATTC--------CGG--------------------------------------
GWseqVar2_Ki-K2A/1-721    GGTCTCCATCTGTCATCGGCACCAAGCAAACCTACGGAACTATAAATTAACAGTTTTGCT
GWseqVar2_Ba-B4A/1-1287   GGTCTCCATCTGTCATCGGCACCARGCAAACCTACGGAACTATAAATTAACAGTTTTGCT GWseqVar3_Ba-B2B/1-1018   ----------------------------------------AT------------------
GWseqVar1_Ki-K3A/1-1745   ---------------------------------------ATATCCAT-------------
GWseqVar1_Ba-B3A/1-1745   ---------------------------------------ATATCCAT-------------
GWseqVar5_Ki-K1B/1-524    ---------------------------------------ATATCCAT-------------
GWseqVar4_Ki-K4B/1-902    ---------------------------------------ATATCCAT-------------
GWseqVar4_Ba-B2A/1-2160   ---------------------------------------ATATCCAT-------------
GWseqVar6_Ba-B1A/1-473    ---------------------------------------AACTCC---------------
GWseqVar2_Ki-K2A/1-721    AGAACTCATCTAGCTGAGTTTTAGTTATGTCTCATTCACTTTTATAGCCATTGGATATGA
GWseqVar2_Ba-B4A/1-1287   AGAACTCATCTAGCTGAGTTTTAGTTATGTCTCATTCACTTTTATAACCATTGGATATGA GWseqVar3_Ba-B2B/1-1018   -------------------------------AGACAA-----------------------
GWseqVar1_Ki-K3A/1-1745   -------------------------------ATACAT-----------------------
GWseqVar1_Ba-B3A/1-1745   -------------------------------ATACAT-----------------------
GWseqVar5_Ki-K1B/1-524    -------------------------------ATACAT-----------------------
GWseqVar4_Ki-K4B/1-902    -------------------------------ATACAT-----------------------
GWseqVar4_Ba-B2A/1-2160   -------------------------------ATACAT-----------------------
GWseqVar6_Ba-B1A/1-473    ------------------------------------------------------------
GWseqVar2_Ki-K2A/1-721    TGCTATAAGATGCGTGTGTGCTGATGTGGGTTGATACTTCTTTTCTATCTGTTTTGTCTT
GWseqVar2_Ba-B4A/1-1287   TGCTATAAGATGCGTGTGTGCTGATGTGGGTTGATACTTCTCTTCTATCTGTTTTGTCTT GWseqVar3_Ba-B2B/1-1018   ---------ATCGGACTA-----------------------------------TAAATT
GWseqVar1_Ki-K3A/1-1745   ----------ACGG-AGTA----------------------------------TAAATT
GWseqVar1_Ba-B3A/1-1745   ----------ACGG-AGTA----------------------------------TAAATT
GWseqVar5_Ki-K1B/1-524    ----------ACGG-AGTA----------------------------------TAAATT
GWseqVar4_Ki-K4B/1-902    ----------ACGGGACTA----------------------------------TAAATT
GWseqVar4_Ba-B2A/1-2160   ----------ACGGGACTA----------------------------------TAAATT
GWseqVar6_Ba-B1A/1-473    ----------TCGTGACTA----------------------------------TAAATT
GWseqVar2_Ki-K2A/1-721    CCAGATGAATGAGACTAAATTATATCTCATCTAAATGAGTTCTAGGTACTCCCATAAATT
GWseqVar2_Ba-B4A/1-1287   CCAGATGAATGAGACTAAATTATATCTCATCTAAATGAGTTCTAGGTACTCCCATAAATT GWseqVar3_Ba-B2B/1-1018   GATACGCCCAAGGCAAAGCCCATAGAACAAGGGACTACACAGACATAAAGAGATCCATAA
GWseqVar1_Ki-K3A/1-1745   AACACGGCCCGAGGTGAGCGCACACCACAGCGGACAACACAGACATAAAGTGATCCATAA
GWseqVar1_Ba-B3A/1-1745   AACACGGCCCGAGGTGAGCGCACACCACAGCGGACAACACAGACATAAAGTGATCCATAA
GWseqVar5_Ki-K1B/1-524    AACACGGCCCGAGGTGAGCGCACACCACAGCGGACAACACAGACATAAAGTGATCCATAA
GWseqVar4_Ki-K4B/1-902    AACACGGCCCGAGGTGAGCGCACACGACAACGGACTACAAAGACATAGAGTGGTCCATAG
GWseqVar4_Ba-B2A/1-2160   AACACGGCCCGAGGTGAGCGCACACGACAACGGACTACAAAGACATAGAGTGGTCCATAG
GWseqVar6_Ba-B1A/1-473    GATACGCCCAAGGCAAAGCCCATAGAACAAGGGACTACACAGACATAAAGAGATCCATAA
GWseqVar2_Ki-K2A/1-721    AACACGGCCTGAGGTGAGTCCACACCACAACAAACTACACAGGCAAAGTGATATCCATAA
GWseqVar2_Ba-B4A/1-1287   AACACGGCCTGAGGTGAGTCCACACCACAACAAACTACACAGGCAAAGTGATATCCATAA GWseqVar3_Ba-B2B/1-1018   CTTAACCTGAAGAGTGTGACGAGATAGGCAGC---CATG
GWseqVar1_Ki-K3A/1-1745   GATAACCTGAAGAGGGTGACGGGCTAGGCAGC---CATG
GWseqVar1_Ba-B3A/1-1745   GATAACCTGAAGAGGGTGACGGGCTAGGCAGC---CATG
GWseqVar5_Ki-K1B/1-524    GATAACCTGAAGAGGGTGACGGGCTAGGCAGC---CATG
GWseqVar4_Ki-K4B/1-902    GATAACCTGAAGAGTGGCGGCGGCTAGGCAGCAGCCATG
GWseqVar4_Ba-B2A/1-2160   GATAACCTGAAGAGGGTGGCGGCGTAGGCAGCAGCCATG
GWseqVar6_Ba-B1A/1-473    CTTAACCTGAAGAGTGTGACGAGATAGGCAGC---CATG
GWseqVar2_Ki-K2A/1-721    ATTGACCTGAA--GGGCGACCTGCAAGCCCGC---CATG
GWseqVar2_Ba-B4A/1-1287   ATTGACCTGAA--GGGCGACCTGTAAGCCCGC---CATG
```

Figure 16 cont.

BREAD QUALITY PROTEIN AND METHODS OF USE

This application is the U.S. national phase of International Application No. PCT/AU2015/050835, filed Dec. 23, 2015, which designated the U.S. and claims priority to Application No. AU 2014905219, filed Dec. 23, 2014; the entire contents of each of which are hereby incorporated by reference.

TECHNICAL FIELD

The present invention relates to plants such as wheat and other cereals. More particularly, the invention relates to a wheat protein associated with improved bread making quality, and methods of use of this protein.

BACKGROUND

Wheat is a major food crop and ongoing genetic improvements in wheat productivity are critical for food security. Wheat has unique and complex qualities required for breadmaking that limit the rate of genetic gain in wheat breeding. Many proteins influencing the physical properties of wheat dough have been characterized but the key determinants of genetic variation in breadmaking quality have not been identified. Improved understanding of the molecular basis of genetic differences in breadmaking quality may allow more rapid development of high performing genotypes with acceptable end use properties and facilitate increased wheat production. Advances in molecular techniques provide new opportunities to identify the genetic and molecular basis of bread quality in wheat to enable more rapid progress in satisfying global food demand.

SUMMARY

The present invention is broadly directed to an isolated wheat protein that is highly abundant in the seed of wheat varieties with desirable breadmaking qualities. The invention is also directed to the use of said isolated wheat protein for the improvement of breadmaking qualities in plants.

In a first aspect, the invention provides an isolated protein comprising the amino acid sequence set forth in SEQ ID NO:1.

This aspect also includes fragments, variants and derivatives of said isolated protein.

In a second aspect, the invention provides an isolated nucleic acid encoding the isolated protein, fragment, variant or derivative thereof of the first aspect. Suitably, the isolated nucleic acid comprises the nucleotide sequence of any one of SEQ ID NOS:11-18 or SEQ ID NO:23.

This aspect also includes fragments, variants and derivatives of said isolated nucleic acid.

In a third aspect, the invention provides a promoter comprising any one of the nucleotide sequences set forth in SEQ ID NOS:2-9, or a promoter-active fragment thereof.

Also provided according to this aspect are promoter or promoter-active fragments comprising one or more nucleotide sequence additions, deletions and/or substitutions to any one of SEQ ID NOS:2-9 that relatively increase or elevate the activity of said promoter or promoter active fragment, wherein the nucleotide sequence of said modified promoter or promoter active fragment is not SEQ ID NO:10.

In a fourth aspect, the invention provides a method of increasing or elevating the activity of a promoter or promoter-active fragment comprising any one of the nucleotide sequences set forth in SEQ ID NOS:2-9, by introducing one or more nucleotide sequence additions, deletions and/or substitutions to any one of SEQ ID NOS:2-9 that relatively increase or elevate the activity of said promoter or promoter active fragment, wherein the nucleotide sequence of said modified promoter or promoter active fragment is not SEQ ID NO:10.

In certain embodiments of this aspect, the one or more nucleotide sequence additions, deletions and/or substitutions introduced into any one of SEQ ID NOS:2-9 are present in SEQ ID NO:10, but are not present in any of SEQ ID NO:2-9.

In a fifth aspect, the invention provides a genetic construct comprising an isolated nucleic acid according to the second aspect and/or the promoter or promoter-active fragment of the third aspect.

In a sixth aspect, the invention provides a host cell comprising the genetic construct of the fifth aspect.

In a seventh aspect, the invention provides a method of producing a genetically modified plant or plant part with relatively improved or enhanced breadmaking properties, said method including the step of genetically modifying one or more plant cells or tissues to produce a plant capable of producing a seed comprising an increased or elevated expression, activity, or amount of the protein of the first aspect, to thereby produce a plant or plant part with improved breadmaking properties.

In an eighth aspect, the invention provides a method of producing a plant or plant part with relatively improved or enhanced breadmaking properties, said method including the steps of:

(i) introducing one or more mutations into the genetic material of a plant; and (ii) selecting a plant capable of producing a seed comprising an increased or elevated expression, activity, or amount of the protein of the first aspect, to thereby produce a plant or plant part with improved breadmaking properties.

In an ninth aspect, the invention provides a method of producing a plant or plant part with relatively improved or enhanced breadmaking properties, including the steps of:

(i) identifying one or more plants capable of producing a seed comprising an increased or elevated expression, activity or amount of the protein of the first aspect;

(ii) crossing the one or more plants capable of producing a seed comprising an increased or elevated expression, activity, or amount of the protein of the first aspect together, and/or with one or more other plants; and (iii) selecting one or more progeny plants capable of producing a seed comprising an increased or elevated expression, activity or amount of the protein of the first aspect, to thereby produce a plant or plant part with improved breadmaking properties.

In a tenth aspect, the invention provides a plant or plant part with relatively improved breadmaking properties produced according to any one of the seventh, eighth or ninth aspects.

In an eleventh aspect, the invention provides a plant with improved breadmaking properties, wherein said plant has been genetically modified or mutagenized to relatively increase or elevate the expression, activity, or amount of the protein of the first aspect.

In a twelfth aspect, the invention provides a seed produced from the plant of the tenth or eleventh aspects.

Also provided are cells, tissues, leaves, fruit, flowers, and other reproductive material, material useful for vegetative propagation, progeny plants including F1 hybrids, male-sterile plants and all other plants and plant products derivable from said plants.

In a thirteenth aspect, the invention provides a plant product produced from a plant or plant part of the tenth-twelfth aspect.

Preferably, a plant of the seventh to twelfth aspects is a monocotyledonous plant or a dicotyledonous plant.

More preferably the plant is selected from the group consisting of a grass species of the Poaceae family; a cereal species including wheat, rice, barley, oats, maize, and *sorghum*; a leguminous species including beans and peanut; and a solanaceous species including tomato and potato.

Even more preferably, the plant is a cereal species selected from the group consisting of wheat, rice, barley, oats, maize, *sorghum*.

In one particular preferred embodiment, the plant is wheat.

In certain preferred embodiments of the ninth aspect wherein the plant is wheat, preferably at least one of the one or more plants capable of producing a seed comprising an increased or elevated expression, activity or concentration of the protein of the first aspect is selected from the group consisting of: Sunco, Gregory, Bob White 26, Batavia, Banks, Janz, Condor, Cook, Bounty, Baxter, Oxley, Wylie, Kidman, Hume, Chara, and Leichhardt.

In a fourteenth aspect, the invention provides a method of making bread, the method including the step of processing a seed of the twelfth aspect to thereby produce bread.

In a fifteenth aspect of the invention, there is provided an antibody or antibody fragment that binds or is raised against the isolated protein of the first aspect.

It will be appreciated that the indefinite articles "a" and "an" are not to be read as singular indefinite articles or as otherwise excluding more than one or more than a single subject to which the indefinite article refers. For example, "a" protein includes one protein, one or more proteins or a plurality of proteins.

As used herein, unless the context requires otherwise, the words "comprise", "comprises" and "comprising" will be understood to mean the inclusion of a stated integer or group of integers but not the exclusion of any other integer or group of integers.

BRIEF DESCRIPTION OF THE FIGURES

In order that the invention may be readily understood and put into practical effect, preferred embodiments will now be described by way of example with reference to the accompanying figures, wherein:

FIG. 1 sets out SEQ ID NO:1, the amino acid sequence of a wbm protein of the invention; SEQ ID NO:12, the nucleotide sequence of a wbm CDS encoding the wbm protein comprising the amino acid sequence set forth in SEQ ID NO:1; SEQ ID NO:23, the nucleotide sequence of a wbm gene comprising SEQ ID NO:12; and a translation of SEQ ID NO:12 to SEQ ID NO:1 (amino acid sequence given in three letter code for translation).

FIG. 3 sets out diagrammatic overviews of a wbm gene and wbm protein. (A) The nucleotide sequence, SEQ ID NO:23, of a wbm gene of the invention, identified from ESTs matching a transcript corresponding to tag-A set forth in SEQ ID NO: 11. An open reading frame with start and stop codons including the location of the tag is indicated. 5' UTR sequence (before the start codon) and 3' UTR sequence (after the stop codon) is indicated. (B) wbm is a small protein comprising a predicted signal peptide of 27 amino acid (aa) residues and a non-cytoplasmic domain which spans from 28 to 75 aa residues. Predicted signal peptide spanning the first 27aa of the contig based on InterProScan (EBI, www world wide web at ebi.ac.uk), incorporated herein by reference.

FIG. 6 sets out variety-specific expression of the wbm gene sequence variants, set forth in SEQ ID NOS:13-18, respectively. The relative abundance of sequence variants of the wbm gene for each genotype at 14 and 30 days post anthesis (dpa) is shown as a percentage of total normalised wbm gene expression. A and C show variety-specific expression of each of the 5' sequence variants, and B and D show variety-specific expression of each of the 3' sequence variants. Read counts were normalised with respect to total mapped reads.

FIG. 10 sets out the 1379 bp nucleotide sequence, SEQ ID NO:10, of the wbm promoter-active fragment GWSeqVar3 from wheat cv. Banks. Putative TATA and CAAT boxes, and ATAGAA, a putative region for transcription initiation, are shaded grey.

FIG. 15 sets out SEQ ID NOS:2-9, SEQ ID NO:11 and SEQ ID NOS:19-22.

FIG. 16 sets out a "CLUSTALW" alignment world wide web at ebi.ac.uk/Tools/msa/clustalw2/help/; incorporated herein by reference) of "weak" or "less active" wbm promoter-active fragments comprising nucleotide sequences set forth in SEQ ID NOS:2-9, and "active" wbm promoter-active fragment "GWSeqVar3 Ba-B2B" (referred to herein as GWSeqVar3) comprising nucleotide sequence set forth in SEQ ID NO: 10.

BRIEF DESCRIPTION OF THE SEQUENCE LISTING

Figure 2:
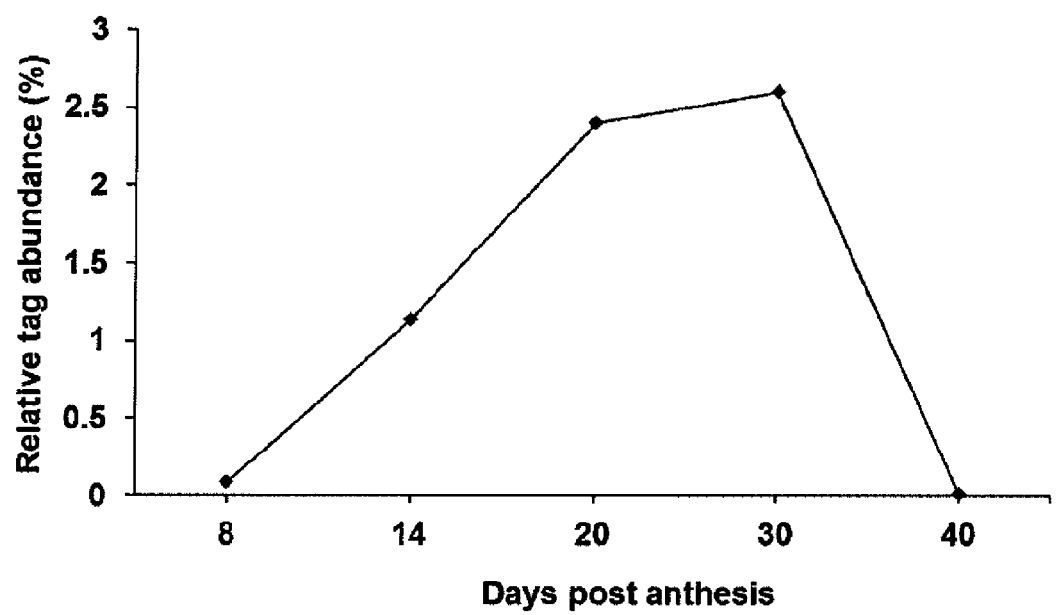
FIG. 2 sets out the relative abundance of wbm transcripts during seed development based upon frequency of "tag-A", set forth in SEQ ID NO:11, in LongSAGE libraries generated from developing seeds of wheat at different time points (days post anthesis)

SEQ ID NO:1 Amino acid sequence of the wbm protein.
SEQ ID NO:2 Nucleotide sequence of promoter variant GWSeqVar1 Ki-K3A.
SEQ ID NO:3 Nucleotide sequence of promoter variant GWSeqVar1 Ba-B3A.
SEQ ID NO:4 Nucleotide sequence of promoter variant GWSeqVar5 Ki-K1B.
SEQ ID NO:5 Nucleotide sequence of promoter variant GWSeqVar4 Ki-K4B.
SEQ ID NO:6 Nucleotide sequence of promoter variant GWSeqVar4 Ba-B2A.
SEQ ID NO:7 Nucleotide sequence of promoter variant GWSeqVar6 Ba-B1A.
SEQ ID NO:8 Nucleotide sequence of promoter variant GWSeqVar2 Ki-K2A.
SEQ ID NO:9 Nucleotide sequence of promoter variant GWSeqVar2 BaB4A.
SEQ ID NO:10 Nucleotide sequence of promoter variant GWSeqVar3 Ba-B2B, herein referred to as GWSeqVar3.
SEQ ID NO:11 Nucleotide sequence of LongS AGE tag-A corresponding to wheat cv. Banks wbm transcript.
SEQ ID NO:12 Nucleotide sequence of CDS encoding the wbm protein comprising the amino acid sequence set forth in SEQ ID NO:1.
SEQ ID NO:13 Nucleotide sequence of 5' wbm coding sequence variant Sequence variant-1.
SEQ ID NO:14 Nucleotide sequence of 5' wbrn coding sequence variant Sequence variant-2.
SEQ ID NO:15 Nucleotide sequence of 5' wbm coding sequence variant Sequence variant-3.
SEQ ID NO:16 Nucleotide sequence of 5' wbm coding sequence variant Sequence variant-4.
SEQ ID NO:17 Nucleotide sequence of 3' wbrn coding sequence variant Sequence variant-A.
SEQ ID NO:18 Nucleotide sequence of 3' wbm coding sequence variant Sequence variant-B.
SEQ ID NO:19 Nucleotide sequence of genome walking primer NW1.
SEQ ID NO:20 Nucleotide sequence of genome walking primer NW2.
SEQ ID NO:21 Nucleotide sequence for GWSeqVar3 detection primer NWPFor.
SEQ ID NO:22 Nucleotide sequence for GWSeqVar3 detection primer NWPRev.
SEQ ID NO:23 wbm gene nucleotide sequence comprising 5' untranslated sequence, coding sequence, and 3' untranslated sequence.

DETAILED DESCRIPTION

The present invention is at least partly predicated on the discovery of a wheat protein, referred to herein as "wbm", comprising the amino acid sequence set forth in SEQ ID NO:1, that is present at relatively high levels in the seed of wheat varieties with desirable bread making properties, but absent or present at relatively low levels in the seed of wheat varieties with poor breadmaking properties. The invention therefore broadly provides means for improving breadmaking properties in wheat and other plants. Further to this, the invention provides wbm gene promoters that may facilitate enhanced or increased expression of the wbm protein or heterologous proteins.

Isolated wbm Proteins

In one aspect, the invention provides an isolated protein comprising the amino acid sequence set forth in SEQ ID NO:1.

For the purposes of this invention, by "isolated" is meant material that has been removed from its natural state or otherwise been subjected to human manipulation. Isolated material may be substantially or essentially free from components that normally accompany it in its natural state, or may be manipulated so as to be in an artificial state together with components that normally accompany it in its natural state. Isolated material may be in native, chemical synthetic or recombinant form.

By "protein" is meant an amino acid polymer, comprising natural and/or non-natural amino acids, including L- and D-isomeric forms as are well understood in the art.

Also provided are fragments of the isolated wbm protein.

In certain embodiments, a protein "fragment" includes an amino acid sequence which constitutes less than 100%, but at least 20%, preferably at least 30%, more preferably at least 80% or even more preferably at least 90%, 91%, 92%, 93%, 94%, 95%, 96%, 97%, 98% or 99% of an isolated wbm protein as herein described.

In other embodiments, a protein fragment comprises no more than 10, 12, 15, 20, 25, 30, 35, 40, 45, 50, 65, or 70 contiguous amino acids of SEQ ID NO:1.

The protein fragment may also be a "biologically active fragment" which retains biological activity of said protein.

The biologically active fragment of a wbm protein preferably has greater than 10%, preferably greater than 20%, more preferably greater than 50% and even more preferably greater than 75%, 80%, 85%, 90% 95%, 96%, 97%, 98% or 99% of the biological activity of the entire protein.

Non-limiting examples of biological activities include complexing with lipids and/or linking lipids and proteins; and interacting in the formation of disulphide bonds in gluten.

In some embodiments, the fragment may comprise a domain with homology to a MD-2-related lipid-recognition domain.

This aspect also provides variants and derivatives of said protein. As used herein, a "variant" protein is a wbm protein of the invention in which one or more amino acids have been deleted or substituted by different amino acids.

Variants include naturally occurring (e.g., allelic) variants, orthologs (i.e from species other than *Triticum aestivum*) and synthetic variants, such as produced in vitro using mutagenesis techniques.

Variants may retain the biological activity of a corresponding wild type protein (e.g. allelic variants, paralogs and orthologs) or may lack, or have a substantially reduced, biological activity compared to a corresponding wild type protein.

In some embodiments, variants include proteins having at least 75%, 80%, 85%, 90% or 95%, 96%, 97%, 98% or 99% amino acid sequence identity to the wheat wbm protein set forth in SEQ ID NO:1.

In some embodiments, the variant may comprise a domain with homology to a MD-2-related lipid-recognition domain.

It will be appreciated that wbm protein variants may also be protein fragments. Terms used generally herein to describe sequence relationships between respective proteins and nucleic acids include "comparison window", "sequence identity", "percentage of sequence identity" and "substantial identity". Because respective nucleic acids/proteins may each comprise (1) only one or more portions of a complete nucleic acid/protein sequence that are shared by the nucleic acids/proteins, and (2) one or more portions which are divergent between the nucleic acids/proteins, sequence comparisons are typically performed by comparing sequences over a "comparison window" to identify and compare local regions of sequence similarity. A "comparison window" refers to a conceptual segment of typically 6, 9 or 12 contiguous residues that is compared to a reference sequence. The comparison window may comprise additions or deletions (i.e., gaps) of about 20% or less as compared to the reference sequence for optimal alignment of the respective sequences. Optimal alignment of sequences for aligning a comparison window may be conducted by computerised implementations of algorithms (Geneworks program by Intelligenetics; GAP, BESTFIT, FASTA, and TFASTA in the Wisconsin Genetics Software Package Release 7.0, Genetics Computer Group, 575 Science Drive Madison, Wis., USA, incorporated herein by reference) or by inspection and the best alignment (i.e., resulting in the highest percentage homology over the comparison window) generated by any of the various methods selected. Reference also may be made to the BLAST family of programs as for example disclosed by Altschul et al., 1997, Nucl. Acids Res. 25 3389, which is incorporated herein by reference. A detailed discussion of sequence analysis can be found in Unit 19.3 of CURRENT PROTOCOLS IN MOLECULAR BIOLOGY Eds. Ausubel et al. (John Wiley & Sons Inc NY, 1995-1999).

The term "sequence identity" is used herein in its broadest sense to include the number of exact nucleotide or amino acid matches having regard to an appropriate alignment using a standard algorithm, having regard to the extent that sequences are identical over a window of comparison. Thus, a "percentage of sequence identity" is calculated by comparing two optimally aligned sequences over the window of comparison, determining the number of positions at which the identical nucleic acid base (e.g., A, T, C, G, U) occurs in both sequences to yield the number of matched positions, dividing the number of matched positions by the total number of positions in the window of comparison (i.e., the window size), and multiplying the result by 100 to yield the percentage of sequence identity. For example, "sequence identity" may be understood to mean the "match percentage" calculated by the DNASIS computer program (Version 2.5 for Windows; available from Hitachi Software engineering Co., Ltd., South San Francisco, Calif., USA).

A detailed discussion of sequence analysis can be found in Chapter 19.3 of Ausubel et al., supra.

With regard to protein variants, these can be created by mutagenizing a protein or an encoding nucleic acid, such as by random mutagenesis or site-directed mutagenesis. Examples of nucleic acid mutagenesis methods are provided in Chapter 9 of CURRENT PROTOCOLS IN MOLECULAR BIOLOGY, Ausubel et al., supra which is incorporated herein by reference.

It will be appreciated by the skilled person that site-directed mutagenesis is best performed where knowledge of the amino acid residues that contribute to biological activity is available.

In cases where this information is not available, or can only be inferred by molecular modelling approximations, for example, random mutagenesis is contemplated. Random mutagenesis methods include chemical modification of proteins by hydroxylamine (Ruan et al., 1997, Gene 188 35), incorporation of dNTP analogs into nucleic acids (Zaccolo et al., 1996, J. Mol. Biol. 255 589) and PCR-based random mutagenesis such as described in Stemmer, 1994, Proc. Natl. Acad. Sci. USA 91 10747 or Shafikhani et al., 1997, Biotechniques 23 304, each of which references is incorporated herein. It is also noted that PCR-based random mutagenesis kits are commercially available, such as the Diversify™ kit (Clontech).

Mutagenesis may also be induced by chemical means, such as ethyl methane sulphonate (EMS) and/or irradiation means, such as fast neutron irradiation of seeds as known in the art (Carroll et al., 1985, Proc. Natl. Acad. Sci. USA 82 4162; Carroll et al, 1985, Plant Physiol. 78 34; Men et al., 2002, Genome Letters 3 147).

As used herein, "derivative" proteins are proteins of the invention that have been altered, for example by conjugation or complexing with other chemical moieties or by post-translational modification techniques as would be understood in the art. Such derivatives include amino acid deletions and/or additions to polypeptides of the invention, or variants thereof.

"Additions" of amino acids may include fusion of the peptide or polypeptides of the invention, or variants thereof, with other peptides or polypeptides. Particular examples of such peptides include amino (N) and carboxyl (C) terminal amino acids added for use as fusion partners or "tags".

Well-known examples of fusion partners include hexa-histidine (6X-HIS)-tag, N-Flag, Fc portion of human IgG, glutathione-S-transferase (GST) and maltose binding protein (MBP), which are particularly useful for isolation of the fusion polypeptide by affinity chromatography. For the purposes of fusion polypeptide purification by affinity chromatography, relevant matrices for affinity chromatography may include nickel-conjugated or cobalt-conjugated resins, fusion polypeptide specific antibodies, glutathione-conjugated resins, and amylose-conjugated resins respectively. Some matrices are available in "kit" form, such as the ProBond™ Purification System (Invitrogene Corp.) which incorporates a 6X-His fusion vector and purification using ProBond™ resin.

The fusion partners may also have protease cleavage sites, for example enterokinase (available from Invitrogen Corp. as EnterokinaseMax™), Factor $X_a$ or Thrombin, which allow the relevant protease to digest the fusion polypeptide of the invention and thereby liberate the recombinant polypeptide of the invention therefrom. The liberated polypeptide can then be isolated from the fusion partner by subsequent chromatographic separation.

Fusion partners may also include within their scope "epitope tags", which are usually short peptide sequences for which a specific antibody is available.

Other derivatives contemplated by the invention include, chemical modification to side chains, incorporation of unnatural amino acids and/or their derivatives during peptide or polypeptide synthesis and the use of cross linkers and other methods which impose conformational constraints on the polypeptides, fragments and variants of the invention.

Non-limiting examples of side chain modifications contemplated by the present invention include chemical modifications of amino groups, carboxyl groups, guanidine groups of arginine residues, sulphydryl groups, tryptophan residues, tyrosine residues and/or the imidazole ring of histidine residues, as are well understood in the art.

Non-limiting examples of incorporating unnatural amino acids and derivatives during peptide synthesis include, use of 4-amino butyric acid, 6-aminohexanoic acid, 4-amino-3-hydroxy-5-phenylpentanoic acid, 4-amino-3-hydroxy-6-methylheptanoic acid, t-butylglycine, norleucine, norvaline, phenylglycine, ornithine, sarcosine, 2-thienyl alanine and/or D-isomers of amino acids.

Recombinant wbm proteins may be conveniently expressed and purified by a person skilled in the art using commercially available kits, for example.

Recombinant proteins may be produced, as for example described in Sambrook, et al., MOLECULAR CLONING. A Laboratory Manual (Cold Spring Harbor Press, 1989), incorporated herein by reference, in particular Sections 16 and 17; CURRENT PROTOCOLS IN MOLECULAR BIOLOGY Eds. Ausubel et al., (John Wiley & Sons, Inc. 1995-1999), incorporated herein by reference, in particular Chapters 10 and 16; and CURRENT PROTOCOLS IN PROTEIN SCIENCE Eds. Coligan et al., (John Wiley & Sons, Inc. 1995-1999) which is incorporated by reference herein, in particular Chapters 1, 5, 6 and 7.

Isolated Nucleic Acids

Certain embodiments of the invention relate to nucleic acids encoding a wbm protein of the invention. Certain other embodiments of the invention relate to promoters and promoter active fragments of nucleic acids encoding a wbm protein of the invention.

The term "nucleic acid" as used herein designates single- or double-stranded DNA and RNA. DNA includes genomic DNA and cDNA. RNA includes mRNA, RNA, RNAi, siRNA, cRNA and autocatalytic RNA. Nucleic acids may also be DNA-RNA hybrids. A nucleic acid comprises a nucleotide sequence which typically includes nucleotides that comprise an A, G, C, T or U base. However, nucleotide sequences may include other bases such as inosine, methylycytosine, methylinosine, methyladenosine and/or thiouridine, although without limitation thereto.

A "polynucleotide" is a nucleic acid having eighty (80) or more contiguous nucleotides, while an "oligonucleotide" has less than eighty (80) contiguous nucleotides.

A "probe" may be a single or double-stranded oligonucleotide or polynucleotide, suitably labelled for the purpose of detecting complementary sequences in Northern or Southern blotting, for example.

A "primer" is usually a single-stranded oligonucleotide, preferably having 15-50 contiguous nucleotides, which is capable of annealing to a complementary nucleic acid "template" and being extended in a template-dependent fashion by the action of a DNA polymerase such as Taq polymerase, RNA-dependent DNA polymerase or Sequenase™.

In some embodiments, a nucleic acid that encodes a wbm protein of the present invention may be of a wbm gene (such as set forth in SEQ ID NO:23) or a fragment or variant thereof. The isolated nucleic acid may comprise one or more of: a protein coding region (CDS) or open reading frame (ORF); promoter and promoter active fragment(s); exons; introns and their respective splice sequences; and 5' and 3' untranslated sequences, although without limitation thereto. The nucleotide sequence of one particular CDS of a wbm gene of the invention is set forth in SEQ ID NO:12. The nucleotide sequence of certain particular promoters of a wbm gene provided by the invention are set forth in SEQ ID NOS:2-9.

It will be readily understood that a promoter active fragment of a promoter sequence, when fused to a particular gene and introduced into a plant cell, causes expression of the gene at a higher level than is possible in the absence of such fragment. The activity of a promoter can be determined by methods well known in the art. For example, reference may be made to Medberry et al. (1992, Plant Cell 4:185; 1993, The Plant J. 3:619, incorporated herein by reference), Sambrook et al. (1989, supra) and McPherson et al. (U.S. Pat. No. 5,164,316, incorporated herein by reference).

As will be understood by those skilled in the art, certain promoters are capable of directing RNA production in many or all tissues and are thus termed "constitutive promoters". Alternatively, other promoters have been shown to direct RNA production at higher levels only in particular types of cells or tissues and are referred to as "tissue-specific promoters".

Certain minimal nucleic acid regions, otherwise known as regulatory elements, are required for a fragment to possess promoter-activity. Such control elements are a mixture of distinct promoter sequence elements such as but not limited to, the TATA box, the INR element, the BRE element, the plastid element and the endosperm specific element as well as binding sites for gene-specific transcription factors. It is well known in the art that for example, the TATA box and the INR element are able to independently initiate accurate transcription.

The invention also contemplates variants of an isolated nucleic acid encoding a wbm protein of the invention and/or variants of a promoter or promoter active fragment of a wbm gene.

As used herein, the term "variant", in relation to an isolated nucleic acid, includes naturally-occurring allelic variants.

Variants also include nucleic acids that have been mutagenized or otherwise altered so as to encode a protein having the same amino acid sequence (e.g., through degeneracy), or a modified amino acid sequence.

In the context of promoters, a "variant" nucleic acid may be mutagenized or otherwise altered to have little or no effect upon promoter activity, for example in cases where more convenient restriction endonuclease cleavage and/or recognition sites are introduced without substantially affecting the encoded protein or promoter activity. Other nucleotide sequence alterations may be introduced so as to modify promoter activity. These alterations may include deletion, substitution or addition of one or more nucleotides in a promoter. The alteration may either increase or decrease activity as required. In this regard, nucleic acid mutagenesis may be performed in a random fashion or by site-directed mutagenesis in a more "rational" manner. Standard mutagenesis techniques are well known in the art, and examples are provided in Chapter 9 of CURRENT PROTOCOLS IN MOLECULAR BIOLOGY Eds Ausubel et al. (John Wiley & Sons NY, 1995), which is incorporated herein by reference.

Mutagenesis also includes mutagenesis using chemical and/or irradiation methods such as EMS and fast neutron mutagenesis of plant seeds.

In certain embodiments, nucleic acid variants are nucleic acids having one or more codon sequences altered by taking advantage of codon sequence redundancy.

A particular example of this embodiment is optimization of a nucleic acid sequence according to codon usage as is well known in the art. This can effectively "tailor" a nucleic acid for optimal expression in a particular organism, or cells thereof, where preferential codon usage has been established.

Nucleic acid variants also include within their scope "homologs", "orthologs" and "paralogs".

Nucleic acid orthologs may encode orthologs corresponding to a wbm protein of the invention that may be isolated, derived or otherwise obtained from plants other than *Triticum aestivum*.

Preferably, orthologs are obtainable from plants such as grass species of the family Poaceae; cereals including maize, *sorghum*, barley, and rice; leguminous species including beans and peanut; solanaceous species including tomato and potato; and model plant species including the model dicotyledonous species *Arabidopsis* and the model monocotyledonous species *Brachypodium distachyon*.

In another embodiment, nucleic acid homologs share at least 65%, preferably at least 70%, more preferably at least 80% or 85% and even more preferably 90%, 91%, 92%, 93%, 94%, 95%, 96%, 97%, 98% or 99%, sequence identity with a nucleic acid of a a wbm gene, or other wbm-encoding nucleic acid or associated regulatory element.

In yet another embodiment, nucleic acid homologs hybridize to nucleic acids of encoding a wbm nucleic acid of the invention under high stringency conditions.

"Hybridise and Hybridisation" is used herein to denote the pairing of at least partly complementary nucleotide sequences to produce a DNA-DNA, RNA-RNA or DNA-RNA hybrid. Hybrid sequences comprising complementary nucleotide sequences occur through base-pairing.

Modified purines (for example, inosine, methylinosine and methyladenosine) and modified pyrimidines (thiouridine and methylcytosine) may also engage in base pairing.

"Stringency" as used herein, refers to temperature and ionic strength conditions, and presence or absence of certain organic solvents and/or detergents during hybridisation. The higher the stringency, the higher will be the required level of complementarity between hybridizing nucleotide sequences.

"Stringent conditions" designates those conditions under which only nucleic acid having a high frequency of complementary bases will hybridize.

Reference herein to high stringency conditions includes and encompasses:

(i) from at least about 31% v/v to at least about 50% v/v formamide and from at least about 0.01 M to at least about 0.15 M NaCl for hybridisation at 42° C., and at least about 0.01 M to at least about 0.15 M salt for washing at 42° C.;

(ii) 1% BSA, 1 mM EDTA, 0.5 M NaHPO$_4$ (pH 7.2), 7% SDS for hybridization at 65° C., and (a) 0.1×SSC, 0.1% SDS; or (b) 0.5% BSA, 1 mM EDTA, 40 mM NaHPO$_4$ (pH 7.2), 1% SDS for washing at a temperature in excess of 65° C. for about one hour; and (iii) 0.2×SSC, 0.1% SDS for washing at or above 68° C. for about 20 minutes.

Notwithstanding the above, stringent conditions are well-known in the art, such as described in Chapters 2.9 and 2.10 of Ausubel et al., supra, which are herein incorporated by reference. A skilled addressee will also recognize that various factors can be manipulated to optimize the specificity of the hybridization. Optimization of the stringency of the final washes can serve to ensure a high degree of hybridization.

Typically, complementary nucleotide sequences are identified by blotting techniques that include a step whereby nucleotides are immobilized on a matrix (preferably a synthetic membrane such as nitrocellulose), a hybridization step, and a detection step.

In light of the foregoing, it will be appreciated that variants, homologs and orthologs may be isolated by means such as nucleic acid sequence amplification techniques, (including but not limited to PCR, strand displacement amplification, rolling circle amplification, helicase-dependent amplification and the like) and techniques which employ nucleic acid hybridization (e.g., plaque/colony hybridization.

One particular aspect relating to promoter or promoter-active variants of the invention provides promoter or promoter-active fragments comprising one or more nucleotide sequence additions, deletions and/or substitutions to any one of SEQ ID NOS:2-9 that relatively increase or elevate the activity of said promoter or promoter active fragment, wherein the nucleotide sequence of said promoter or promoter active fragment is not SEQ ID NO:10.

Figure 9:
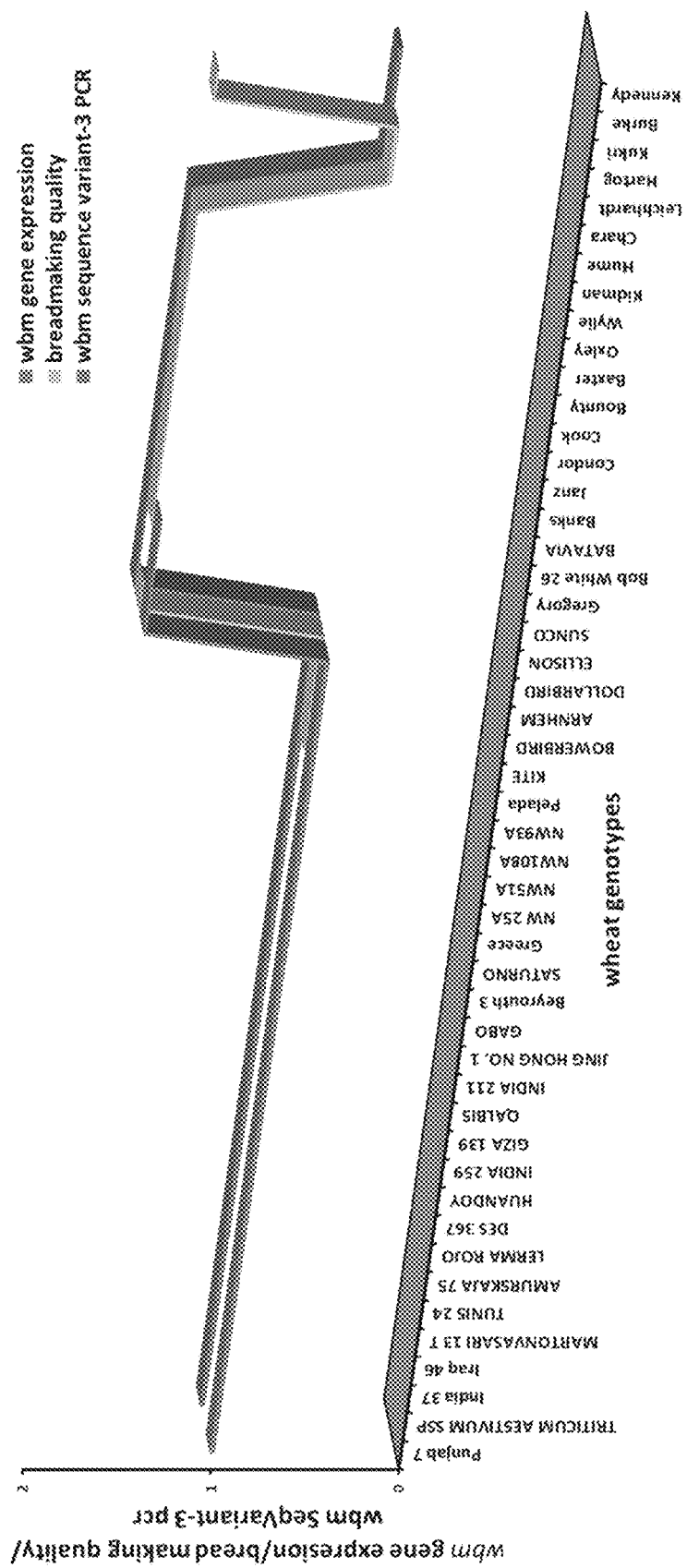
FIG. 9 sets out the classification of a large number of wheat genotypes with respect to: level of expression of wbm in developing seeds, bread making quality, and the presence of the GWseqVar3 wbm promoter-active fragment variant. A score on the Y axis of 1 versus 2 corresponds to low versus high wbm gene expression respectively, good versus poor bread making quality respectively, absence versus presence of the GWseqVar3 wbm promoter-active fragment variant, respectively.
Figure 11:
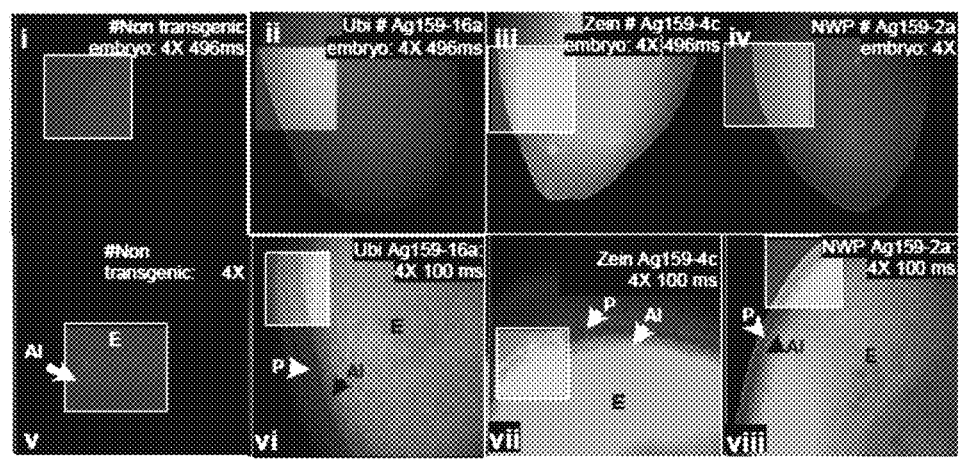
FIG. 11 sets out green fluorescent protein gene expression driven by the ubiquitin (Ubi), zein (Zein) and GWSeqVar3 (NWP) promoters in developing seed tissues of transgenic maize plants. (i,ii,iii,iv), embryo; (v,vi,vii,viii), transverse section of developing seed at 20-25 days after flowering; (i,v), no transformed tissue; (ii,vi), ubiquitin promoter-transformed tissue; (iii,vii), zein promoter-transformed tissue; (iv,viii) GWSeqVar3 promoter-transformed tissue. The ubi, zein and the GWSeqVar3 promoters direct the expression of GFP in the embryo, aleurone and the endosperm tissue. Detecting the expression of GFP in transgenic tissue was carried out by comparison with corresponding tissues of non-transformed plants (i,v). Observations were carried out under blue light (excitation, 489 nm; emission, 510 nm) using a compound fluorescence microscope. Representative images for promoter lines are shown and images were taken at different exposure times for clarity of images. #, line numbers of independent transgenic events; s, seconds; ms, milliseconds. Enhanced areas of images are represented as a box with a white border.
Figure 12:
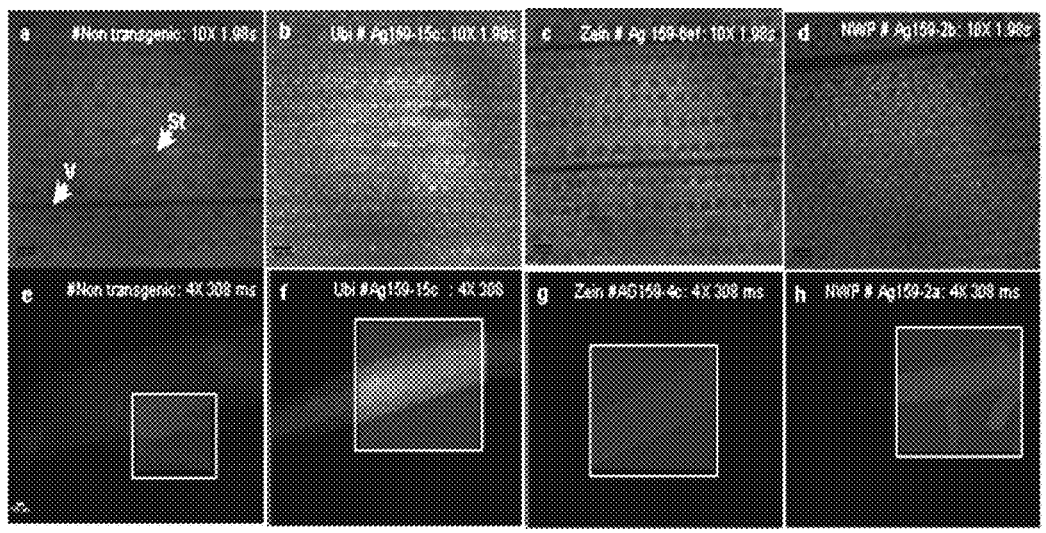
FIG. 12 sets out green fluorescent protein gene expression by the ubiquitin (Ubi), zein (Zein) and GWSeqVar3 (NWP) promoters in non-seed tissues of transgenic maize plants. (a,b,c,d), leaf; (e,f,g,h), root; (a,e), non-transformed, (b,f), maize polyubiquitin ubiquitin promoter-transformed tissue; (c,g), zein promoter-transformed tissue; (d,h) GWSeqVar3 wheat promoter-transformed tissue. The Ubi promoter directed expression of GFP in the veins and stomata of leaf tissue and also in root tissue. The zein and the GWSeqVar3 promoters do not direct GFP expression in the leaf or the root tissues. Apparent low-levels of GFP expression detected all chlorophyll containing tissues (including those of the non-transformed lines) was an artefact due to interference from red fluorescence from chlorophyll. As such, detection of true expression of GFP in transgenic tissue was carried out by comparison with corresponding tissues of non-transformed plants (a,e). Observations were carried out under blue light (excitation, 489 nm; emission, 510 nm) using a compound fluorescence microscope. Red fluorescence is due to chlorophyll and yellow fluorescence is due to non-GFP-expressing living tissue and dead tissue. Representative images for promoter lines are shown and images were taken at different exposure times for clarity of images. #, line numbers of independent transgenic events; s, seconds; ms, milliseconds. Enhanced areas of images are represented as a box with a white border.
Figure 13:
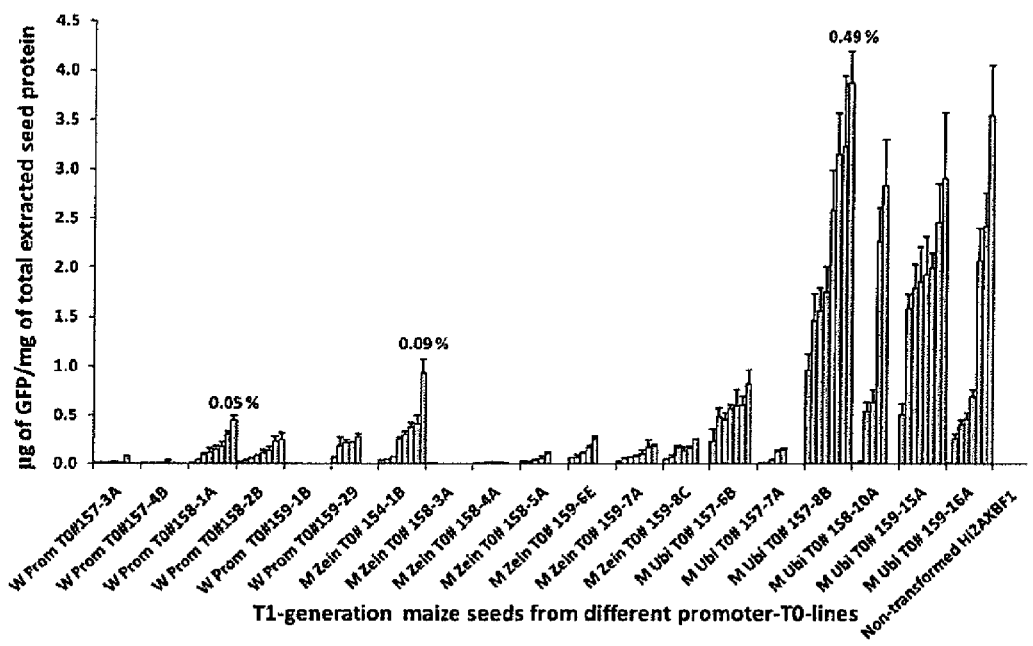
FIG. 13 sets out expression of GFP in individual T1-generation maize seeds under control of wheat and maize promoters. W Prom, GWSeqVar3 promoter from wheat; M Zein, zein promoter from maize (Accession# V01470); M Ubi, maize polyubiquitin promoter. Measurement of GFP was carried out by ELISA in single seeds (minimum of four per transgenic line) and expressed as concentration per milligram of total extracted seed protein. Data represents values of three to six independent ELISA measurements.
Figure 14:
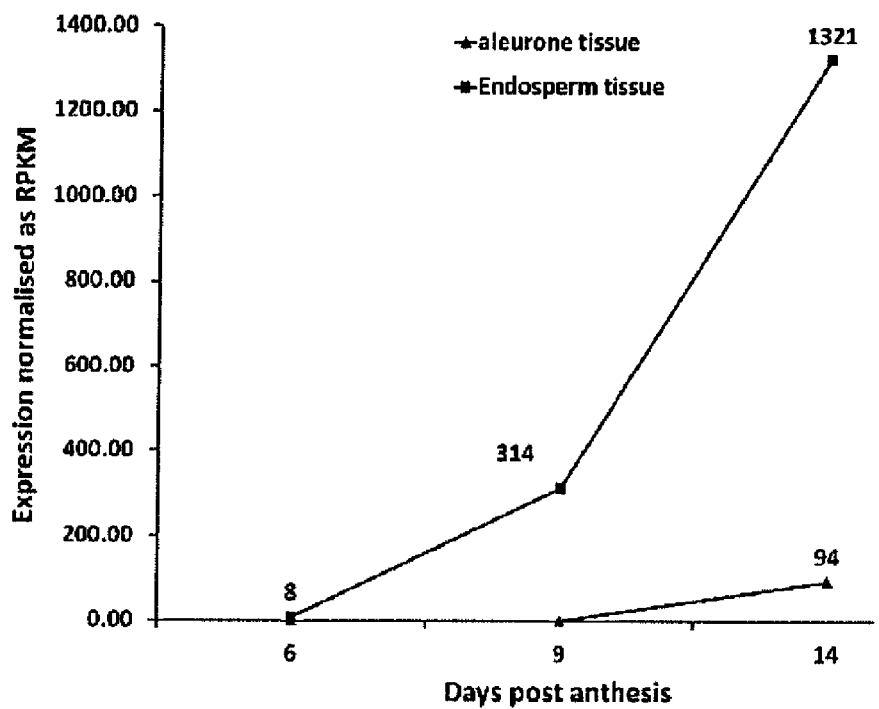
FIG. 14 sets out a comparison of the expression of wbm transcripts in aleurone versus endosperm of the seed of wheat variety cv. Banks.

As will be evident from EXAMPLE 3 and FIG. 9 the promoter set forth in SEQ ID NO:10 regulates a level of expression of the wbm protein of the invention that is increased or elevated, as herein described, relative to the level of expression of the wbm protein regulated by the promoters set forth in SEQ ID NOS:2-9. Therefore, the promoter set forth in SEQ ID NO:10 will be understood to be a wbm promoter that is "strong", "active", or comprises "increased activity".

It will be further understood that the promoters set forth in SEQ ID NOS:2-9 are referred to as wbm promoters that are "weak" or "less active".

Figure 7:
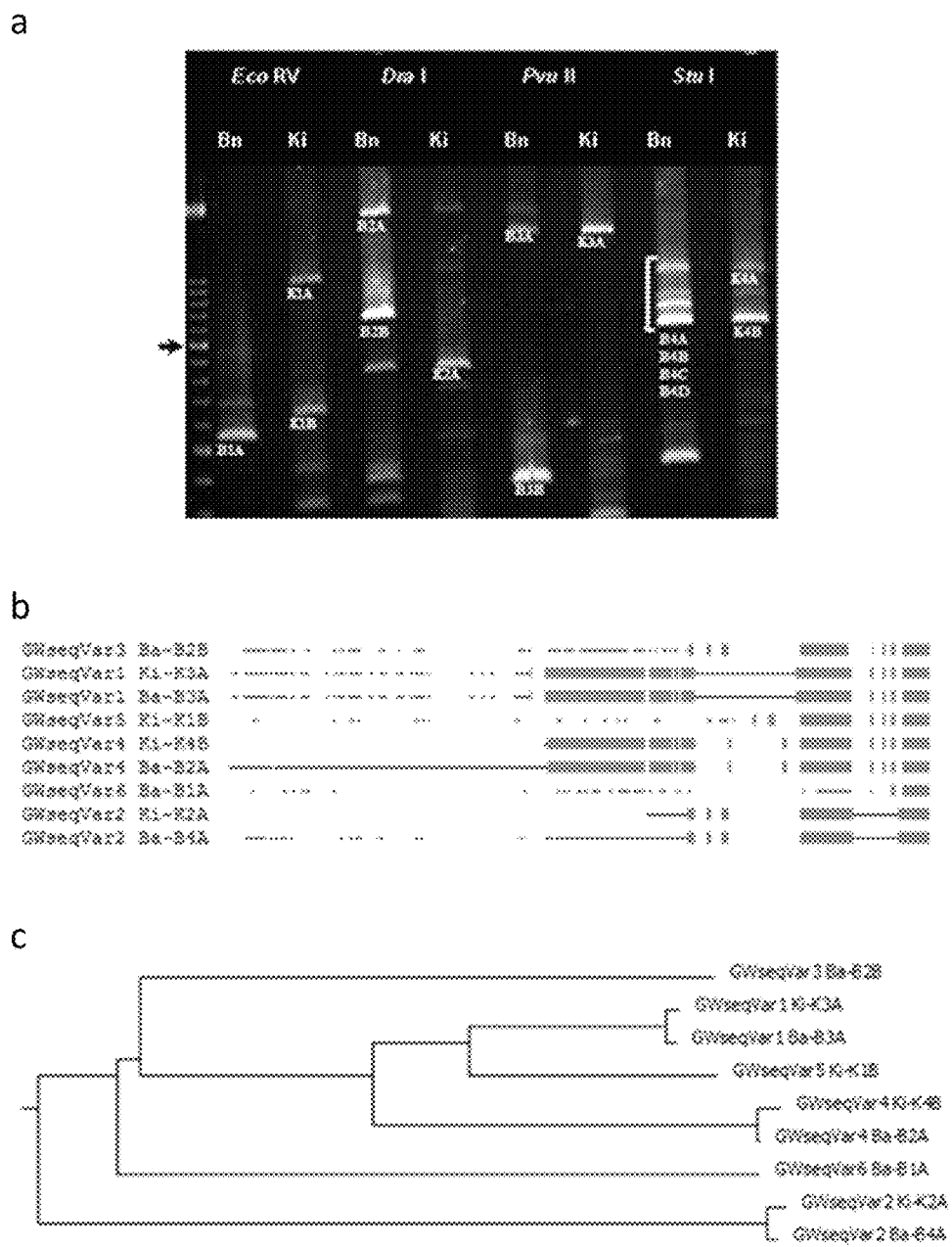
FIG. 7 sets out agarose-gel-electrophoresis resolved Genome Walker PCR fragments and alignments of isolated Genome Walker (GW) fragments from Banks (Bn) and Kite (Ki) corresponding to the 5'-upstream regions of wbm genes. a, GW fragments amplified using the Eco RV, Dra I, Pvu II and Stu I GW-libraries respectively is shown in as A, B, C and D, GW PCR fragment identified in descending order of size; b, the 5'-upstream sequences from each cultivar representing the longest GW sequence of a specific allele (set forth in SEQ ID NOS:2-10); a schematic of the homology between the GW fragments is shown wherein blue shading indicated regions of relatively high sequence homology; c, a dendogram showing the relatedness of the upstream sequences in 'b'. Arrow in 'a' indicates 1000 bp DNA size marker.
Figure 8:
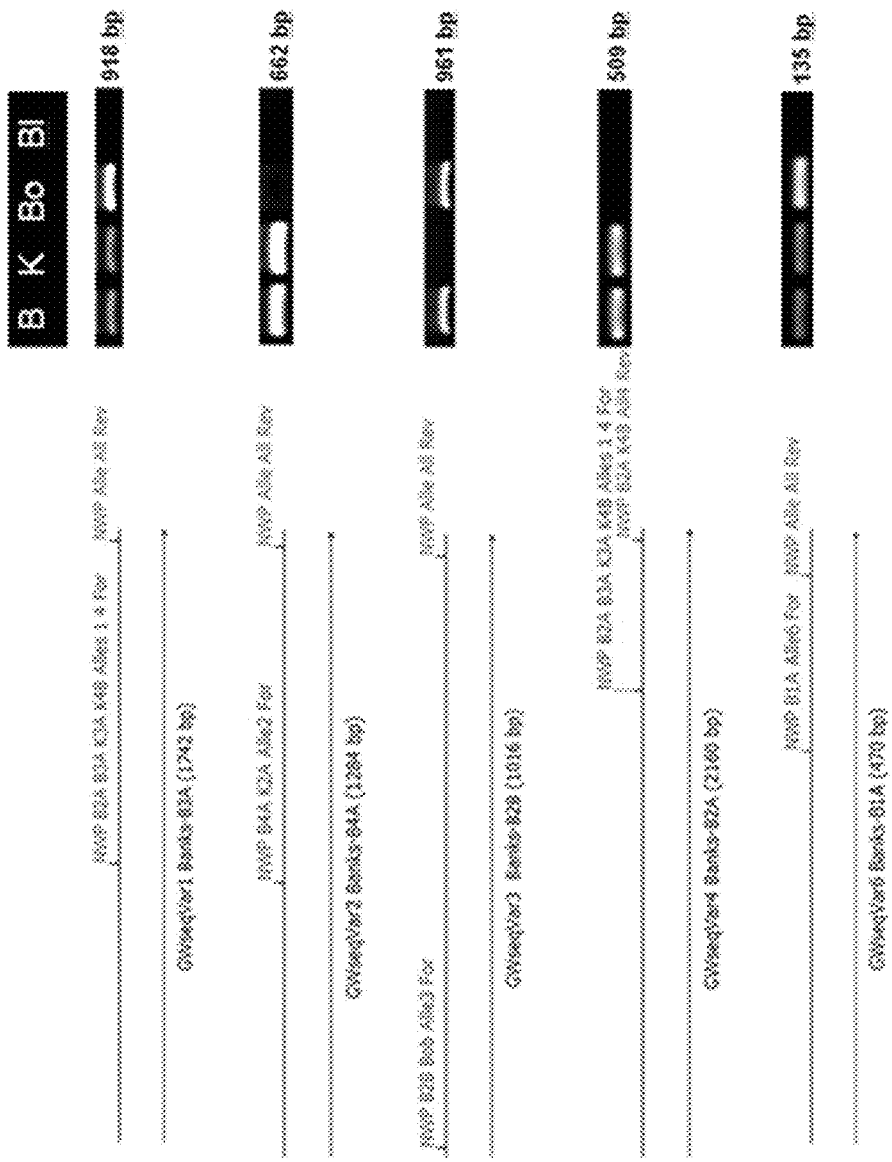
FIG. 8 sets out PCR amplification of fragments of the 5'-upstream sequence variants of the wbm gene from wheat cvs. Banks (B), Kite (K) and Bobwhite (Bo). B1 is a no template control. Primers were designed to discriminate the wbm sequence variants based on amplified fragment sizes. A 961 bp amplified fragment of the GWseqVar3 variant is present in cvs. Banks and Bobwhite but not in Kite.

As will be evident from EXAMPLE 3 and FIGS. 7 and 16, the promoter set forth in SEQ ID NO:10 comprises nucleotide sequence additions, deletions and/or substitutions as compared to the promoters set forth in SEQ ID NOS:2-9. It is proposed that at least one of the nucleotide sequence additions, deletions and/or substitutions of SEQ ID NO:10 confer the superior promoter activity of SEQ ID NO:10 compared to SEQ ID NOS:2-9.

It will therefore be understood by a person skilled in the art that it may be possible to increase the activity of a less active wbm promoter or promoter-active fragment comprising any one of the nucleotide sequences set forth in SEQ ID NOS:2-9 by modifying said nucleotide sequence to comprise one or more nucleotide sequence additions, deletions and/or substitutions present in SEQ ID NO:10, as compared to the promoter active fragments set forth in SEQ ID NOS:2-9.

Therefore, in preferred embodiments, the one or more nucleotide sequence additions, deletions and/or substitutions to any one of SEQ ID NOS:2-9 that relatively increase or elevate the activity of said promoter or promoter active fragment, are present in SEQ ID NO:10 but are not present in SEQ ID NOS:2-9.

Suitably, the nucleotide sequence of the modified promoter or promoter active fragment is not SEQ ID NO:10.

It will also be evident from EXAMPLE 3 and FIGS. 11, 12, and 13 that the wbm promoter with sequence set forth in SEQ ID NO:10 is a seed-specific promoter. It will be further evident from EXAMPLE 3 and FIG. 14 that SEQ ID NO:10 is a substantially "endosperm-specific" promoter.

Therefore, in certain preferred embodiments of the invention, a wbm promoter or promoter-active fragment of the invention is a seed specific promoter or promoter-active fragment, or preferably an endosperm specific promoter or promoter-active fragment.

Genetic Constructs

In certain embodiments, a "genetic construct" of the invention comprises an isolated nucleic acid encoding a wbm protein of the invention. In some embodiments, the isolated nucleic acid comprises a nucleotide sequence such as set forth in SEQ ID NO:12 or SEQ ID NO:23, and/or of a wbm promoter or promoter-active fragment such as set forth in any one of SEQ ID NOS:2-9, together with one or more other elements that facilitate manipulation, propagation, homologous recombination and/or expression of said nucleic acid.

In certain preferred embodiments, the promoter-active fragment comprises a nucleotide sequence comprising one or more nucleotide sequence additions, deletions and/or substitutions to any one of SEQ ID NOS:2-9 that relatively increase or elevate the activity of said promoter or promoter active fragment, wherein the nucleotide sequence of said modified promoter or promoter active fragment is not SEQ ID NO:10.

In one preferred form, the genetic construct is an expression construct, which is suitable for the expression of a nucleic acid encoding the wbm protein of the invention.

The genetic construct may be particularly advantageous when expressed in a plant, to enhance or improve bread-making properties of said plant.

Alternatively, expression constructs may be RNAi or anti-sense constructs that facilitate down-regulation of wbm expression in plants.

Typically, an expression construct comprises one or more regulatory sequences present in an expression vector, "operably linked" or "operably connected" to the nucleic acid corresponding to a wbm protein of the invention, to thereby assist, control or otherwise facilitate transcription and/or translation of the nucleic acid encoding the wbm protein of invention.

By "operably linked" or "operably connected" is meant that said regulatory nucleotide sequence(s) is/are positioned relative to the nucleic acid nucleic acid encoding the wbm protein to initiate, regulate or otherwise control transcription and/or translation.

Regulatory nucleotide sequences will generally be appropriate for the host cell used for expression. Numerous types of appropriate expression vectors and suitable regulatory sequences are known in the art for a variety of host cells.

Typically, said one or more regulatory nucleotide sequences may include promoter sequences, leader or signal sequences, ribosomal binding sites, transcriptional start and termination sequences, translational start and termination sequences, and enhancer or activator sequences.

A host cell or organism for nucleic acid and/or protein expression may be prokaryotic or eukaryotic.

In embodiments where a wbm protein coding sequence is to be expressed in a bacterial cell (e.g., *E. coli* DH5a or BL21), such as for recombinant protein production, an inducible promoter may be utilized, such as the IPTG-inducible lacZ promoter.

Other regulatory elements that may assist recombinant protein expression in bacteria include bacterial origins of replication (e.g., as in plasmids pBR322, pUC19 and the ColE1 replicon which function in many *E. coli*. strains) and bacterial selection marker genes ($amp^r$, $tet^r$ and $kan^r$, for example), In certain embodiments a wbm promoter-active fragment, as hereinbefore described, may be used as a promoter to facilitate expression of a wbm protein of the invention. Alternatively, the expression construct may comprise a heterologous promoter operable in a host cell, for example a plant cell.

Non-limiting examples of suitable heterologous promoters for expression in plants include the CaMV35S promoter, Emu promoter (Last et al., 1991, Theor. Appl. Genet. 81 581) or the maize ubiquitin promoter Ubi (Christensen & Quail, 1996, Transgenic Research 5 213).

Usually, when transgenic expression of a protein is required, a correct orientation of the encoding nucleic acid transgene is in the sense or 5' to 3' direction relative to the promoter. However, where antisense expression is required, the transcribable nucleic acid is oriented 3' to 5'. Both possibilities are contemplated by the expression construct of the present invention, and directional cloning for these purposes may be assisted by the presence of a polylinker.

An expression vector may further comprise viral and/or plant pathogen nucleotide sequences. A plant pathogen nucleic acid includes a T-DNA plasmid, modified (including for example a recombinant nucleic acid) or otherwise, from *Agrobacterium*.

The expression vector may further comprise a selectable marker nucleic acid to allow the selection of transformed cells.

In embodiments relating to expression in plants, suitable selection markers include, but are not limited to, neomycin phosphotransferase II which confers kanamycin and geneticin/G418 resistance (nptll; Raynaerts et al., In: Plant Molecular Biology Manual A9:1-16. Gelvin & Schilperoort Eds (Kluwer, Dordrecht, 1988), bialophos/phosphinothricin resistance (bar; Thompson et al., 1987, EMBO J. 6 1589), streptomycin resistance (aadA; Jones et al., 1987, Mol. Gen. Genet. 210 86) paromomycin resistance (Mauro et al., 1995, Plant Sci. 112 97), β-glucuronidase (gus; Vancanneyt et al., 1990, Mol. Gen. Genet. 220 245) and hygromycin resistance (hmr or hpt; Waldron et al., 1985, Plant Mol. Biol. 5 103; Perl et al., 1996, Nature Biotechnol. 14 624).

Selection markers such as described above may facilitate selection of transformed plant cells or tissue by addition of an appropriate selection agent post-transformation, or by allowing detection of plant tissue which expresses the selection marker by an appropriate assay. In that regard, a reporter gene such as gfp, nptll, luc or gusA may function as a selection marker.

Positive selection is also contemplated such as by the phosphomannine isomerase (PMI) system described by Wang et al., 2000, Plant Cell Rep. 19 654 and Wright et al., 2001, Plant Cell Rep. 20 429 or by the system described by Endo et al., 2001, Plant Cell Rep. 20 60, for example.

The expression construct of the present invention may also comprise other gene regulatory elements, such as a 3' non-translated sequence. A 3' non-translated sequence refers to that portion of a gene that contains a polyadenylation signal and any other regulatory signals capable of effecting mRNA processing or gene expression. The polyadenylation signal is characterized by effecting the addition of polyadenylic acid tracts to the 3' end of the mRNA precursor. Polyadenylation signals are commonly recognized by the presence of homology to the canonical form 5' AATAAA-3' although variations are not uncommon.

The 3' non-translated regulatory DNA sequence preferably includes from about 300 to 1,000 nucleotide base pairs and contains plant transcriptional and translational termination sequences. Examples of suitable 3' non-translated sequences are the 3' transcribed non-translated regions containing a polyadenylation signal from the nopaline synthase (nos) gene of *Agrobacterium tumefaciens* (Bevan et al., 1983, Nucl. Acid Res., 11 369) and the terminator for the T7 transcript from the octopine synthase (ocs) gene of *Agrobacterium tumefaciens*.

Tanscriptional enhancer elements include elements from the CaMV 35S promoter and octopine synthase (ocs) genes, as for example described in U.S. Pat. No. 5,290,924, which is incorporated herein by reference. It is proposed that the use of an enhancer element such as the ocs element, and particularly multiple copies of the element, may act to increase the level of transcription from adjacent promoters when applied in the context of plant transformation.

Additionally, targeting sequences may be employed to target a protein product of the transcribable nucleic acid to an intracellular compartment within plant cells or to the extracellular environment. For example, a DNA sequence encoding a transit or signal peptide sequence may be operably linked to a sequence encoding a desired protein such that, when translated, the transit or signal peptide can transport the protein to a particular intracellular or extracellular destination, respectively, and can then be post-translationally removed. Transit or signal peptides act by facilitating the transport of proteins through intracellular membranes, e.g., vacuole, vesicle, plastid and mitochondrial membranes, whereas signal peptides direct proteins through the extracellular membrane. For example, the transit or signal peptide can direct a desired protein to a particular organelle such as a plastid (e.g., a chloroplast), rather than to the cytoplasm. Thus, the expression construct can further comprise a plastid transit peptide encoding DNA sequence operably linked between a promoter region or promoter variant according to the invention and transcribable nucleic acid. For example, reference may be made to Heijne et al., 1989, Eur. J. Biochem. 180 535 and Keegstra et al., 1989, Ann. Rev. Plant Physiol. Plant Mol. Biol 40 471, which are incorporated herein by reference.

A genetic construct or vector may also include an element(s) that permits stable integration of the vector into the host cell genome or autonomous replication of the vector in the cell independent of the genome of the cell. The vector may be integrated into the host cell genome when introduced into a host cell. For integration, the vector may rely on the foreign or endogenous DNA sequence or any other element of the vector for stable integration of the vector into the genome by homologous recombination. Alternatively, the vector may contain additional nucleic acid sequences for directing integration by homologous recombination into the genome of the host cell. The additional nucleic acid sequences enable the vector to be integrated into the host cell genome at a precise location in the chromosome. To increase the likelihood of integration at a precise location, the integrational elements should preferably contain a sufficient number of nucleic acids, such as 100 to 1,500 base pairs, preferably 400 to 1,500 base pairs, and most preferably 800 to 1,500 base pairs, which are highly homologous with the corresponding target sequence to enhance the probability of homologous recombination. The integrational elements may be any sequence that is homologous with the target sequence in the genome of the host cell. Furthermore, the integrational elements may be non-encoding or encoding nucleic acid sequences.

The expression construct, whether for expression in plant, bacterial or other host cells, may also include a fusion partner (typically provided by the expression vector) so that a recombinant wbm protein is expressed as a fusion protein with the fusion partner, as hereinbefore described. An advantage of fusion partners is that they assist identification and/or purification of the fusion protein. Identification and/or purification may include using a monoclonal antibody or substrate specific for the fusion partner.

In certain other preferred embodiments, a genetic construct of the invention is a genetic construct for "genome editing", as hereinbelow described. Preferably, said genetic construct for genome editing targets a nucleic acid encoding a wbm protein of the invention, such as set forth in SEQ ID NO:12 or SEQ ID NO:23, and/or a promoter or promoter active fragment of the invention such as set forth in SEQ IDS:2-9.

Expression vectors suitable for genome editing in plants are available, for example the vector pZHY013 used for TALEN-based genome editing described by Zhang et al., 2013 Plant Physiol 161 20; and the vector pRGE used for CRISPR/Cas-based genome editing described by Xie et al., 2013 Mol Plant 6 1975. Furthermore, as will be understood by one skilled in the art, nucleic acids encoding the appropriate components for genome engineering in plants may be expressed using any suitable plant expression vector, as hereinbefore described.

Methods of Improving Breadmaking Properties in Plants

Certain embodiments of the invention relate to methods of improving or enhancing breadmaking properties in plants or plant parts, including the step of producing a plant capable of producing a seed comprising an increased or elevated expression, activity, or amount of the protein of the first aspect, to thereby produce a plant or plant part with improved breadmaking properties. As used throughout this specification the term "amount" will be understood to encompass the term "concentration", although without limitation thereto.

Measurement of the level of expression, activity, and/or amount of a wbm protein of the invention in a cell, tissue, or organism may be performed using any of the range of methods known to those skilled in the art. Without limitation, in certain embodiments, the amount of a wbm protein may be assessed using ELISA or Western blotting, as hereinbefore described.

In certain other embodiments, the expression of a wbm protein may be assessed by measuring the expression of a transcript encoding the wbm protein. Methods of measuring the expression of a transcript are well known in the art. For example, the expression of a transcript encoding a wbm protein may be performed by northern or Southern blotting, or by quantitative RT-PCR, as hereinbefore described.

In certain embodiments, an "increased" or "elevated" expression, activity, and/or amount of a wbm protein in a plant cell, plant tissue, or plant may be measured relative to one or more corresponding plant cells, plant tissues, or plants.

In certain embodiments, said increased or elevated expression, activity, and/or amount of a wbm protein is at least 10, at least 15, at least 20, at least 25, at least 30, at least 35, at least 40, at least 45, at least 50, at least 55, at least 60, at least 65, at least 70, at least 75, at least 80, at least 85, at least 90, at least 95, or at least 100-fold increased or elevated relative to one or more corresponding plant cells, plant tissues, or plants.

In certain other embodiments, said increased or elevated expression, activity, and/or amount of a wbm protein is at least 100, at least 150, at least 200, at least 250, at least 300, at least 350, at least 400, at least 450, at least 500, at least 550, at least 600, at least 650, at least 700, at least 750, at least 800, at least 850, at least 900, at least 950, or at least 1000-fold increased or elevated relative to one or more corresponding plant cells, plant tissues, or plants.

In certain other embodiments, said increased or elevated expression, activity, and/or amount of a wbm protein is at least 1000, 1250, at least 1500, at least 1750, at least 2000, at least 2250, at least 2500, at least 2750, at least 3000, at least 3250, at least 3500, at least 3750, at least 4000, at least 4250, at least 4500, at least 4750, at least 5000, at least 5250, at least 5500, at least 5750, at least 6000, at least 6250, at least 6500, at least 6750, at least 7000, at least 7250, at least 7500, at least 7750, at least 8000, at least 8250, at least 8500, at least 8750, at least 9000, at least 9250, at least 9500, at least 9750, or at least 10000-fold increased or elevated relative to one or more corresponding plant cells, plant tissues, or plants.

In other embodiments, increased or elevated expression, activity, and/or amount of a wbm protein in a plant cell, plant tissue, or plant may be an expression, activity, and/or amount or concentration of a wbm protein in a plant cell, plant tissue or plant, of at least a certain level.

In some embodiments, the expression of one or more transcripts encoding a wbm protein comprises at least 0.005%, at least 0.01%, at least 0.02%, at least 0.05%, at least 0.1%, at least 0.15%, at least 0.2%, at least 0.25%, at least 0.3%, at least 0.35%, at least 0.4%, at least 0.45%, or at least 0.5% of the total transcript expression of a plant cell, plant tissue, or plant.

Genetic Modification

In certain embodiments, the invention relates to a method for producing a plant or plant part with improved breadmaking properties, including the step of genetically modifying one or more plant cells or tissues, to produce a plant capable of producing a seed comprising an increased or elevated expression, activity and/or amount of a wbm protein of the invention, to thereby produce a plant or plant part with improved breadmaking properties.

In preferred embodiments the increased or elevated expression, activity and/or amount of a wbm protein of the seed is of the endosperm of said seed.

It is envisaged that in some particular embodiments, the step of genetic modification encompasses transformation of a plant cell or tissue with a genetic construct of the invention as hereinabove described.

As will be understood by one skilled in the art, transformation of a plant cell or tissue with a genetic construct may comprise "stable" transformation, or "transient" transformation.

"Stable" transformation may comprise the incorporation of a genetic construct into the genetic material of one or more plant cells or tissues, wherein the genetic material comprising the genetic construct can be inherited to the progeny of a plant produced from the plant cells or tissues.

"Transient" transformation may comprise the introduction of a genetic construct into one or more plant cells or plant tissues, without the introduction of said genetic construct into the genetic material of said cells or tissues. Suitably, the genetic construct may be expressed using the cellular machinery within one or more plant cells or tissues.

In one embodiment, the method of genetically modifying a plant, plant cell or plant tissue, includes the steps of:

(i) transforming a plant cell or tissue with a genetic construct comprising an isolated nucleic acid encoding a wbm protein of the invention, and/or a promoter or promoter-active fragment of the invention; and (ii) selectively propagating a genetically modified plant from a plant cell or tissue transformed in step (i).

Suitably, the plant cell or tissue used at step (i) may be a leaf disk, callus, meristem, hypocotyls, root, leaf spindle or whorl, leaf blade, stem, shoot, petiole, axillary bud, shoot apex, internode, cotyledonary-node, flower stalk or inflorescence tissue.

The plant cell or tissue may be obtained from any plant species including monocotyledon, dicotyledon, ferns and gymnosperms such as conifers, without being limited thereto.

Preferably, the plant is a dicotyledon or a monocotyledon, inclusive of crop plants such as legumes, cereals, and solanaceous plant species.

The plant may be, for example, a grass species of the family Poaceae; wheat or other cereals including maize, *sorghum*, barley, and rice; a leguminous species including beans and peanut; a solanaceous species including tomato and potato; or a model plant species including the model dicotyledonous species *Arabidopsis* and the model monocotyledonous species *Brachypodium distachyon*.

Persons skilled in the art will be aware that a variety of transformation methods are applicable to the method of the invention, such as *Agrobacterium tumefaciens*-mediated (Gartland & Davey, 1995, *Agrobacterium* Protocols (Humana Press Inc. NJ USA); U.S. Pat. No. 6,037,522; WO99/36637), microprojectile bombardment (Franks & Birch, 1991, Aust. J. Plant. Physiol., 18 471; Bower et al., 1996, Molecular Breeding, 2 239; Nutt et al., 1999, Proc. Aust. Soc. SugarCane Technol. 21 171), liposome-mediated (Ahokas et al., 1987, Heriditas 106 129), laser-mediated (Guo et al., 1995, Physiologia Plantarum 93 19), silicon carbide or tungsten whiskers-mediated (U.S. Pat. No. 5,302,523; Kaeppler et al., 1992, Theor. Appl. Genet. 84 560), virus-mediated (Brisson et al., 1987, Nature 310 511), polyethylene-glycol-mediated (Paszkowski et al., 1984, EMBO J. 3 2717) as well as transformation by microinjection (Neuhaus et al., 1987, Theor. Appl. Genet. 75 30) and electroporation of protoplasts (Fromm et al., 1986, Nature 319 791), all of which references are incorporated herein.

In one embodiment, the genetic construct may comprise a selection marker nucleic acid as hereinbefore described.

In another embodiment, a separate selection construct may be included at step (i), which comprises a selection marker nucleic acid.

The transformed plant material may be cultured in shoot induction medium followed by shoot elongation media as is well known in the art. Shoots may be cut and inserted into root induction media to induce root formation as is known in the art.

It will be appreciated that, as discussed hereinbefore, there are a number of different selection agents useful according to the invention, the choice of selection agent being determined by the selection marker nucleic acid used in the expression construct or provided by a separate selection construct.

The presence of a transgene or transgenic protein, such as a wbm protein, a nucleic acid encoding a wbm protein, and/or a wbm promoter or promoter-active fragment of the invention, may be detected in a plant cell, tissue, or plant by any of a range of methods known to those skilled in the art.

In one embodiment, wbm protein expression can be detected by an antibody specific for a wbm protein, such as an antibody of the invention as herein described:

(i) in an ELISA such as described in Chapter 11.2 of CURRENT PROTOCOLS IN MOLECULAR BIOLOGY Eds. Ausubel et al. (John Wiley & Sons Inc. NY, 1995) which is herein incorporated by reference; or (ii) by Western blotting and/or immunoprecipitation such as described in Chapter 12 of CURRENT PROTOCOLS IN PROTEIN SCIENCE Eds. Coligan et al. (John Wiley & Sons Inc. NY, 1997), which is herein incorporated by reference.

Protein-based techniques such as mentioned above may also be found in Chapter 4.2 of PLANT MOLECULAR BIOLOGY: A Laboratory Manual, supra, which is herein incorporated by reference.

It will also be appreciated that genetically modified or transgenic plants of the invention may be screened for the presence of mRNA corresponding to a transcribable nucleic acid and/or a selection marker nucleic acid. This may be performed by RT-PCR (including quantitative RT-PCR), Northern hybridization, and/or microarray analysis. For example, Southern hybridization and/or PCR may be employed to detect DNA (the wbm nucleic acids, transcribable nucleic acids and/or selection marker) in the genetically modified plant genome using primers such as described herein in EXAMPLE 3.

For examples of RNA isolation and Northern hybridization methods, the skilled person is referred to Chapter 3 of PLANT MOLECULAR BIOLOGY: A Laboratory Manual, supra, which is herein incorporated by reference. Southern hybridization is described, for example, in Chapter 1 of PLANT MOLECULAR BIOLOGY: A Laboratory Manual, supra, which is herein incorporated by reference.

A selectable marker as described herein is typically used to increase the number of positive transformants before assaying for transgene expression. However, positive transformants identified by PCR and other high throughput type systems (e.g., microarrays, high-throughput sequencing) enable selection of transformants without use of a selectable marker due to a large number of samples that may be easily tested. It may be preferred to avoid use of selectable markers in transgenic plants because of environmental concerns in relation to perceived accidentally release of the selectable marker nucleic acid into the environment. Herbicide resistance markers, e.g., against BASTA, and antibiotic resistance markers, e.g., against ampicillin, are a few selectable markers that may be of concern. PCR may be performed on thousands of samples using primers specific for the transgene or part thereof, the amplified PCR product may be separated by gel electrophoresis, coated onto multi-well plates and/or dot blotting onto a membrane and hybridized with a suitable probe, for example probes described herein including radioactive and fluorescent probes to identify the transformant.

Mutagenesis, Genome Editing

Another aspect of the invention relates to a method including the steps of:

(i) introducing one or more mutations into the genetic material of a plant; and (ii) selecting a plant capable of producing a seed comprising an elevated or increased concentration and/or activity of a wbm protein, to thereby produce a plant with improved breadmaking properties.

In preferred embodiments an increased or elevated expression, activity or concentration of a wbm protein of the seed is of the endosperm of said seed.

In certain preferred embodiments, mutations are introduced into a nucleic acid encoding a wbm protein of the invention, and/or an associated promoter or promoter active fragment, such as the promoter active fragments set forth in SEQ ID NOS:2-9.

The terms "mutant", "mutation" and "mutated" are used herein generally to encompass conservative or non-conservative nucleic acid base pair substitutions, deletions and/or insertions introduced into the genetic material of a plant. For example, mutations may be introduced into chromosomal DNA and genomic DNA, RNA such as unspliced and spliced mRNA, tRNA and other forms of genetic material as are known in the art.

Mutagenesis of the genetic material of a plant may result in introduction of mutations in one or a plurality of nucleic acid molecules. It will be appreciated that genome-wide mutagenesis of a plant is contemplated. In alternative embodiments, mutations can also be introduced or induced by targeting specific loci or regions. It will be appreciated that gain-of-function and loss-of-function mutations may be achieved as a result of mutagenesis as per the present invention, although without limitation thereto.

Mutations may be induced or introduced using either non-specific methods such as random mutagenesis or alternatively by using specific methods such as targeted mutagenesis. Induced mutations may include single- or multiple-nucleotide substitutions, deletions and/or insertions, either alone or in combination. Mutagenesis methods of the present invention are inclusive of in vitro, in vivo and in planta methodology.

Chemical mutagenesis is a useful method of genome-wide random mutagenesis methods using alkylating agents such as ethylmethanesulfonate (EMS) and dimethyl sulfate (DMS) or other chemical mutagens such as ethidium bromide, formic acid, hyrdazine, sodium bisulphite and diepoxybutane.

Physical mutagenesis using physical mutagens as for example irradiation using ionising radiation (such as β, γ or X-ray radiation), UV irradiation and fast neutron irradiation of seeds may also be used for genome-wide random mutagenesis. It will be appreciated by a person skilled in the art that the time and dosage of exposure of the plant or a part thereof, to a mutagen is dependent on the plant and mutagen that is used and can be readily determined by a skilled addressee.

Mutations may be introduced into nucleic acids by random or site-directed mutagenesis as are well known in the art. Non-limiting examples of nucleic acid mutagenesis methods are provided in Chapter 8 of CURRENT PROTOCOLS IN MOLECULAR BIOLOGY Eds Ausubel et al., (John Wiley & Sons, Inc. 1995-2008) and is incorporated herein by reference.

Random mutagenesis methods also include incorporation of dNTP analogs into nucleic acids (Zaccolo et al., 1996, J. Mol. Biol. 255 589) and PCR-based random mutagenesis such as described in Stemmer, 1994, Proc. Natl. Acad. Sci. USA 91 10747 or Shafikhani et al., 1997, Biotechniques 23 304, each of which references is incorporated herein. It is also noted that PCR-based random mutagenesis kits are commercially available, such as the Diversify™ kit (Clontech).

In certain embodiments, mutations produced by a nucleic acid sequence amplification-based technique are introduced into the genetic material of a plant.

As used herein, a "nucleic acid sequence amplification technique" includes but is not limited to polymerase chain reaction (PCR) as for example described in Chapter 15 of CURRENT PROTOCOLS IN MOLECULAR BIOLOGY Eds. Ausubel et al. (John Wiley & Sons NY USA 1995-2001) strand displacement amplification (SDA); rolling circle replication (RCR) as for example described in International Application WO 92/01813 and International Application WO 97/19193; nucleic acid sequence-based amplification (NASBA) as for example described by Sooknanan et al. 1994, Biotechniques 17 1077; ligase chain reaction (LCR) as for example described in International Application WO89/09385 and Chapter 15 of CURRENT PROTOCOLS IN MOLECULAR BIOLOGY supra; Q-β replicase amplification as for example described by Tyagi et al., 1996, Proc. Natl. Acad. Sci. USA 93 5395 and helicase-dependent amplification as for example described in International Publication WO 2004/02025.

Region-specific mutagenesis and directed mutagenesis using PCR may also be employed to construct nucleic acid mutants according to the invention. Oligonucleotide-mediated (or site-directed) mutagenesis may also be used. A non-limiting example of oligonucleotide-mediated site-directed mutagenesis procedures to introduce small clusters of point mutations throughout the target region is provided in Ausubel et al., supra. Briefly, mutations are introduced into a sequence by annealing a synthetic oligonucleotide containing one or more mismatches to the sequence of interest cloned into a single-stranded M13 vector. This template is grown in an *Escherichia coli* dut⁻ ung⁻ strain, which allows the incorporation of uracil into the template strand. The oligonucleotide is annealed to the template and extended with T4 DNA polymerase to create a double-stranded heteroduplex. Finally, the heteroduplex is introduced into a wild-type *E. coli* strain, which will prevent replication of the template strand due to the presence of apurinic sites (generated where uracil is incorporated), thereby resulting in plaques containing only mutated DNA. It is also noted that site-directed mutagenesis kits are commercially available, such as the QuikChange™ kit (Stratagene).

Alternatively, linker-scanning mutagenesis of DNA may be used to introduce clusters of point mutations throughout a sequence of interest that has been cloned into a plasmid vector. For example, reference may be made to Ausubel et al., supra, (in particular, Chapter 8, incorporated herein by reference) which describes a first protocol that uses complementary oligonucleotides and requires a unique restriction site adjacent to the region that is to be mutagenised. A nested series of deletion mutations is first generated in the region. A pair of complementary oligonucleotides is synthesised to fill in the gap in the sequence of interest between the linker at the deletion endpoint and the nearby restriction site. The linker sequence actually provides the desired clusters of point mutations as it is moved or "scanned" across the region by its position at the varied endpoints of the deletion mutation series.

Mutations may be induced or introduced by insertion of one or a plurality of nucleotides or base-pairs into the genetic material. Transposon and retrotransposon mutagenesis (for example as described in Walbot 2000, Curr Opin Plant Biol 3 103; U.S. Pat. No. 6,720,479; Voytas 1996, Genetics 142 569) are also contemplated as methods for insertional mutagenesis. Other methods of insertional mutagenesis include targeted methods such as homologous recombination and site-specific recombination. A non-limiting example of homologous recombination is the T-DNA system (for example as described in Wang et al. 2001, Gene 272 249; and Iida & Terada 2005, Plant Mol. Biol. 59 205). An example of site-specific recombination is the cre-lox recombination system of bacteriophage P1, which has been applied to promote recombination of specific locations on the genome of plants cells (for example, as described in U.S. Pat. No. 5,658,772).

Chimeric RNA/DNA oligonucleotide-directed gene targeting is also a useful technique for the generation of site-specific point mutations such as deletions, insertions and/or base changes in higher plants (see for example as described in Iida & Terada, 2005, Plant Mol. Biol. 59 205; and Rice et al., 2000, Plant Physiol, 123 427).

Mutations may also be introduced by deletional mutagenesis of one or a plurality of nucleotides, or a region of a genetic locus. For example, fast neutron deletion mutagenesis is contemplated by the present invention as a genome-wide deletional mutagenesis method and utilises fast neutron bombardment to create a random mutagenised populations of plants, and more particularly knockout mutations such as described Li et al., 2002, Comp. Funct. Genomics 3 158. It will be appreciated that targeted deletional mutagenesis may be achieved by using a variety of other nucleic acid based mutagenesis methods as herein described, such as, but not limited to oligonucleotide-based mutagenesis.

Targeting Induced Local Lesions in Genomes (otherwise referred to as "TILLING") is particularly amenable for random mutagenesis to generate point mutations in plants. TILLING combines traditional chemical mutagenesis following by high-throughput screening for point mutations. Reference is made to McCallum et al., 2000, Nat. Biotechnol. 18 455; Till et al., 2003, Methods Mol. Biol. 236 205; Henikoff et al., 2004, Plant Physiol. 135 630; and Till et al., 2003, Genome Res. 13 524 for non-limiting examples of TILLING methods applicable to the present invention. TILLING is also particularly amenable to high-throughput methodology, as described in Wang et al., 2012, Plant Biotechnol. J. 10 761, which provides non-limiting examples of high-throughput TILLING methods, technologies for the detecting of single-nucleotide differences and TILLING generally and is incorporated herein by reference.

In certain preferred embodiments, mutations are introduced into the genetic material of a plant via "genome editing".

"Genome editing" is a method for mutagenesis in which DNA is inserted, substituted, modified, or deleted from the genetic material of an organism in a targeted manner, using engineered nucleases.

Methods for genome editing include "zinc finger nuclease" methods, as described for example by Miller et al., 2007, Nat. Biotech. 25 778; "CRISPR/Cas" methods, as described for example by Cong et al., Science 339 819; and "TALEN" methods, as described for example by Bedell et al., Nature 491, 114.

As will be understood by those skilled in the art, genome editing comprises the transformation of a cell or tissue with one or more genetic constructs facilitating the expression of:

(i) one or more DNA nucleases; and (ii) one or more molecules that guide the cleavage of DNA at a targeted region within the genetic material of an organism by said nuclease(s).

Targeted DNA breaks are thereby induced in the genetic material of the organism. Said targeted DNA breaks are generally double stranded DNA breaks, although without limitation thereto.

In embodiments of genome editing wherein a zinc finger nuclease method is used, the one or more molecules that guide the cleavage of DNA at a targeted region within the genetic material of an organism by said nuclease(s) are proteins comprising a zinc finger DNA-binding domain. Generally, a plurality of said proteins are fused to said nuclease(s), and the plurality of zinc finger DNA-binding domains of said proteins bind with at least partial specificity to the targeted region, and thereby induce cleavage of the targeted region by said nuclease(s).

In embodiments of genome editing wherein a TALEN method is used, the one or more molecules that guide the cleavage of DNA at a targeted region within the genetic material of an organism by said nuclease(s) are proteins comprising a transcription activator-like effector DNA-binding ("TALE") domain. Generally, a plurality of said proteins are fused to said nuclease(s), and the plurality of TALE DNA-binding domains of said proteins bind with at least partial specificity to the targeted region, and thereby induce cleavage of the targeted region by said nuclease(s).

In embodiments of genome editing wherein a CRISPR/Cas method is used, the nuclease is a CRISPR-associated (Cas) nuclease, and the one or more molecules that guide the cleavage of DNA at a targeted region is a "guide" RNA molecule (or "gRNA") with homology to the targeted region. Generally, the gRNA molecule forms a complex with the Cas nuclease and guides binding of the Cas nuclease to the targeted region with at least partial specificity, and thereby induces cleavage of the targeted region by said Cas nuclease.

It will be further understood that targeted DNA breaks induced during genome editing can facilitate non-homologous end joining or homology-dependent repair.

"Non-homologous end joining" is a cellular mechanism for DNA break repair wherein cleaved DNA ends are ligated, which is typically "error prone", i.e. introduces nucleotide sequence variation, e.g. insertions or deletions, at the site of the DNA break. DNA breakage followed by error-prone non-homologous end joining induced by genome editing can be used to inactivate targeted regions within the genetic material of organisms including plants and animals (as described for example by Gaj et al., 2013 Trends Microbiol. 31 397).

"Homology-dependent repair" is a cellular mechanism for DNA break repair wherein a nucleic acid possessing homology to the region surrounding a DNA break is used as a template for repair of the DNA break. Genome editing can be used to introduce nucleic acid variants into targeted regions within the genetic material of organisms including plants and animals (as described for example by Gaj et al., 2013 Trends Microbiol 31 397) by inducing DNA breakage followed by homology-dependent repair in the presence of a "donor molecule", wherein said donor molecule comprises homology to the region surrounding the DNA break.

As will be understood by those skilled in the art, genome editing comprising homology-dependent repair can be used for "allele replacement", wherein a nucleic acid of the genetic material of an organism is "substituted", "exchanged" or "replaced" with a variant of said nucleic acid.

In certain preferred embodiments of the invention, genome editing comprising allele replacement is used to substitute a nucleic acid encoding a non-functional wbm protein, or a wbm protein possessing relatively decreased activity, with a wbm protein of the invention such as set forth in SEQ ID NO:1 that is functional or possesses relatively increased activity.

In certain other preferred embodiments of the invention, genome editing comprising allele replacement is used to substitute a weak or inactive promoter or promoter-active fragment of the invention, such as a promoter of the invention set forth in SEQ ID NOS:2-9, with an active wbm promoter or promoter-active fragment, such as a promoter or promoter-active fragment comprising one or more nucleotide sequence additions, deletions and/or substitutions to any one of SEQ ID NOS:2-9 that relatively increase or elevate the activity of said promoter or promoter active fragment.

As will be understood by those skilled in the art, in embodiments relating to genome editing, a plant with one or more mutations resulting from genome editing of the plant may be selected, wherein the plant lacks the one or more genetic constructs used for genome editing. It will be further understood that said plant may be considered "non-genetically modified", "non-GM", or "non-GMO" from a regulatory standpoint.

Propagation by Crossing

Yet another aspect of the invention relates to a method for improving the breadmaking properties of a plant or plant part including the steps of:

(i) identifying one or more plants capable of producing a seed comprising an increased or elevated expression, activity and/or amount of a wbm protein of the invention;

(ii) crossing the one or more plants capable of producing a seed comprising an increased or elevated expression, activity, and/or amount of the protein of the first aspect together, and/or with one or more other plants; and (iii) selecting one or more progeny plants capable of producing a seed comprising an increased or elevated expression, activity and/or amount of a wbm protein of the invention, to thereby produce a plant or plant part with improved breadmaking properties.

In preferred embodiments an increased or elevated expression, activity or amount of a wbm protein of the seed is of the endosperm of said seed.

In certain embodiments, one of the one or more plants used in crossing is not capable of producing a seed comprising an increased or elevated expression, activity and/or concentration of a wbm protein of the invention. Preferably said plant comprises one or more other beneficial or desirable characteristics.

Certain non-limiting examples of said one or more other beneficial or desirable characteristics can include, although without limitation thereto: seed or grain quality (including breadmaking) properties, stress tolerance, for example abiotic stress tolerance such as drought or salt resistance, and biotic stress resistance such as resistance to disease; seed or grain yield; vigour; plant height; nutritional properties; and seed or grain dormancy.

Preferably, one or more progeny plants are selected that is capable of producing a seed comprising an increased or elevated expression, activity and/or concentration of a wbm protein of the invention, and comprises at least one of said one or more other beneficial or desirable traits.

In certain preferred embodiments wherein the plant is wheat, preferably at least one of the one or more plants capable of producing a seed comprising an increased or elevated expression, activity or concentration of a wbm protein of the invention is selected from the group consisting of: Sunco, Gregory, Bob White 26, Batavia, Banks, Janz, Condor, Cook, Bounty, Baxter, Oxley, Wylie, Kidman, Hume, Chara, and Leichhardt.

In certain other preferred embodiments, the one or more plants capable of producing a seed comprising an increased or elevated expression, activity or amount of a wbm protein comprises a wbm allele which comprises one or more of the nucleotide sequences set forth in SEQ ID NO:16 and SEQ ID NO:18.

In certain other preferred embodiments, the one or more plants capable of producing a seed comprising an increased or elevated expression, activity or amount of a wbm protein comprises a promoter or promoter-active fragments comprising one or more nucleotide sequence additions, deletions and/or substitutions to any one of SEQ ID NOS:2-9 that relatively increase or elevate the activity of said promoter or promoter active fragment, wherein the nucleotide sequence of said modified promoter or promoter active fragment is not SEQ ID NO:10

In another preferred embodiments, the one or more plants capable of producing a seed comprising an increased or elevated expression, activity or amount of a wbm protein comprises a promoter or promoter-active fragment set forth in SEQ ID NO:10.

Certain embodiments of this aspect comprise the use of one or more plants wherein genome editing has been performed. As will be understood by those skilled in the art, in embodiments wherein a genome edited plant is produced by transformation with one or more genetic constructs, the progeny of said genome edited plant may be selected to lack said genetic construct(s), due to segregation of the genetic construct(s) amongst said progeny. Suitably, said progeny may be selected to possess one or more mutations resulting from said genome editing. Furthermore, the skilled person will appreciate that genome editing using transient transformation (as hereinbefore described) can be performed, wherein mutations are induced without stable incorporation of the genetic construct into the genome edited plant.

As hereinbefore described, it will be understood that a plant with one or more mutations resulting from genome editing of the plant, wherein the plant lacks the one or more genetic constructs used for genome editing, may be considered "non-genetically modified", "non-GM", or "non-GMO" from a regulatory standpoint.

Method of Making Bread

In another aspect, the invention provides a method of making bread, the method including the step of processing a seed with improved breadmaking properties of the invention, to thereby produce bread.

According to this aspect, bread may be produced by any of the range of methods known in the art. The skilled person is referred to Hamelman, 2012, *"Bread: A Baker's Book of Techniques and Recipes"* ($2^{nd}$ Edition) John Wiley & Sons, incorporated herein by reference.

It will be understood that according to this aspect, processing of a seed with improved breadmaking properties may comprise "grinding" or "milling" said seed to produce a flour. Suitably, said processing further comprises the steps of 1) combining said flour with one or more other ingredients (e.g. water, yeast, salt, and one or more flavouring agents, although without limitation thereto) to produce a "paste" or "dough"; and 2) heating (e.g. baking) said paste or dough to produce the bread.

wbm Antibodies

In yet another aspect of the invention, there is provided an antibody or antibody fragment that binds or is raised against an isolated wbm protein of the invention. Suitably the antibody or antibody fragment shows at least partial specificity for said wbm protein.

Anti-wbm protein antibodies of the invention may be polyclonal or monoclonal. Well-known protocols applicable to antibody production, purification and use may be found, for example, in Chapter 2 of Coligan et al., CURRENT PROTOCOLS IN IMMUNOLOGY (John Wiley & Sons NY, 1991-1994) and Harlow, E. & Lane, D. *Antibodies: A Laboratory Manual*, Cold Spring Harbor, Cold Spring Harbor Laboratory, 1988, which are both herein incorporated by reference.

Generally, antibodies of the invention bind to or conjugate with a polypeptide, fragment, variant or derivative of the invention. For example, the antibodies may comprise polyclonal antibodies. Such antibodies may be prepared for example by injecting a polypeptide, fragment, variant or derivative of the invention into a production species, which may include mice, rabbits or goats, to obtain polyclonal antisera. Methods of producing polyclonal antibodies are well known to those skilled in the art. Exemplary protocols that may be used are described for example in Coligan et al., CURRENT PROTOCOLS IN IMMUNOLOGY, supra, and in Harlow & Lane, 1988, supra.

In lieu of the polyclonal antisera obtained in the production species, monoclonal antibodies may be produced using the standard method as for example, described in an article by Köhler & Milstein, 1975, Nature 256, 495, which is herein incorporated by reference, or by more recent modifications thereof as for example, described in Coligan et al., CURRENT PROTOCOLS IN IMMUNOLOGY, supra by immortalizing spleen or other antibody producing cells derived from a production species which has been inoculated with one or more of the polypeptides, fragments, variants or derivatives of the invention.

The invention also includes within its scope antibodies that comprise Fc or Fab fragments of the polyclonal or monoclonal antibodies referred to above. Alternatively, the antibodies may comprise single chain Fv antibodies (scFvs) against the peptides of the invention. Such scFvs may be prepared, for example, in accordance with the methods described respectively in U.S. Pat. No. 5,091,513, European Patent No 239,400 or the article by Winter & Milstein, 1991, Nature 349 293, which are incorporated herein by reference.

In order that the invention may be readily understood and put into practical effect, particular preferred embodiments will now be described by way of the following non-limiting examples.

EXAMPLES

Example 1. Identification of wbm

Material and Methods
Long-SAGE libraries of wheat seed (*Triticum aestivum* cvs. Banks and Kite) were constructed as published in McIntosh et al., 2007, incorporated herein by reference. For the present study, tags were sorted based on increasing order of abundance, and the first one hundred abundant SAGE tags were subsequently annotated via BlastN comparisons with Genbank EST sequences, and verified against results generated using HarvEST sequence clusters.
Results
Comparison of Long-SAGE gene expression data in the developing seed of Banks (good bread quality) and Kite (poor bread quality) revealed a highly differentially expressed gene tag, "tag-A", set forth in SEQ ID NO:11. This gene, expressed specifically in Banks, was found predominantly during the critical mid-stages of seed development (FIG. 2).

The sequence corresponding to tag-A was subjected to BLAST analysis to Unigenes in NCBI. Identified Unigene cluster sequences were then subjected to BlastN, MegaBlast and Discontiguous-MegaBlast analysis to the non-redundant nucleotide database in NCBI, and to NCBI ET sequences. tag-A was also subjected for homology analysis to a cDNA library prepared in our laboratory using the same RNA isolated from 14 dpa developing seeds and used for the LongSAGE experiment.

Figure 3:
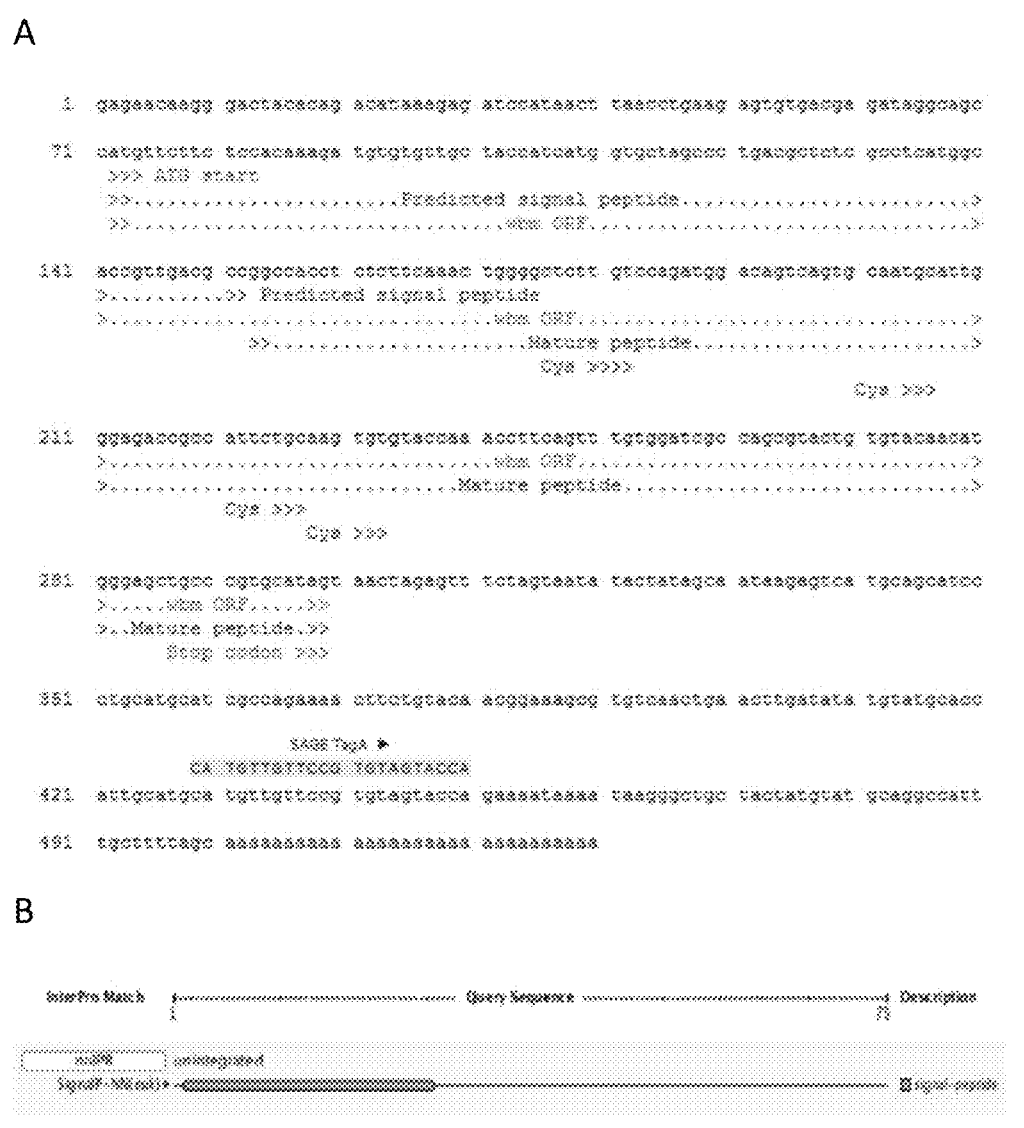

The analyses performed indicate that the gene, set forth in SEQ ID NO:23, corresponding to tag-A encodes a novel small protein (FIGS. 1 and 3), set forth in SEQ ID:1, that had not been characterized in previous studies of wheat quality. This gene has been named "wheat breadmaking" (wbm), encoding the protein wbm.

wbm appears to be a small protein with a mature polypeptide of 48 amino acids (aa) and a 27 amino acid signal peptide (FIG. 3). The predicted mature protein of 48 aa includes four cysteine residues with a distribution pattern of CYS-(X=7)-CYS-(X=6)-CYS-(X=1)-(CYS), where X represents any other aa residue. Similarities with other protein sequences (~30%) found using BlastX and tBlastX were not high enough to assign a putative function with any degree of confidence. However, the predicted ORF was found to contain an ML domain which is a MD-2-related lipid-recognition domain that is present in several proteins of unknown function in plants, animals and fungi. These proteins are predicted to mediate diverse biological functions through interaction with specific lipids (Marchler-Bauer et al., 2009). Thus, due to the lack of significant homology to any gene or protein of known function, a putative function for wbm could not be assigned. However, motif and structural prediction of the wbm sequence via PredictProtein indicates that wbm probably encodes a small microbody-associated protein. The biological function of this protein is not obvious, however the protein could have many roles in baking. A lipid interaction suggests a role in complexing with lipids in baking or in linking lipids and proteins. The role of lipids in baking is poorly understood (MacRitchie et al., 1973; MacRitchie et al., 1977).

Importantly, the four cysteine residues (FIG. 3) provide an opportunity for wbm to influence bread quality by interacting in the formation of disulphide bonds in gluten. Unlike other cereals, wheat has unique proteins that allow the production of bread (Cauvain, 2012). When wheat flour is mixed with water, proteins in the wheat support the formation of a unique elastic mass or dough. The wheat seed proteins in dough form a complex called gluten responsible for the elasticity of the dough (Shewry, 1999). These viscoelastic properties allow wheat dough to expand by trapping bubbles of carbon dioxide produced by yeast fermentation in the dough. Baking stabilizes the resulting risen dough to produce bread and other related products with extensive air spaces resulting in the attractive texture of leavened bread (Chantret, 2005). The formation of gluten is crucial for the breadmaking process and this novel characteristic of wheat is central to its widespread consumption. Traditional studies of wheat quality have focused on the high molecular weight proteins, especially the glutenins and the gliadens (Payne et al., 1987; Burnouf & Bouriquet, 1980; Lawrence et al., 1987; Cressey et al., 1987; Moonen et al., 1982). The small wbm protein may have been overlooked in classical wheat protein studies designed to separate and characterize much larger proteins.

The formation of gluten is usually explained by the formation of disulphide bonds between cysteine resides in the wheat proteins generating a very large elastic macromolecular network in the dough (Shewry et al. 1992; Shewry and Tatham, 1997; Shewry et al. 2003; Masci et al. 1993). Small cysteine rich proteins, like wbm, may be able to facilitate this process by contributing to cross linking proteins in the network.

Example 2. Gene Expression Analysis of Diverse Wheat Genotypes

Material and Methods
Plant Material
Seeds of wheat genotypes were sourced from the Australian Winter Cereal Collection, Tamworth, Australia. Australian wheats are graded and classified for end use by Wheat Classification Council, which is comprises a committee to the Board of Wheat Quality Australia. Wheat Quality Australia relies on data generated from the National Variety Trials (NVT) to classify new varieties. We obtained data pertaining to wheat genotypes good or poor for breadmaking based on annual NVT data released by the Grains Research and Development, and this can be accessed from the GRDC and DEEDI websites at daff/qld.gov. au/plants/field-crops-and-pastures/broadacre-field-crops/wheat/wheat varieties and grdc.com.au/Research-and-Development/National-Variety-Trials/Crop-Variety-Guides#Queensland, incorporated herein by reference. Industry ratings of wheat genotypes as good, acceptable or excellent for bread making was used to identify and group genotypes in this study as good for bread making. Similarly, wheat genotypes with industry rating of poor or marginal for bread making baking was used to identify and group genotypes in this study as poor for bread making.

Grains Research and Development, and this can be accessed from the GRDC and DEEDI websites at <http://www.daff.qld.gov.au/plants/field-crops-and-pastures/broadacre-field-crops/wheat/wheat-varieties> and <http://www.grdc.com.au/Research-and-Development/National-Variety-Trials/Crop-Variety-Guides#Queensland>, incorporated herein by reference. Industry ratings of wheat genotypes as good, acceptable or excellent for bread making was used to identify and group genotypes in this study as good for bread making. Similarly, wheat genotypes with industry rating of poor or marginal for bread making baking was used to identify and group genotypes in this study as poor for bread making.

Seeds were germinated either in a glasshouse or in a growth cabinet with 12 hrs of light and at day and night temperatures of 20° C. and 18° C., respectively. Seeds corresponding to 14 and 30 days post anthesis (dpa) seeds were collected as follows. Plants were tagged when awns were first visible at the flag leaf sheath as follows; date of awn observance, date of anthesis as +4 days from date of awn observance, dates for 14 and 30 days post anthesis as +14 and +30 days from date of anthesis respectively. Furthermore, spikes ready for harvest (based on 14 or 30 dpa tag dates) were checked if the immature embryo corresponded to a 14 dpa or 30 dpa immature embryos as follows. Developing seeds were harvested and the embryo was gently excised and visually observed to match a 14 or 30 dpa immature embryo. Spikes were harvested, and the top and bottom half form the centre of the spike was cut off, and then snap frozen in liquid nitrogen. While under liquid nitrogen, developing seeds from four or five spikes were then separated and stored at −70° C. until pulverised using a tissue lyser (Qiagen, USA) (Furtado 2014) and processed for RNA isolation.

RNA Isolation

Total RNA was isolated using a Trizol protocol (Invitrogen, Carlsbad, USA) as published elsewhere (Furtado 2014). Total RNA quality and concentration were determined using the RNA 6000 Pico kit (Agilent, Santa Clara, USA) on a 2100 Bioanalyzer (Agilent Technologies, Inc, Santa Clara, Calif., USA).

RNA-Seq

Sequencing was outsourced to Southern Cross Plant Genomics, Lismore, Australia, on the Illumina GAIIx system and all steps were followed as per the manufacturer's recommendation. NGS sequencing of cDNA from aleurone and endosperm tissue was carried out to obtain 75 bp paired reads, while all other NGS sequencing was carried out to obtain 100 bp paired end reads. All NGS data (as 75 bp and as 100 bp paired end reads) was imported into CLC Genomics Workbench (CLC-GW) ver 7.0.4 (CLC bio, Aarhus, Denmark) and trimmed using default parameter.

Trimmed sequences were processed for RNA-Seq analysis using the RNA-Seq tool within the CLC-GW platform. The unannotated Triticum aestivum Gene Index (TaGI) was used as reference sequences. TaGI consists of 221,925 tentative consensus sequences (TC) and derived from the DFCI Release 12.0 (The Computational Biology and Functional Genomics Laboratory, Dana Farber Cancer Institute and Harvard School of Public Health). Mapping parameters used were 0.9 for minimum length fraction, 0.8 for minimum similarity fraction and selecting the "include broken pairs" counting scheme.

Expression values for each gene were normalised as Reads per Kilobase per million reads mapped to DFCI (RPKM). Based on BLAST analysis, TC420043 in TaGI was found to correspond to wbm. Expression of wbm using RNA-Seq analysis was thus determined by extracting and counting reads which mapped to the tentative consensus TC420043 in TaGI. Statistical analysis of the RNA-Seq data to identify differentially expressed genes was carried out using the "Empirical analysis of Differential Gene Expression" (Robinson & Smyth, 2008; Robinson et al., 2010) a tool within the CLC-WB, with tag-wise dispersions estimated selected and p-values corrected for false discovery rate.

Results

RNA-Seq analysis at 14 and 30 days post anthesis (dpa) in 35 diverse wheat genotypes identified a number of differentially expressed genes (FDR $p<0.01$); 82 at 14 dpa and 925 at 30 dpa with 51 genes common at both time points. The wbm gene was the most significant differentially expressed gene at both time points with an up-regulated expression fold change of 1377 and 3224 in good breadmaking versus poor breadmaking genotypes at 14 and 30 dpa respectively.

Figure 4:
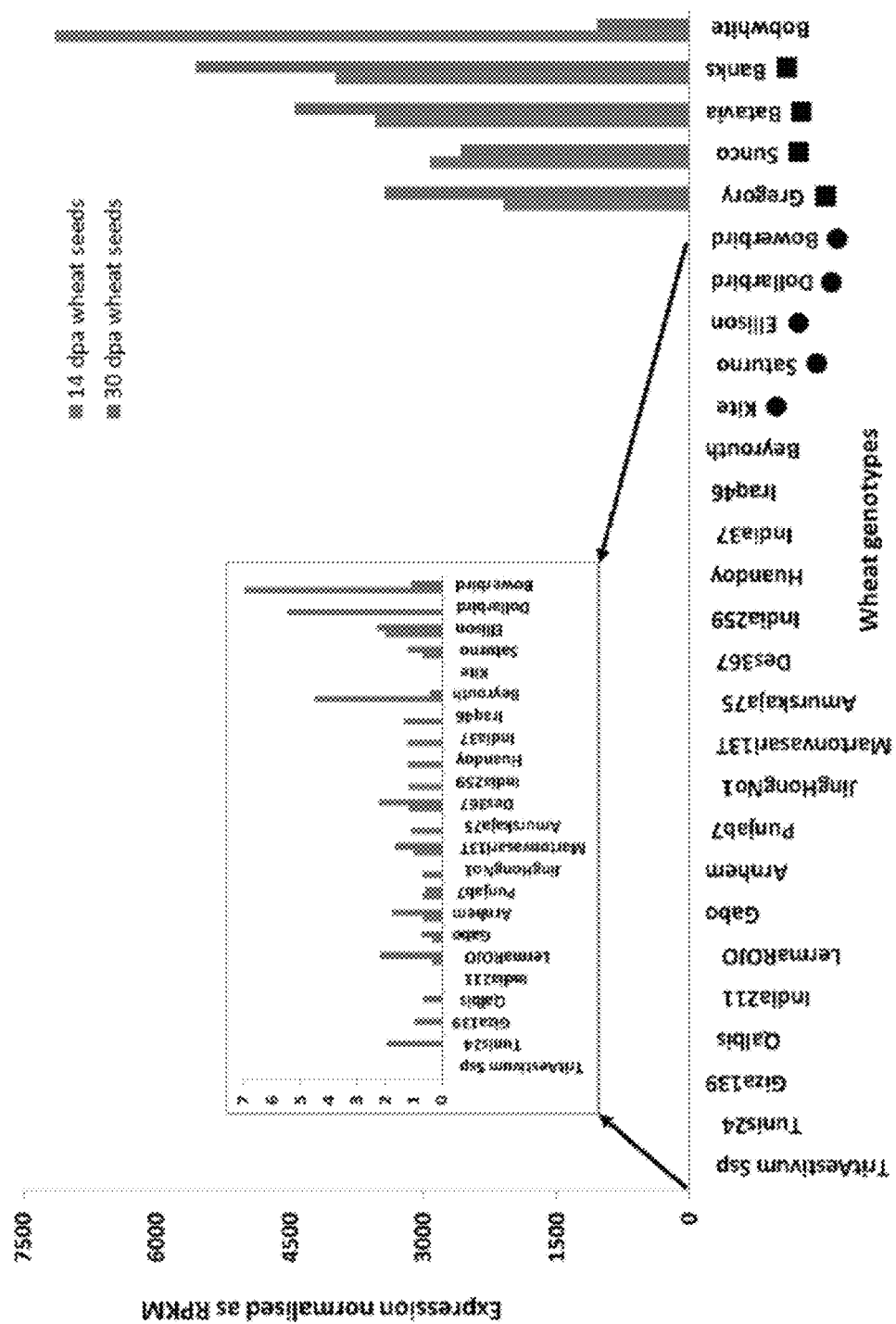
FIG. 4 sets out the transcript profiles of wbm genes in developing seeds of several wheat cultivars at 14 and 30 days post anthesis (dpa) based on RNA-Seq analysis. Total RNA was extracted from whole developing cDNA prepared, and sequenced using an Illumina analyser. Expression levels are given as 'Reads per Kilobase of Transcript per Million Reads Mapped' (RPKM) (inset is a magnified view so that lower expression levels can be observed). Circle and square symbols represent genotypes known to be poor and good for breadmaking, respectively.

The expression of the wbm gene in the 35 diverse wheat genotypes revealed either very high or very low expression (FIG. 4). All genotypes with high expression (except cv. Bobwhite-26 labelled as "Bobwhite" in FIG. 4 where the breadmaking quality is not known) had good bread making quality. This was a very highly expressed gene in five genotypes at 14 dpa with over 2000-7000 normalised read counts expressed as Reads per Kilobase per Million reads (RPKM) in these genotypes and equating to between 0.2-0.4% of total gene expression in developing seed and contrasting with only 0-7 RPKM of data in the other 23 genotypes tested. This is a remarkable difference between the genotypes as the wbm gene was the most highly expressed in some genotypes but had no, or virtually no, detectable expression in others providing an extreme example of differential expression between genotypes. In addition, this high level of differential expression of the wbm gene continued at 30 dpa (FIG. 4).

Example 3. Allelic Variation in wbm Genes

Material and Methods

Plant Material

Plant material and characterisation of breadmaking quality was as for EXAMPLE 1, above.

DNA Isolation

DNA was isolated from 10 to 15 day old seedlings of wheat according to the method of Furtado (2014).

Identification of 5' and 3' wbm CDS Variants

5' and 3' wbm CDS fragment variants from a range of wheat genotypes were identified from RNA-Seq reads, obtained as outlined in EXAMPLE 2 above.

Isolation of the 5'-upstream Region of the wbm Genes

Inverse PCR by "Genome Walking" was used to isolate the 5'-upstream regions of the NW gene using the Universal Genome Walker kit (Clontech, USA). Four Genome Walker (GW) libraries generated using DNA from wheat cvs. Banks and Kite, were used as template in a PCR reaction. Primers combinations of AP1 (supplied with kit) and NW1, set forth in SEQ ID NO:19; and AP2 (supplied with kit) and NW2, set forth in SEQ ID NO:20, were used in the primary and nested PCR respectively. Selected amplified fragments were cloned into pGEMT-easy vector (Promega, USA) and plated in ampicillin resistant plates as per the manufacturer's recommendation. Using blue/white screening, five colonies derived from cloning each PCR fragment were selected for plasmid preparation followed by sequencing using M13F/M13R as recommended by the manufacturer.

Sequence Analysis

Sequence analysis was carried out using Clone Manager 9 (Sci-Ed, Cary, N.C., USA) and Chromas Pro (Technelysium, Qld, Australia).

PCR to Detect Presence of the Active wbm Promoter

PCR screening of plants to identify the GWSeqVar3 promoter was carried out using purified genomic DNA from seedling/leaf tissue using primers NWPFor, set forth in SEQ ID NO:21, and NWPRev, set forth in SEQ ID NO:22 to generate a 961 bp fragment. PCR reaction for 10 cycles commenced with denaturing at 94° C. for 30 s, followed by annealing at 45° C. for 30 s and extension at 72° C. for 2 min and then for 25 cycles with denaturing at 94° C. for 30 s, followed by annealing at 50° C. for 30 s and extension at 72° C. for 2 min.

Transformation of Wheat and Maize

Wheat transformation was carried out by particle bombardment as per Vasil and Vasil 2006, incorporated herein by reference, and maize transformation by *Agrobacterium*-mediated transformation Vega et al. 2008, incorporated herein by reference.

Results

Figure 5:
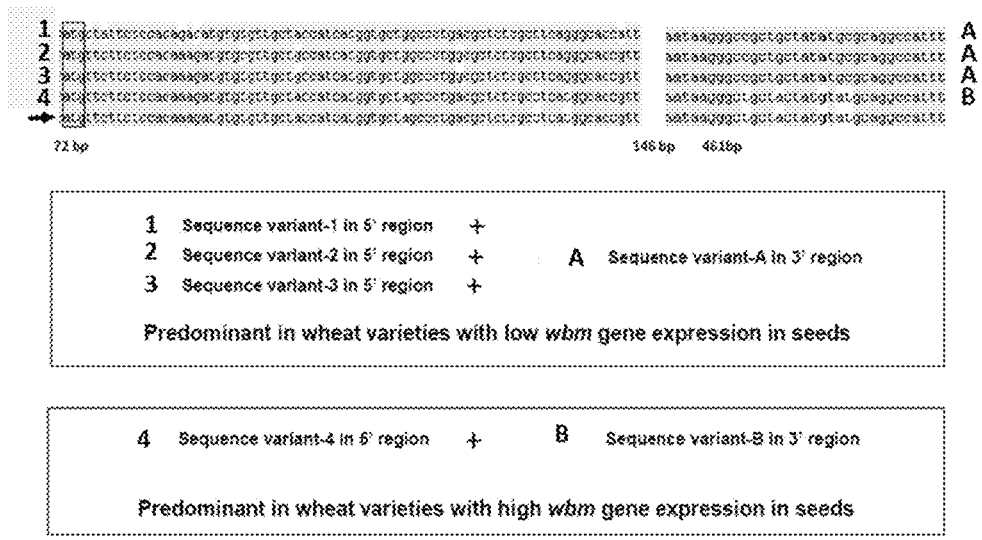
FIG. 5 sets out cDNA nucleotide sequence variants at the 5' ends (SEQ ID NOS: 13-16, respectively), and 3' ends (SEQ ID NOS:17-18) of the CDS of wbm genes. 1, 2, 3, and 4 indicate 5' CDS sequence variants Sequence variant-1 (SEQ ID NO:13), Sequence variant-2 (SEQ ID NO:14), Sequence variant-3 (SEQ ID NO:15), and Sequence variant-4 (SEQ ID NO: 16), respectively. A and B indicate 3' CDS sequence variants Sequence variant-A (SEQ ID NO: 17) and Sequence variant-B (SEQ ID NO: 18), respectively. Wheat varieties showing low or high wbm gene expression had specific combinations of sequence variants in the 5' and 3' region of the consensus cDNA sequence. Base pair positions are in relation to SEQ ID NO:23. Closed box indicates ATG start site.

Analysis of the allelic variation in the wbm gene identified several variants in the 5' and 3' region of the gene, some of which are non-conservative (FIG. 5). 5' cDNA nucleotide sequence variants "Sequence variant-1", "Sequence variant-2", "Sequence variant-3" and "Sequence variant-4" are set forth in SEQ ID NOS:13-16, respectively. 3' cDNA nucleotide sequence variants "Sequence variant-A" and "Sequence variant-B" are set forth in SEQ ID NOS:17-18, respectively. Wheat varieties showing low or high wbm gene expression had specific combinations of these sequence variants in the 5' and 3' region of the consensus cDNA sequence (FIG. 6), with varieties showing high wbm gene expression having Sequence variant-4 in the 5' region and Sequence variant-B in the 3' region.

Allelic variation in 5' promoter-active fragment sequences of wbm genes in Banks (good breadmaking properties) and Kite (poor breadmaking properties) was also identified (FIG. 7). Promoter variants “GWSeqVar3 Ba-B2B” (referred to herein as GWSeqVar3) (set forth in SEQ ID NO:10) and “GWSeqVarl Ki-K3A”, “GWSeqVarl Ba-B3A”, “GWSeqVar5 Ki-K1B”, “GWSeqVar4 Ki-K4B”, GWSeqVar4 Ba-B2A", “GWSeqVar6 Ba-B1A”, “GWSeqVar2 Ki-K2A”, and “GWSeqVar2 BaB4A” are set forth in SEQ ID NOS: 2-9. A ClustalW alignment of these promoter sequence variants identified sequence polymorphism that was present in GWSeqVar3 but not in any of the sequences set forth in SEQ ID NOS:2-9 (FIG. 16).

Based on PCR screening (FIG. 8) GWSeqVar3 was present in Banks and Bob White (high wbm expression), but not Kite (low wbm expression). PCR analysis was then expanded to 49 genotypes. For 27 genotypes the GWseqVar3 variant was absent and these genotypes had low wbm gene expression, whilst for seven genotypes the GWseqVar3 variant was present and these genotypes had high wbm gene expression) (FIG. 9). For the remaining genotypes, gene expression data has not yet been obtained. Additionally, GWSeqVar3 was found in 16 genotypes all known to have good bread making quality but none of the genotypes known to have poor breadmaking quality were found to possess GWSeqVar3 (FIG. 9).

The GWSeqVar3 promoter sequence of this highly expressing variant of the gene includes putative “TATA-box” and “CAAT-box” sites (FIG. 10) and was used to drive reporter gene expression in maize and wheat. Analysis of the transgenic maize plants demonstrated high levels of seed specific expression (FIG. 11, FIG. 12, and FIG. 13). Analysis of transcripts from aleurone and starchy endosperm suggest that the expression was substantially specific to the starchy endosperm (FIG. 14).

REFERENCES

Burnouf, T. & Bouriquet, R. Glutenin subunits of genetically related European hexaploid wheat cultivars: their relation to breadmaking quality. *Theor. Appl. Genet.* 58, 107-111 (1980).

Cauvain, S. P. *Breadmaking: Improving Quality*. Second edn, 4 (Woodhead Publishing Ltd, 2012).

Chantret, N. et al. Molecular basis of evolutionary events that shaped the hardness locus in diploid and polyploid wheat species (Triticum and Aegilops). *Plant Cell* 17, 1033-1045, doi:10.1105/tpc.104.029181 (2005).

Cressey, P. J., Campbell, W. P., Wrigley, C. W. & Griffin, W. B. Statistical correlations between quality attributes and grain-protein composition for 60 advances lines of crossbred wheat. *Cereal Chemistry* 64, 299-301 (1987).

Furtado, A. in Cereal Genomics Vol. 1099 Methods in Molecular Biology (eds Robert J. Henry & Agnelo Furtado) Ch. 1, 1-5 (Humana Press, 2014).

Lawrence, G. J., Moss, H. J., Shepherd, K. W. & Wrigley, C. W. Dough quality of biotypes of eleven australian wheat cultivars that differ in high-molecular-weight glutenin subunit composition. *Journal of Cereal Science* 6, 99-101 (1987).

MacRitchie, F. Flour lipids and their effects in baking. *J. Sci. Food Agric.* 28, 53-58, doi:10.1002/jsfa.2740280108 (1977).

MacRitchie, F. & Gras, P. W. The role of flour lipids in Baking. *Cereal Chem.* 50, 292-303 (1973).

Marchler-Bauer, A. et al. CDD: specific functional annotation with the Conserved
Domain Database. *Nucleic Acids Res.* 37, 205-210 (2009).

Masci, S. et al. D-Glutenin Subunits: N-Terminal Sequence and Evidence for the Presence of Cysteine. *Cereal Chemistry* 70, 518-585 (1993).

Moonen, J. H. E., Scheepstra, A. & Graveland, A. Use of the SDS-sedimentation test and SDS-polyacrylamidegel electrophoresis for screening breeder's samples of wheat for bread-making quality. *Euphytica* 31, 677-690, doi: 10.1007/bf00039206 (1982).

Payne, P. I., Nightingale, M. A., Krattiger, A. F. & Holt, L. M. The relationship between HMW glutenin subunit composition and the bread-making quality of British-grown wheat varieties. *J. Sci. Food Agric.* 40, 51-65, doi:10.1002/jsfa.2740400108 (1987).

Robinson, M. D., McCarthy, D. J. & Smyth, G. K. edgeR: a Bioconductor package for differential expression analysis of digital gene expression data. Bioinformatics 26, 139-140, doi:10.1093/bioinformatics/btp616 (2010).

Robinson, M. D. & Smyth, G. K. Small-sample estimation of negative binomial dispersion, with applications to SAGE data. Biostatistics 9, 321-332, doi:10.1093/biostatistics/kxm030 (2008).

Shewry, P. R. et al. The high molecular weight subunits of wheat glutenin and their role in determining wheat processing properties. *Advances in food and nutrition research* 45, 219-302 (2003).

Shewry, P. R., Halford, N. G. & Tatham, A. S. High molecular weight subunits of wheat glutenin. *Journal of Cereal Science* 15, 105-120, doi:10.1016/s0733-5210(09)80062-3 (1992).

Shewry, P. R. & Tatham, A. S. Disulphide bonds in wheat gluten proteins. *Journal Of Cereal Science* 25, 207-227 (1997).

Shewry, P. R. & Tatham, A. S. *The characteristics, structures and evolutionary relationships of prolamins*. (Kluwer Academic Publishers, 1999).

Vasil, I. K. & Vasil, V. Transformation of wheat via particle bombardment Methods in Molecular Biology 318, 273-283 (2006).

Vega, J. M., Yu, W., Kennon, A. R., Chen, X. & Zhang, Z. J. Improvement of *Agrobacterium*-mediated transformation in Hi-II maize (*Zea mays*) using standard binary vectors. Plant Cell Rep 27, 297-305, doi:10.1007/s00299-007-0463-z (2008).

Throughout the specification, the aim has been to describe the preferred embodiments of the invention without limiting the invention to any one embodiment or specific collection of features. Various changes and modifications may be made to the embodiments described and illustrated without departing from the present invention.

The disclosure of each patent and scientific document, computer program and algorithm referred to in this specification is incorporated by reference in its entirety.

The invention claimed is:

1. A genetic construct comprising a nucleic acid comprising:
   (a) a polynucleotide sequence encoding a polypeptide comprising the amino acid sequence set forth in SEQ ID NO: 1; and
   (b) a heterologous promoter operably coupled to the polynucleotide sequence.

2. The genetic construct of claim 1, wherein said polynucleotide sequence comprises a nucleotide sequence set forth in any one of SEQ ID NOS: 13-15, or SEQ ID NO: 23, or a sequence at least 90% identical to any one of SEQ ID NOS: 13-15 or SEQ ID NO: 23.

3. A host cell comprising the genetic construct of claim 1.

4. A method of producing a seed with improved breadmaking properties, including the step of growing a plant capable of producing a seed comprising an increased amount of a protein comprising the amino acid sequence set forth in SEQ ID NO: 1, or an amino acid sequence at least 90% identical to SEQ ID NO: 1, to thereby produce the seed with improved breadmaking properties compared to a reference seed that does not comprise increased amount of said protein.

5. The method of claim 4, wherein the plant is selected from the group consisting of grass species of the family Poaceae, a cereal species, leguminous species, and solanaceous species.

6. The method of claim 5, wherein the plant is a cereal species selected from the group consisting of wheat, rice, barley, oats, maize, and sorghum.

7. The method of claim 6, wherein the plant is wheat.

8. The method of claim 4, wherein the increased amount of said protein of the seed is of the endosperm of said seed.

9. A method of producing a plant or plant part with improved breadmaking properties, wherein said method includes the step of genetically modifying one or more plant cells or tissues to produce a plant capable of producing a seed comprising an increased amount of a protein comprising the amino acid sequence set forth in SEQ ID NO: 1, or an amino acid sequence at least 900 identical to SEQ ID NO: 1, to thereby produce the plant or plant part with improved breadmaking properties compared to a reference plant or part thereof, wherein the reference plant is not capable of producing a seed comprising an increased amount of said protein.

10. The method of claim 9, wherein genetically modifying comprises modifying by genome editing using one or more genetic constructs, wherein the genetic material of the plant or plant part with improved breadmaking properties does not comprise the one or more genetic constructs used for said genome editing.

11. The method of claim 9, wherein the amino acid sequence is at least 95% identical to SEQ ID NO: 1.

12. The method of claim 9, wherein the plant is selected from the group consisting of grass species of the family Poaceae, a cereal species, leguminous species, and solanaceous species.

13. The method of claim 12, wherein the plant is a cereal species selected from the group consisting of wheat, rice, barley, oats, maize, and sorghum.

14. The method of claim 13, wherein the plant is wheat.

15. A method of producing a plant or plant part with improved breadmaking properties, wherein said method includes the steps of:
   (i) identifying one or more parent plants capable of producing a seed comprising an increased amount of a protein comprising the amino acid sequence set forth in SEQ ID NO: 1, or an amino acid sequence at least 90% identical to SEQ ID NO: 1;

(ii) crossing the one or more parent plants together, and/or with one or more other plants to produce progeny plants; and (iii) selecting one or more progeny plants capable of producing a seed comprising an increased amount of said protein, to thereby produce the plant or plant part with improved breadmaking properties compared to a reference plant or part thereof, wherein the reference plant is not capable of producing a seed comprising an increased amount of said protein.

16. The method of claim 15, further comprising introducing one or more mutations into the genetic material of a plant prior to identifying one or more plants capable of producing a seed comprising an increased amount of said protein.

17. The method of claim 15, wherein the plant is wheat, and at least one of the one or more other plants used for crossing is selected from the group consisting of: Sunco, Gregory, Bob White 26, Batavia, Banks, Janz, Condor, Cook, Bounty, Baxter, Oxley, Wylie, Kidman, Hume, Chara, and Leichhardt.

18. The method of claim 15, wherein the plant is selected from the group consisting of grass species of the family Poaceae, a cereal species, leguminous species, and solanaceous species.

19. The method of claim 18, wherein the plant is a cereal species selected from the group consisting of wheat, rice, barley, oats, maize, and sorghum.

20. The method of claim 19, wherein the plant is wheat.

21. A plant with improved breadmaking properties, wherein said plant has been genetically modified or mutagenized such that said plant is capable of producing a seed comprising increased amount of a protein comprising the amino acid sequence set forth in SEQ ID NO: 1, or an amino acid sequence at least 90% identical to SEQ ID NO: 1, compared to a plant that has not been genetically modified or mutagenized.

22. A seed produced from the plant of claim 21.

23. A method of producing bread, the method including the step of processing the seed of claim 22 to thereby produce bread.

24. A plant product produced from the plant of claim 21, wherein the plant product comprises an increased amount of a protein comprising the amino acid sequence set forth in SEQ ID NO: 1, or an amino sequence at least 90% identical to SEQ ID NO: 1.

25. The plant product of claim 24, wherein said product is bread or a bread product.

26. The method of claim 21, wherein the amino acid sequence is at least 95% identical to SEQ ID NO: 1.

* * * * *

SEQUENCE LISTING

```
<160> NUMBER OF SEQ ID NOS: 23

<210> SEQ ID NO 1
<211> LENGTH: 75
<212> TYPE: PRT
<213> ORGANISM: Triticum aestivum

<400> SEQUENCE: 1

Met Phe Phe Ser Thr Lys Met Cys Val Ala Thr Ile Met Val Leu Ala
1               5                   10                  15

Leu Thr Leu Ser Pro His Gly Thr Val Asp Ala Gly His Leu Ser Ser
            20                  25                  30

Asn Trp Gly Ser Cys Pro Asp Gly Gln Ser Val Gln Cys Ile Gly Arg
        35                  40                  45

Pro Pro Phe Cys Lys Cys Val Pro Asn Leu Gln Phe Val Asp Arg Gln
    50                  55                  60

Arg Thr Val Tyr Asn Met Gly Ala Ala Arg Ala
65                  70                  75

<210> SEQ ID NO 2
<211> LENGTH: 1745
<212> TYPE: DNA
<213> ORGANISM: Triticum aestivum

<400> SEQUENCE: 2
ctgtgtgcgt aggaaaataa gtggccttgc tgcactgggc ctcaacgccc gggccaggta      60
cgaaatctgg acaaccgtt tttttcttg cacacgaaat cacaaattta gtaccacctc      120
ggataaaaga aaaatctttt cattggtgaa tggatgaaaa aagcggagaa acgcaccttg      180
ctttattagt actccctccg tttctttata gtctgcatat aacatttggt caaagtcaaa      240
gtttgtaaag tttgaccaac tttgtagaaa aaaatatcaa catctacaat aataaagcta      300
tatggtttga aaattaattt catgatgcat ctaaaaatat tgatttcatt ttgtgaatct      360
tgatattttt ttctataaac ctagtcaaag ttaacaaagt ttgactttgc ccaaacctta      420
tatgcaaact aaaaagaaac ggagggagta ggtatagaat tatattagaa cggttgaccg      480
caaatacttg cgctgcgaga cccgtccata cctgctgaaa agaatgaaga tgtggaggaa      540
tttagatcat caatccgatt gaaggtaagg tagaaagcat ggaccccaca gctcaatctg      600
```

```
ctaaccgtct aggctacaag ctagtgtaac tctgcatatc cctgttagcc atgtaacttc      660
aagggggccaa tgatcgaagt aagatcaatg gtcttcctta cctgccatta acgcataaca      720
gaacaaactg tctgtcaaca ggactgatat ttggtttttg tccgctcaac aactttacat      780
gtagacatta atcatctact agctcactca gaattagaac gattgagatt ttgctgagaa      840
ggtgagacta gacgggcttc taagcaggta ggattcacaa gctcaaaccg ctgagctaaa      900
actatgcatt tggaaacact cccacctaat tttgtttttt cggggaaaca atctacgcca      960
gatttggagg tactcccaac taattttgtt tccttaggaa acaatctacg ccgagcagac     1020
aagaagggag ggatcccgat aacttacggt aatgataact tccgaacgtt cgggagttaa     1080
gcayggcaac ccgaacgggt ttagatggca agtttagttt gcgtgagatt agggaaacat     1140
ggcaattttc tgcaaaaaaa gaaaaaggat aaagttgcca tccccatga actaaagttg     1200
ccatataaaa acgttcggga cgaaacgctc aaaatcccaa cgttcgggag ttattggatt     1260
ccataactta agagttaagt acaaagtaca cgtrcacaca tttatcttgc tatatcggtg     1320
gtgttttatg cgttggtgcc gattaaatac atgacaaact acgttgctcg ttaacttgca     1380
cgctagcact aagtacacct acacagatag atctagagct ctccgtatgt ggtgcttttt     1440
acacttaacg gtaatcaaat gcttgccggc tgcattgctt tttcgcttgt actctacaac     1500
tacatacacg tatacagacc tacagtgctg cataggtggt ggtttgtacg tcaagactga     1560
tctaatatct gccaaacgca tagcttttcc acttatgccg gcatccatcc atcatcgacg     1620
catatccata tacatacgga gtataaatta acacggcccg aggtgagcgc acaccacagc     1680
ggacaacaca gacataaagt gatccataag ataacctgaa gagggtgacg ggctaggcag     1740
ccatg                                                                1745

<210> SEQ ID NO 3
<211> LENGTH: 1745
<212> TYPE: DNA
<213> ORGANISM: Triticum aestivum

<400> SEQUENCE: 3
ctgtgtgcgt rggaaaataa gtggccttgc tgcactgggc ctcaacgccc gggccaggta       60
cgaaatctgg acaacccgtt tttttttctt gcacacgaaa tcacaaattt agtaccacct      120
cggataaaag aaaaatcttt tcattggtga atggatgaaa aaagcggaga aacgcacctt      180
gctttatyag tactccctcc gtttctttttt agtctgcata taacatttgg tcaaagtcaa      240
agtttgtaaa gtttgaccaa ctttgtagaa aaraatatca acatctacaa taataaagct      300
atatggtttg aaaattaatt tcatgatgca tctaaaaata ttgatttcat tttgtgaatc      360
ttgatatttt tttctataaa cctagtcaaa gttaacaaag tttgactttg cccaaacctt      420
atatgcaaac taaaagaaa cggagggagt aggtatagaa ttatattaga acggttgacc      480
gcaaatactt gcgctgcgag acccgtccat acctgctgaa aagaatgaag atgtggagga      540
atttagatca tcaatccgat tgaaggtaag gtagaaagca tggaccccac agctcaatct      600
gctaaccgtc taggctacaa gctagtgtaa ctctgcatat ccctgttagc catgtaactt      660
caaggggcca atgatcgaag taagatcaat ggtcttcctt acctgccatt aacgcataac      720
agaacaaact gtctgtcaac aggactgata tttggttttt gtccgctcaa caactttaca      780
tgtagacatt aatcatctac tagctcactc agaattagaa cgattgagat tttgctgaga      840
aggtgagact agacggcttc taagcaggta ggattcacaa gctcaaaccg ctgagctaaa      900
actatgcatt tggaaacact cccacctaat tttgtttttt cggggaaaca atctacgcca      960
```

```
gatttggagg tactcccaac taattttgtt tccttaggaa acaatctacg ccgagcagac      1020
aagaagggag gratcccgat aacttacggt aatgataact tccgaacgyt cgggagttaa      1080
gcatggcaac ccgaacgggt ttagatggca agtttagttt gcgtgagatt agggaaacat      1140
ggcaattttc tgcaaaaaaa gaaaaaggat aaagttgcca tcccctatga actaaagttg      1200
ccatataaaa acgttcggga cgraacgctc aaaatcccaa cgttcgggag ttattggatt      1260
ccataactta agagttaagt acaaagtaca cgtacacaca tttatcttgc tatatcggtg      1320
gtgttttatg cgttggtgcc gattaaatac atgacaaact acgttgctcg ttaacttgca      1380
cgctagcact aagtacacct acacagatag atctagagct ctccgtatgt ggtgcttttt      1440
acacttaacg gtaatcaaat gcttgccggc tgcattgctt tttcgcttgt actctrcaac      1500
tacatacacg tatacagacc tacagtgctg cataggtggt ggtttgtacg tcaagactga      1560
tctaatatct gccaaacgca tagcttttcc acttgtgccg gcatccatcc atcatcgacg      1620
catatccata tacatacgga gtataaatta acacggcccg aggtgagcgc acaccacagc      1680
ggacaacaca gacataaagt gatccataag ataacctgaa gagggtgacg ggctaggcag      1740
ccatg                                                                 1745

<210> SEQ ID NO 4
<211> LENGTH: 524
<212> TYPE: DNA
<213> ORGANISM: Triticum aestivum

<400> SEQUENCE: 4
cgcaccgact gtgggttttc tccctcgcca atgtcgaccg cgtctacgca gaacattgtt        60
cccttccccc agctgcggga tcaggcccgt cgttctatgc ttgtgaagag agcaacctaa       120
gcaagcaggc ttgtagctta ggctcctgct agtgtatata tagtggtttt cttttttctct      180 caatatcaac cattttatat tgtgtatgtg gtgcttttta cacttaacgg taatcaaatg       240
cttgccggct gcattgcttt ttcgcttgta ctctacaact acatacacgt atacagacct       300
acagtgctgc ataggtggtg gtttgtacgt caagactgat ctaatatctg ccaaacgcat       360
agcttttcca cttgtgccgg catccatcca tcatcgacgc atatccatat acatacggag       420
tataaattaa cacggcccga ggtgagcgca caccacagcg acaacacag acataaagtg        480 atccataaga taacctgaag agggtgacgg gctaggcagc catg                       524

<210> SEQ ID NO 5
<211> LENGTH: 902
<212> TYPE: DNA
<213> ORGANISM: Triticum aestivum

<400> SEQUENCE: 5
cctcaagtgt ataggatcta aattatatta gatcagttga ccgcaaatac atgcgttgcg        60 acaccccgtcc atacctgctg aaaagaatga agatgtggag gaatttagat catcaatccg      120
gttgaaggta gaaagcgtcg accccacagc tcaatctgct aaccgtctag gctacaagct       180
agtgtaactc tcatatccct gttaaccatg taacttcaag ggaccaatga tcgaagtaag      240
atcaatggtc ttccttacct gtcattaacg cataccagaa caaactgtct gtcgacagga       300
ctgatatttt gttttttgtcc gctcaacaac tttacatgta gacactagac actaatcatc       360
tactagctca ctcagaatta gaacgattga gattttgctg agaaggtggg actagacggc       420
ttctaagcag gtaggattca caagctcaaa ccactgagct aaaactatgc atttggaaac       480
```

| | |
|---|---:|
| actcccacct aattttgttt tctcagggaa acaatctacg ccagattaat ttggaagcac | 540 |
| tcccaactaa ttttgttttt agggaagcaa tctacgccat atgtggtgcc ttttacactt | 600 |
| acggtaatca aatgcatggc aggtgcattg cttttcctct tgtactctac aactacatac | 660 |
| acgtatacag atctagagtg ctccataggt ggtggtttgt acgtcaagac tgatctaata | 720 |
| tctgccaaat gcatagcttt tccacttgtg ccggcatcca tccatcgtcg acgcatatcc | 780 |
| atatacatac gggactataa attaacacgg cccgaggtga gcgcacacga caacggacta | 840 |
| caaagacata gagtggtcca taggataacc tgaagagggt ggcgggctag gcagcagcca | 900 |
| tg | 902 |

<210> SEQ ID NO 6
<211> LENGTH: 2160
<212> TYPE: DNA
<213> ORGANISM: Triticum aestivum

<400> SEQUENCE: 6

| | |
|---|---:|
| aacatggtta tttatttctg tcaaattgtc aaattgtaat ctgaataata tgatgctacc | 60 |
| aaaarggtcc cacttyaata gaaccygaca actgggaccc atctgactag tggacccttc | 120 |
| ttttggaaaa aagaaaaac taaattcatt tagacaaaac raaaaggcca caacccaaca | 180 |
| ataaaaaggc tgcaatattg gactyggccc atgaacccaa ccaaaaatyg acagacagaa | 240 |
| aaaaacacra ataggctgaa ttgttrcgct aggcccatgt agaaaatcga attggaccgg | 300 |
| gctgaatctt ctgccacatc agattgccac gctagaygcc tacgtggcct ggggaggttg | 360 |
| ctagtgacca aaacgccata gtagacgtat tttggtcata acatcttcg accattccaa | 420 |
| aagaaaggtc gctatagtca gtttatgacg gccagctttt gaccttatgt ttttgtcat | 480 |
| aaaaaggtca caaatggaaa tttgtgacca ttcagtgacc aataatggtg gtcataagtt | 540 |
| gacatatttc ttgtagtgaa agtggtcgcc cgcctccgtt gagtgcacga cactctacta | 600 |
| ctaaactgag taagttcctc tttattactg tatgcacgcc tgtccatktg ttaaagaaca | 660 |
| aatacggatt tatgtcctat gaattgaccc atacattggt ctcaatagaa acaagaaatt | 720 |
| tatggagtac ggatgtgtat gtgtaactat gagtcttatg gtgtgaagct atctggacta | 780 |
| tgcacgatga tggtgagagc agacggctag gctgtcggca tatctctgcc atgtggcgtc | 840 |
| tcctggtcgt gcagcacttg atggcggcgc catcagccac cgttaggtgt cgaactttgt | 900 |
| cgacggcctg agccgtcggc atagctatat ggacgccgtc gggaaagcat ctatgccgac | 960 |
| gggcttttt atgctgagck gcatycctcg cagagtgatg rcgccccaaa cgtatattgt | 1020 |
| tgcggagcgg ccttacaccg acggggtcat cggcattagc ctgtcgktca caggaattct | 1080 |
| ggctattcga cgcctgggcg tcagcataga ggttattatg gtagtgatga accctgctgg | 1140 |
| gcgaaagttt cattcagcca atagcatggt cctaactaaa agaaggatt tgttatctag | 1200 |
| ggaggatggg attgttttat tgggattta atcggtttga aattgattcc aatttaggcc | 1260 |
| tcaagtgtat aggatctaaa ttatattaga tcrgttgacc gcaaatacat gcgttgcgac | 1320 |
| acccgtccat acctgctgaa aagaatgaag atgtggagga atttagatca tcaatccggt | 1380 |
| tgaaggtaga aagcgtcgac cccacagctc aatctgctaa ccgtctagrc tacaagctag | 1440 |
| tgtaactctc atatccctgt taaccatgta acttcaaggg accaatgatc gaagtaagat | 1500 |
| caatggtctt ccwtacctgt cattaacgca taccagaaca aactgtcygt cgacaggact | 1560 |
| gatatttgt ttttgtccgc tyaacaactt tacatgtaga cactaracac taatcatcta | 1620 |
| ctagctcact cagaattaga acgattgaga tttttgctgag aaggtgggac tagacggctt | 1680 |

| ctaagcaggt aggattcaca agctcaaacc actgagctaa aactatgcat ttggaaacac | 1740 |
| tcccacctaa ttttgttttc tcagggaaac aatctacgcc agattaattt ggaagcactc | 1800 |
| ccaactaatt ttgtttttag ggaagcaatc tacgccatat gtggtgcctt ttacacttac | 1860 |
| ggtaatcaaa tgcatggcag gtgcattgct tttcctcttg tactctacaa ctacatacac | 1920 |
| gtatacagat ctagagtgct ccataggtgg tggtttgtac gtcaagactg atctaatatc | 1980 |
| tgccaaatgc atagctttc cacttgtgcc ggcatccatc catcgtcgac gcatatccat | 2040 |
| atacatacgg gactataaat taacacggcc cgaggtgagc gcacacgaca acggactaca | 2100 |
| aagacataga gtggtccata ggataacctg aagagggtgg cgggctaggc agcagccatg | 2160 |

<210> SEQ ID NO 7
<211> LENGTH: 473
<212> TYPE: DNA
<213> ORGANISM: Triticum aestivum

<400> SEQUENCE: 7

| ggggcagggg agaggggga ggcgcagcct tgcctcttcc tccaaggaag gggtgcggct | 60 |
| aagaggggg aggagtccat cctccccaag gcacctcgga ggtgccttcc ccttttagga | 120 |
| ctcttccctc tagggttccc taggcgcatg ggcctcttgg ggctggtgcc cttggcccat | 180 |
| gtaggccaag gcgcaccccc tacagcccat gtggcccccc ggggcaggtg gccccacccg | 240 |
| gtgggccccc gggacccttc cggtggtccc ggtacaatac cgatgacccc gaaacttgtc | 300 |
| ccgatggccg aaacaggact tcctatatat aaatctttac ctccggacca ttccggaact | 360 |
| cctcgtgact ataaattgat acgcccaagg caaagcccat agaacaaggg actacacaga | 420 |
| cataaagaga tccataactt aacctgaaga gtgtgacgag ataggcagcc atg | 473 |

<210> SEQ ID NO 8
<211> LENGTH: 721
<212> TYPE: DNA
<213> ORGANISM: Triticum aestivum

<400> SEQUENCE: 8

| aatcacatgc aaaatttaag ataagactac cttatcgacc attgtacatg ccctaactta | 60 |
| tagttaagta cgaagtacac gtacacaagt ttgtcttgct atatcggttg tgttttgtgc | 120 |
| gttagtgctg attaaataca tgacaaactg cattgcttgt taacttgcac gctagcacta | 180 |
| agtataccta cgcatataga tctagagtgc tccatacgct ggtgcctttc acacttaatg | 240 |
| acaatcaaat gcatgacagt tgccctgcat tttgccttgt gcgctagcac tacgcacacg | 300 |
| ttgaaggatc tagagtgctt cataggcgat ggtttgcacg ttaccctaat gagatatcta | 360 |
| tcaaccatt cccttctcat ttgtgttggt ctccatctgt catcggcacc aagcaaacct | 420 |
| acggaactat aaattaacag ttttgctaga actcatctag ctgagtttta gttatgtctc | 480 |
| attcactttt atagccattg gatatgatgc tataagatgc gtgtgtgctg atgtgggttg | 540 |
| atacttcttt tctatctgtt ttgtcttcca gatgaatgag actaaattat atctcatcta | 600 |
| aatgagttct aggtactccc ataaattaac acggcctgag gtgagtccac accacaacaa | 660 |
| actacacagg caaagtgata tccataaatt gacctgaagg gcgacctgca agcccgccat | 720 |
| g | 721 |

<210> SEQ ID NO 9
<211> LENGTH: 1287
<212> TYPE: DNA

<213> ORGANISM: Triticum aestivum

<400> SEQUENCE: 9

```
cctaccctag ttgagaagtt tttttgatcc attgaaagct gagacgtgtc tactgaccca      60
taaggcccag ccggacgaca ggttttttgt ttacaaaaag aaaaactgaa acaacttacg     120
ggagggcata aaaacgggaa ggagctcgat cgccacgtat cggctggaac gttgtgagtt    180
cgattcctct tgcaagtata ttttttcttc ctagtattgt actggagctg gccgagctg     240
gccaatggat agcctgcagg cccaagtacc tcctcgctcg cattgcactg ctgggccaag     300
ctggccaaca gacagcctga cgaacatgct attagtacca cctcgtttat attacggttt     360
tatccataca aattgtaaaa gcgtattatg acattagaag aaagcgtatt gtgacggtga     420
acccgacaaa gtcaatccgt gctttattat tattattatt attattatag ggagggatat     480
gtctcaccat gttttttagga atagctagtt attgaagata aggctaagag atgatccatt     540
gtatacactt ttttttgtca tctttaaatc acatgcaaaa tttaagataa gactaccttta     600
tcgaccattg tacatgccct aacttatagt taagtacgaa gtacacgtac acaagttygt     660
cttgctatat cggttgtgtt tgtgcgttaa gtgctgatta aatacatgac aaactgcatt     720
gcttgttaac ttgcacgcta gcactaagta tacctacgca trtagatcta gagtgctcca     780
tacgctggtg cctttcacac ttaatgacaa tcaaatgcat gacagttgcc ctgcattttg     840
ccttgtgcgc tagcactacg cacacgttga aggatctaga gtgcttcata ggcgatggtt     900
tgcacgttac cctaatgaga tatctatcaa ccattccct tctcatttgt gttggtctcc     960
atctgtcatc ggcaccargc aaacctacgg aactataaat taacagtttt gctagaactc    1020
atctagctga gttttagtta tgtctcattc acttttataa ccattggata tgatgctata    1080
agatgcgtgt gtgctgatgt gggttgatac ttctcttcta tctgttttgt cttccagatg    1140
aatgagacta aattatatct catctaaatg agttctaggt actcccataa attaacacgg    1200
cctgaggtga gtccacacca caacaaacta cacaggcaaa gtgatatcca taaattgacc    1260
tgaagggcga cctgtaagcc cgccatg                                         1287
```

<210> SEQ ID NO 10
<211> LENGTH: 1379
<212> TYPE: DNA
<213> ORGANISM: Triticum aestivum

<400> SEQUENCE: 10

```
caacatacgg caactcattt gtaatttact gaacagttag tcagctacca tggtgtataa      60
gacctgctat accatattgt tgtcgtatat tcttatataa gccttttctc ataccatctc     120
atgtatatga aatctgtcat gcacgcaaac acgcaaccac tgagggtacg ccacgttgaa     180
ctagcaggct cttgtttctc aatgcaagca agctccgttg gctgttagga ttagatccta     240
accaccttag gtgggagaga aggcgccgcc gctgtggcat ttgtcgtggt cttctagatt     300
acctgctcgg tcaccttagg ggtacctcta ggtatttgtt tttacttttt gagacaaact     360
catataaagc ttttaattta ttccaccgtc acaagattta cagggttgaa aacaagatct     420
ccgggctgtc ctaaaccaag catggcggtc agtacccagc gttaaagtgt gctttgcaaa     480
gaagcacaat gttttgttcc aaggatgcga acatggcacc agccgtctgt ctccgcccat     540
tctgcatcct cctgctctac ttactttaca cttacagtac aagcaggtat gtcaccttat     600
ttattgaaaa tttgacctca tatcactctc aattacaggg gctggcgaat aataaaacaa     660
actaaaggaa ggatatggat tatgggaagc catgtgtaag atcaatggag tggagggcta     720
```

```
aacaaggaaa gtacacttcg gatttcgaat cactcccagc taattctgtt ttctcgggga      780
agcaacctgt tctagatttg gaatcactcc caaccaatct tcttattggg gaaacaattt      840
gtgccagatt tggaatcact cccaactaat tctgttttcc aggggaaaca attaatccac      900
gccacctaaa catgagtaaa gtacgaagta cacgtactca agtctatctc gctatatcgg      960
tgggtgtttt gtgcgttagt accatgtaaa aaataaatag atgacaaact gcattgctcg     1020
ttaacttgca cgctagcact aagtacacct acagagatat gtagagcc ctccatatgt       1080 ggtgccttt acgcttaatg acaatgaaat cgcgccagc tgcattgctt tttcacttgt       1140
gtgctgcaaa tatgtacacg cgaacggatg tagagtattc catatatagg tggtggtttg     1200
tacgtcaata cttgtctcat atccgccaaa tgcatagctt ttccactttg ttgcgggcac     1260
caaatagaca aatcggacta taaattgata cgcccaaggc aaagcccata gaacaaggga     1320
ctacacagac ataaagagat ccataactta acctgaagag tgtgacgaga taggcagcc     1379
```

```
<210> SEQ ID NO 11
<211> LENGTH: 21
<212> TYPE: DNA
<213> ORGANISM: Artificial sequence
<220> FEATURE:
<223> OTHER INFORMATION: SAGE tag

<400> SEQUENCE: 11
catgttgttc cgtgtagtac c                                                21
```

```
<210> SEQ ID NO 12
<211> LENGTH: 228
<212> TYPE: DNA
<213> ORGANISM: Triticum aestivum

<400> SEQUENCE: 12
atgttcttct ccacaaagat gtgtgttgct accatcatgg tgctagccct gacgctctcg      60
cctcatggca ccgttgacgc cggccacctc tcttcaaact ggggctcttg tccagatgga     120
cagtcagtgc aatgcattgg gagaccgcca ttctgcaagt gtgtaccaaa ccttcagttt     180
gtggatcgcc agcgtactgt gtacaacatg ggagctgccc gtgcatag                   228
```

```
<210> SEQ ID NO 13
<211> LENGTH: 75
<212> TYPE: DNA
<213> ORGANISM: Triticum aestivum

<400> SEQUENCE: 13
atgctattct ccacagacat gtgtgttgct accatcatgg tgctggccct gacgctctcg      60
cttcagggca ccatt                                                       75
```

```
<210> SEQ ID NO 14
<211> LENGTH: 75
<212> TYPE: DNA
<213> ORGANISM: Triticum aestivum

<400> SEQUENCE: 14
atgttcttct ccacaaagat gtgcgttgct gccatcatgg tgctggccct ggcgctctcg      60
cttcagggca ccgtt                                                       75
```

```
<210> SEQ ID NO 15
<211> LENGTH: 75
<212> TYPE: DNA
```

<213> ORGANISM: Triticum aestivum

<400> SEQUENCE: 15
atgttcttct ccacaaagat gtgtgttgct gccatcatgg tgctggccct ggcgctctcg    60
cttcagggca ccgtt    75

<210> SEQ ID NO 16
<211> LENGTH: 75
<212> TYPE: DNA
<213> ORGANISM: Triticum aestivum

<400> SEQUENCE: 16
atgttcttct ccacaaagat gtgtgttgct accatcatgg tgctagccct gacgctctcg    60
cctcatggca ccgtt    75

<210> SEQ ID NO 17
<211> LENGTH: 33
<212> TYPE: DNA
<213> ORGANISM: Triticum aestivum

<400> SEQUENCE: 17
aataagggcc gctgctatat gcgcaggcca ttt    33

<210> SEQ ID NO 18
<211> LENGTH: 33
<212> TYPE: DNA
<213> ORGANISM: Triticum aestivum

<400> SEQUENCE: 18
aataagggct gctactatgt atgcaggcca ttt    33

<210> SEQ ID NO 19
<211> LENGTH: 27
<212> TYPE: DNA
<213> ORGANISM: Artificial sequence
<220> FEATURE:
<223> OTHER INFORMATION: Primer

<400> SEQUENCE: 19
aggtggccgg cgtcaacggt gccatga    27

<210> SEQ ID NO 20
<211> LENGTH: 26
<212> TYPE: DNA
<213> ORGANISM: Artificial sequence
<220> FEATURE:
<223> OTHER INFORMATION: Primer

<400> SEQUENCE: 20
ggctagcacc atgatggtag caacac    26

<210> SEQ ID NO 21
<211> LENGTH: 23
<212> TYPE: DNA
<213> ORGANISM: Artificial sequence
<220> FEATURE:
<223> OTHER INFORMATION: Primer

<400> SEQUENCE: 21
ccgtcacaag atttacaggg ttg    23

<210> SEQ ID NO 22
<211> LENGTH: 24

```
<212> TYPE: DNA
<213> ORGANISM: Artificial sequence
<220> FEATURE:
<223> OTHER INFORMATION: Primer

<400> SEQUENCE: 22
ttatggatct ctttatgtct gtgt                                        24

<210> SEQ ID NO 23
<211> LENGTH: 530
<212> TYPE: DNA
<213> ORGANISM: Triticum aestivum

<400> SEQUENCE: 23
gagaacaagg gactacacag acataaagag atccataact taacctgaag agtgtgacga    60
gataggcagc catgttcttc tccacaaaga tgtgtgttgc taccatcatg gtgctagccc   120
tgacgctctc gcctcatggc accgttgacg ccggccacct ctcttcaaac tggggctctt   180
gtccagatgg acagtcagtg caatgcattg ggagaccgcc attctgcaag tgtgtaccaa   240
accttcagtt tgtggatcgc cagcgtactg tgtacaacat gggagctgcc cgtgcatagt   300
aactagagtt tctagtaata tactatagca ataagagtca tgcagcatcc ctgcatgcat   360
cgccagaaaa cttctgtaca acggaaagcg tgtcaactga acttgatata tgtatgcacc   420
attgcatgca tgttgttccg tgtagtacca gaaaataaaa taagggctgc tactatgtat   480
gcaggccatt tgcttttagc aaaaaaaaaa aaaaaaaaaa aaaaaaaaa              530
```